US009993439B2

(12) United States Patent
Gu et al.

(10) Patent No.: US 9,993,439 B2
(45) Date of Patent: Jun. 12, 2018

(54) MUCOADHESIVE NANOPARTICLE DELIVERY SYSTEM

(71) Applicant: UNIVERSITY OF WATERLOO, Waterloo (CA)

(72) Inventors: Frank X. Gu, Kitchener (CA); Lyndon William James Jones, Waterloo (CA); Shengyan (Sandy) Liu, Waterloo (CA)

(73) Assignee: UNIVERSITY OF WATERLOO, Waterloo (CA)

( * ) Notice: Subject to any disclaimer, the term of this patent is extended or adjusted under 35 U.S.C. 154(b) by 25 days.

(21) Appl. No.: 14/410,521

(22) PCT Filed: Jun. 20, 2013

(86) PCT No.: PCT/CA2013/050475
§ 371 (c)(1),
(2) Date: Dec. 22, 2014

(87) PCT Pub. No.: WO2013/188979
PCT Pub. Date: Dec. 27, 2013

(65) Prior Publication Data
US 2015/0320694 A1 Nov. 12, 2015

Related U.S. Application Data

(60) Provisional application No. 61/690,127, filed on Jun. 20, 2012.

(51) Int. Cl.
*A61K 9/51* (2006.01)
*A61K 47/26* (2006.01)
(Continued)

(52) U.S. Cl.
CPC ............ *A61K 9/5161* (2013.01); *A61K 9/006* (2013.01); *A61K 9/5123* (2013.01);
(Continued)

(58) Field of Classification Search
CPC .............. A61K 47/6937; A61K 47/549; Y10T 428/2982
See application file for complete search history.

(56) References Cited

U.S. PATENT DOCUMENTS 4,649,047 A 3/1987 Kaswan
4,839,342 A 6/1989 Kaswan
(Continued)

FOREIGN PATENT DOCUMENTS

CN 101573141 A 11/2009
EP 0 516 141 B1 8/1996
(Continued)

OTHER PUBLICATIONS

Verma et al. Size-tunable nanoparticles composed of dextran-b-poly(D,L-lactide) for drug delivery applciations. Nano Res. 2012, 5(1):49-61.*

(Continued)

*Primary Examiner* — Lakshmi Channavajjala
(74) *Attorney, Agent, or Firm* — Lathrop Gage LLP; Brian C. Trinque

(57) ABSTRACT

The present disclosure relates generally to a mucoadhesive nanoparticle delivery system. The nanoparticles are formed from amphiphilic macromolecules conjugated to a mucosal targeting moiety in such a manner that the surface of the nanoparticle is coated with the targeting moiety. The surface density of the targeting moiety can be tuned for adjustable targeting of the nanoparticles to a mucosal site without substantially compromising the stability of the particles. The particles were found to have high loading efficiency and sustained release properties at the mucosal site. The present disclosure also relates to polymers and macromolecules (Continued)

useful in the preparation of the mucoadhesive nanoparticles, as well as compositions, methods, commercial packages, kits and uses related thereto.

17 Claims, 19 Drawing Sheets

(51) Int. Cl.
| | |
|---|---|
| A61K 38/13 | (2006.01) |
| A61K 9/00 | (2006.01) |
| A61K 45/06 | (2006.01) |
| A61K 31/131 | (2006.01) |
| A61K 31/69 | (2006.01) |
| A61K 31/78 | (2006.01) |
| A61K 49/00 | (2006.01) |
| A61K 47/54 | (2017.01) |
| A61K 47/69 | (2017.01) |

(52) U.S. Cl.
CPC .......... *A61K 9/5153* (2013.01); *A61K 9/5192* (2013.01); *A61K 31/131* (2013.01); *A61K 31/69* (2013.01); *A61K 31/78* (2013.01); *A61K 38/13* (2013.01); *A61K 45/06* (2013.01); *A61K 47/26* (2013.01); *A61K 47/54* (2017.08); *A61K 47/549* (2017.08); *A61K 47/6935* (2017.08); *A61K 47/6937* (2017.08); *A61K 47/6939* (2017.08); *A61K 49/0002* (2013.01); *Y10T 428/2982* (2015.01)

(56) References Cited

U.S. PATENT DOCUMENTS

| | | | |
|---|---|---|---|
| 6,007,845 | A | 12/1999 | Domb et al. |
| 6,254,860 | B1 | 7/2001 | Garst |
| 6,350,442 | B2 | 2/2002 | Garst |
| 6,525,145 | B2 | 2/2003 | Gevaert et al. |
| 7,803,392 | B2 | 9/2010 | Mumper et al. |
| 8,242,165 | B2 | 8/2012 | Dash et al. |
| 8,323,698 | B2 | 12/2012 | Gu et al. |
| 8,361,439 | B1 | 1/2013 | Sung et al. |
| 2004/0092435 | A1 | 5/2004 | Peyman |
| 2005/0196440 | A1 | 9/2005 | Masters et al. |
| 2005/0281775 | A1 | 12/2005 | Carrington et al. |
| 2006/0263409 | A1 | 11/2006 | Peyman |
| 2010/0006117 | A1 | 1/2010 | Gutierrez |
| 2010/0203142 | A1 | 8/2010 | Zhang et al. |
| 2010/0297007 | A1* | 11/2010 | Lanza ................... A61K 9/1075 424/1.65 |
| 2011/0104069 | A1 | 5/2011 | Ku et al. |
| 2011/0300219 | A1 | 12/2011 | Lippard et al. |
| 2013/0034602 | A1 | 2/2013 | Qian et al. |
| 2014/0005379 | A1 | 1/2014 | Gu |
| 2014/0017165 | A1* | 1/2014 | Wang ................... A61K 9/5146 424/1.37 |
| 2015/0320694 | A1 | 11/2015 | Gu et al. |
| 2016/0243189 | A1 | 8/2016 | Gu et al. |

FOREIGN PATENT DOCUMENTS

| | | |
|---|---|---|
| EP | 1 857 489 A1 | 11/2007 |
| EP | 1 652 517 B1 | 2/2012 |
| EP | 2 510 930 A1 | 10/2012 |
| JP | 3412198 B2 | 6/2003 |
| JP | 2011-140470 A | 7/2011 |
| WO | 1998/030207 A1 | 7/1998 |
| WO | 2000/048576 A1 | 8/2000 |
| WO | 2005/117844 A2 | 12/2005 |
| WO | 2007/124132 A2 | 11/2007 |
| WO | 2008/153966 A1 | 12/2008 |
| WO | 2010/096558 A1 | 8/2010 |

OTHER PUBLICATIONS

U.S. Appl. No. 13/923,274, filed Jun. 20, 2013, Frank Gu.
U.S. Appl. No. 15/142,709, filed Apr. 29, 2016, Frank Gu.
Office Action corresponding to Chinese Patent Application No. 201380040130.1, dated May 4, 2016—with English translation.
Office Action corresponding to U.S. Appl. No. 13/923,274, dated Oct. 1, 2015.
Extended European Search Report corresponding to European Patent Application No. 13806729.3, dated Dec. 22, 2015.
Jeong et al. (2011) "Doxorubicin-incorporated polymeric micelles composed of dextran-b-poly(DL-lactide-co-glycolide) copolymer," Int. J. Nanomedicine. 6:1415-1427.
Liu et al. (Nov. 20, 2012) "Development of mucoadhesive drug delivery system using phenylboronic acid functionalized poly(D,L-lactide)-b-dextran nanoparticles," Macromol. Biosci. 12(12):1622-1626.
Palumbo et al. (2006) "New graft copolymers of hyaluronic acid and polylactic acid: Synthesis and characterization," arbohydrate Polymers. 66(3):379-385.
Raemdonck et al. (2009) "Advanced nanogel engineering for drug delivery," Soft Matter. 5:707-715.
Shen et al. (2010) "Thiolated nanostructured lipid carriers as a potential ocular drug delivery system for cyclosporine A: Improving in vivo ocular distribution," International Journal of Pharmaceutics. 402(1-2):248-253.
Zhong et al. (Sep. 2011) "[Synthesis and cell target recognition property of benzene boric acid modified amphiphilic block copolymers]," In; [The Abstracts of the National Polymer Academic Report, 2011]. [China Chemical Society of Polymer Science Committee]. Abstract No. F-O-18. p. 636—with English translation.
U.S. Appl. No. 13/923,274, Office Action dated Dec. 16, 2016.
U.S. Appl. No. 15/142,709, Office Action dated Feb. 2, 2017.
Barber et al. (2005) "Phase III Safety Evaluation of Cyclosporine 0.1% Ophthalmic Emulsion Administered Twice Daily to Dry Eye Disease Patients for Up to 3 Years," Ophthalmology. 112(10):1790-1794.
Cholkar et al. (Dec. 5, 2012) "Novel Strategies for Anterior Segment Ocular Drug Delivery," Journal of Ocular Pharmacology and Therapeutics. 29(2):106-123.
Li et al. (1997) "Biodegradable brush-like graft polymers from poly (D, L-lactide) or poly (D, L-lactide- co-glycolide) and charge-modified, hydrophilic dextrans as backbone-synthesis, characterization and in vitro degradation properties," Polymer. 38(25):6197-6206.
Liu et al. (Sep. 11, 2014) "Phenylboronic Acid Modified Mucoadhesive Nanoparticle Drug Carriers Facilitate weekly Treatment of Experimentally-Induced Dry Eye Syndrome," Nano Research. 8(2):621-635.
Pflugfelder et al. (2004) "Antiinflammatory Therapy for Dry Eye," American Journal of Ophthalmology. 137(2):337-342.
Sall et al. (2000) "Two Multicenter, Randomized Studies of the Efficacy and Safety of Cyclosporine Ophthalmic Emulsion in Moderate to Severe Dry Eye Disease," Ophthalmology. 107(4):631-639.
Advisory Action corresponding to U.S. Appl. No. 13/923,274, dated Oct. 18, 2016.
International Search Report with Written Opinion for International Patent Application No. PCT/CA2016/050500, dated Jul. 12, 2016.
Allen et al. (1991) "Pharmacokinetics of stealth versus conventional liposomes—effect of dose," Biochim. Biophys. Acta 2:133-141.
Allison (1998) "The Mode of Action of Immunological Adjuvantsm," Dev. Biol. Stand. 92:3-11.
Alpert (1990) "Hydrophilic-interaction chromatography for the separation of peptides, nucleic acids and other polar compounds," Journal of Chromatography A. 499:177-196.
Bazile et al. (1995) "Stealth Me.PEG-PLA nanoparticles avoid uptake by the mononuclear phagocytes system," J. Pharm. Sci. 4:493-498. Pharm.
Bernkop-Schnurch (2001) "Improvement in the mucoadhesive properties of alginate by the covalent attachment of cysteine," Journal of Controlled Release. 71:277-285.

(56) References Cited

OTHER PUBLICATIONS

Chittasupho et al. (2009) "ICAM-1 targeting of doxorubicin-loaded PLGA nanoparticles to lung epithelial cells," Eur. J. Pharm. Sci. 2:141-150.
Cho et al. (2008) "Therapeutic nanoparticles for drug delivery in cancer," Clin. Cancer. Res. 5:1310-1316.
Chouly et al. (1996) "Development of superparamagnetic nanoparticles for MRI: Effect of particle size, charge and surface nature on biodistribution," J. Microencapsul. 3:245-255.
Davidovich-Pinhas et al. (2010) "Novel mucoadhesive system based on sulfhydryl-acrylate interactions," J. Mater. Sci. Mater. Med. 21:2027-2034.
Dhar et al. (2008) "Targeted delivery of cisplatin to prostate cancer cells by aptamer functionalized Pt(IV) prodrug-PLGA-PEG nanoparticles," Proc. Natl. Acad. Sci. USA. 45:17356-17361.
Diebold et al. (2010) "Applications of nanoparticles in ophthalmology," Progress in Retinal and Eye Research. 29:596-609.
Dobrovoiskaia et al. (2008) "Method for analysis of nanoparticle hemolytic properties in vitro," Nano Lett. 8:2180-2187.
Dong et al. (2007) "In vitro and in vivo evaluation of methoxy polyethylene glycol-polylactide (MPEG-PLA) nanoparticles for small-molecule drug chemotherapy," Biomaterials. 28:4154-4160.
Drummond et al. (1999) "Optimizing liposomes for delivery of chemotherapeutic agents to solid tumors," Pharmacol. Rev. 4:691-743.
du Toit et al. (Jan. 2011) "Ocular drug delivery—a look towards nanobioadhesives," Expert Opin. Drug Deliv. 8:71-94.
Esmaeili et al. (2008) "Folate-receptor-targeted delivery of docetaxel nanoparticles prepared by PLGA-PEG-folate conjugate," J. Drug Target. 5:415-423.
Fischer et al. (2003) "In vitro cytotoxicity testing of polycations: influence of polymer structure on cell viability and hemolysis," Biomaterials. 7:1121-1131.
Gaucher et al. (2009) "Effect of Poly(N-vinyl-pyrrolidone)-block-poly(D,L-lactide) as coating agent on the opsonization, phagocytosis, and pharmacokinetics of biodegradable nanoparticles," Biomacromolecules. 2:408-416.
Gaur et al. (2000) "Biodistribution of fluoresceinated dextran using novel nanoparticles evading reticuloendothelial system," Int. J. Pharm. 202:1-10.
Goodwin et al. (2009) "Phospholipid-dextran with a single coupling point: a useful amphiphile for functionalization of nanomaterials," J. Am. Chem. Soc. 1:289-296.
Gu et al. (2008) "Precise engineering of targeted nanoparticles by using self-assembled biointegrated block copolymers," Proc. Natl. Acad. Sci. USA. 7:2586-2591.
Guggi et al. (2004) "Matrix tablets based on thiolated poly(acrylic acid): pH-dependent variation in disintegration and mucoadhesion," International Journal of Pharmaceutics. 274:97-105.
He et al. (2010) "Effects of particle size and surface charge on cellular uptake and biodistribution of polymeric nanoparticles," Biomaterials. 13:3657-3666.
Jung et al. (2005) "Drug release from core-shell type nanoparticles of poly(DL-lactide-co-glycolide)-grafted dextran," J. Microencapsul. 22(8):901-911.
Kafedjiiski et al. (2006) "Improved synthesis and in vitro characterization of chitosan-thioethylamidine conjugate," Biomaterials. 27:127-135.
Karnik et al. (2008) "Microfluidic platform for controlled synthesis of polymeric nanoparticles," Nano Lett. 9:2906-2912.
Kataoka et al. (2001) "Block copolymer micelles for drug delivery: design, characterization and biological significance," Adv. Drug Deliv. Rev. 1:113-131.
Khutoryanskiy (Dec. 27, 2010) "Advances in Mucoadhesion and Mucoadhsive Polymers," Macromol. Biosci. 11:748-764.
Kim et al. (2005) "Interaction of PLGA nanoparticles with human blood constituents," Colloids Surf. B Biointerfaces. 2:83-91.
Kim et al. (Jan. 27, 2012) "Antitumor activity of sorafenib-incorporated nanoparticles of dextran/poly(dl-lactide-co-glycolide) block copolymer," Nanoscale Res. Lett. 7(1):91.

Kusnierz-Glaz et al. (1997) "Granulocyte colony-stimulating factor-induced comobilization of CD4(−)CD8(−) T cells and hematopoietic progenitor cells (CD34(+)) in the blood of normal donors," Blood. 7:2586-2595.
Lee et al. (2006) "Thiolated chitosan nanoparticles enhance anti-inflammatory effects of intranasally delivered theophylline," Resp. Res. 7:112.
Lee et al. (2010) "The effects of particle size and molecular targeting on the intratumoral and subcellular distribution of polymeric nanoparticles," Mol. Pharm. 4:1195-1208.
Li et al. (1998) "Biodegradable brush-like graft polymers from poly(D,L-lactide) or poly(D,L-lactide-coglycolide) and charge-modified, hydrophilic dextrans backbone—in-vitro degradation and controlled releases of hydrophilic macromolecules," Polymer. 39:3087-3097.
Li et al. (2008) "Pharmacokinetics and biodistribution of nanoparticles," Mol. Pharm. 4:496-504.
Li et al. (Jan. 2012) "Low molecular weight chitosan-coated liposomes for ocular drug delivery: In vitro and in vivo studies," Drug Deliv. 19:28-35.
Liu et al. (Apr. 17, 2012) "Nanomaterials for Ocular Drug Delivery," Macromolecular Bioscience. 12:608-620.
Lorentz et al. (Dec. 24, 2011) "Contact lens physical properties and lipid deposition in a novel characterized artificial tear solution," Molecular Vision. 17:3392-3405.
Ludwig (2005) "The use of mucoadhesive polymers in ocular drug delivery," Adv. Drug Deliv. Rev. 57:1595-1639.
Magenheim et al. (1993) "A new in vitro technique for the evaluation of drug release profile from colloidal carriers—ultrafiltration technique at low pressure," Int. J. Pharm. 94:115-123.
Matsumoto et al. (2009) "Noninvasive Sialic Acid Detection at Cell Membrane by Using Phenylboronic Acid Modified Self-Assembled Monolayer Gold Electrode," J. Am. Chem. Soc. 131:12022-12023.
Matsumoto et al. (2010) "Assessment of Tumor Metastasis by the Direct Determination of Cell-Membrane Sialic Acid Expression," Angewandte Chemie-International Edition. 49:5494-5497.
Meerasa et al. (May 2011) "CH(50): A revisited hemolytic complement consumption assay for evaluation of nanoparticles and blood plasma protein interaction," Curr. Drug Deliv. 3:290-298.
Missirlis et al. (2006) "Doxorubicin encapsulation and diffusional release from stable, polymeric, hydrogel nanoparticles," Eur. J. Pharm. Sci. 2:120-129.
Nagarwal et al. (2009) "Polymeric nanoparticulate system: A potential approach for ocular drug delivery," J. Controlled Release. 136:2-13.
Nouvel et al. (2009) "Biodegradable nanoparticles made from polylactide-grafted dextran copolymers," J. Colloid Interface Sci. 330(2):337-343.
Passirani et al. (1998) "Long-circulating nanoparticles bearing heparin or dextran covalently bound to poly(methyl methacrylate)," Pharm. Res. 7:1046-1050.
Peracchia et al. (1999) "Stealth (R) PEGylated polycyanoacrylate nanoparticles for intravenous administration and splenic targeting," J. Control. Release 1:121-128.
Phillips et al. (1992) "Enhanced antibody response to liposome-associated protein antigens: preferential stimulation of IgG2a/b production," Vaccine. 10:151-158.
Portet et al. (2001) "Comparative biodistribution of thin-coated iron oxide nanoparticles TCION: Effect of different bisphosphonate coatings," Drug Dev. Res. 4:173-181.
Rehor et al. (2008) "Functionalization of polysulfide nanoparticles and their performance as circulating carriers," Biomaterials. 12:1958-1966.
Riley et al. (1999) "Colloidal stability and drug incorporation aspects of micellar-like PLA-PEG nanoparticles," Colloids Surf. B Biointerfaces. 16:147-159.
Riley et al. (2001) "Physicochemical evaluation of nanoparticles assembled from poly(lactic acid)-poly(ethylene glycol) (PLA-PEG) block copolymers as drug delivery vehicles," Langmuir. 11:3168-3174.
Sacco et al. (2010) "The Average Body Surface Area of Adult Cancer Patients in the UK: A Multicentre Retrospective Study," Plos One. 1:e8933-e8933.

(56) References Cited

OTHER PUBLICATIONS

Safra et al. (2000) "Pegylated liposomal doxorubicin (doxil): Reduced clinical cardiotoxicity in patients reaching or exceeding cumulative doses of 500 mg/m(2)," Ann. Oncol. 8:1029-1033.
Sakloetsakun et al. (2009) "In situ gelling properties of chitosan-thioglycolic acid conjugate in the presence of oxidizing agents," Biomaterials. 30:6151-6157.
Schmitz et al. (2008) "Synthesis and characterization of chitosan-N-acetyl cysteine conjugate," International Journal of Pharmaceutics. 347:79-85.
Shaikh et al. (Jan.-Mar. 2011) "Mucoadhesive drug delivery systems," J. Pharm. Bioallied Sci. 3(1):89-100.
Shen et al. (2010) "Thiolated chitosan nanopariticles enhance anti-inflammatory effects of intransally delivered theophylline," Respir Res. 7(1):112.
Shuai et al. (2004) "Micellar carriers based on block copolymers of poly(e-caprolactone) and poly(ethylene glycol) for doxorubicin delivery," J. Control. Release 3:415-426.
Sogias et al. (2008) "Why is Chitosan Mucoadhesive?" Biomacromolecules. 9:1837-1842.
Takeuchi et al. (2005) "Novel mucoadhesion tests for polymers and polymer-coated particles to design optimal mucoadhesive drug delivery systems," Advanced Drug Delivery Reviews. 57:1583-1594.
Unkeless et al. (1988) "Structure and function of human and murine receptors for IgG," Annu. Rev. Immunol. 6:251-281.
Verma et al. (Jan. 2012) "Size-tunable nanoparticles composed of dextran-b -poly(D,L-lactide) for drug delivery applications," Nano Research. 5:49-61.
Yang et al. (2009) "Pharmacokinetics and biodistribution of near-infrared fluorescence polymeric nanoparticles," Nanotechnology 16:165101.
Yuan et al. (2006) "Preparation of cholesterol-modified chitosan self-aggregated nanoparticles for delivery of drugs to ocular surface," Carbohydrate Polymers. 65:337-345.
Zahr et al. (2006) "Macrophage uptake of core-shell nanoparticles surface modified with poly(ethylene glycol)," Langmuir. 19:8178-8185.
Zimmer et al. (1995) "Microspheres and nanoparticles used in ocular delivery systems," Adv. Drug Deliv. Rev. 16:61-73.
Gao et al. (Jan. 24, 2006) "Lectin-conjugated PEG-PLA nanoparticles: Preparation and brain delivery after intranasal administration," Biomaterials. 27:3482-3490.
Garinot et al. (Apr. 30, 2007) "PEGylated PLGA-based nanoparticles targeting M cells for oral vaccination," Journal of Controlled Release. 120:195-204.
Notice of Reasons for Rejection corresponding to Japanese Patent Application No. 2015-517568, dated Apr. 10, 2017.
Liu et al. (2010) "Synthesis of a linear copolymer Poly(lactic acid)-beta-dextran for drug delivery," In; The Abstracts of the XVIII International Conference on Bioencapsulation, Porto, Portugal, Oct. 1-2, 2010. Abstract No. O1-2. pp. 16-17.
Liu et al. (2010) "Synthesis of a linear copolymer Poly(lactic acid)-beta-dextran for drug delivery," In; The XVIII International Conference on Bioencapsulation, Porto, Portugal, Oct. 1-2, 2010. Presentation corresponding to Abstract No. O1-2, 16 pgs.
Liu et al. (2011) "Linear block copolymer Dextran-b-Poly(D,L-lactide) nanoparticles for ocular drug delivery," In; The Abstracts of the XIX International Conference on Bioencapsulation, Amboise, France, Oct. 5-8, 2011. Abstract No. O9-4. pp. 96-97.
Liu et al. (2011) "Linear block copolymer Dextran-b-Poly(D,L-lactide) nanoparticles for drug delivery applications," In; The XIX International Conference on Bioencapsulation, Amboise, France, Oct. 5-8, 2011. Presentation corresponding to Abstract No. O9-4, 15 pgs.
Liu et al. (Sep. 2012) "Mucoadhesive nanoparticles for topical ocular drug delivery," In; The Abstracts of the XX International Conference on Bioencapsulation, Orilla, Ontario, Sep. 21-24, 2012. Abstract No. P27. pp. 148-149.
Liu et al. (Sep. 2012) "Mucoadhesive nanoparticles for topical ocular drug delivery," In; The XX International Conference on Bioencapsulation, Orilla, Ontario, Sep. 21-24, 2012. Poster corresponding to Abstract No. P27, 1 pg.
Office action corresponding to Chinese Patent Application No. 201380040130.1, dated Feb. 17, 2017—provided with an English translation.
Intention to Grant corresponding European Patent Application No. 13806729.3 with Granted Claims, dated Jun. 1, 2017.
Chinese Patent Application No. CN201380040130.1, Notice of Allowance dated Mar. 6, 2018, 2 pp.

* cited by examiner

MUCOADHESIVE NANOPARTICLE DELIVERY SYSTEM

CROSS REFERENCE TO RELATED APPLICATIONS

This application claims the benefit of priority of U.S. Provisional Patent Application No. 61/690,127, filed Jun. 20, 2012, which is incorporated herein by reference in its entirety.

TECHNICAL FIELD

The present disclosure relates generally to a mucoadhesive nanoparticle delivery system. The nanoparticles can be tuned for controlled targeting and adhesion of the nanoparticles at a mucosal site without substantially compromising the stability of the particles. The present disclosure also relates to components useful in the preparation of the nanoparticles, as well as to compositions, methods, processes, commercial packages, kits and uses related thereto.

BACKGROUND

The delivery of a drug to a patient with controlled release of the active ingredient has been an active area of research for decades and has been fueled by the many recent developments in polymer science. Controlled release polymer systems can be designed to provide a drug level in the optimum range over a longer period of time than other drug delivery methods, thus increasing the efficacy of the drug and minimizing problems with patient compliance.

Nanomedicine—the fusion of nanotechnology and medicine—is among the most promising approaches to address challenges associated with conventional drug delivery methods. In the past decade, drug delivery systems constructed from polymeric nanoparticles (NPs) have been the cornerstone of progress in the field of nanomedicine. Various types of polymeric materials have been studied for NP drug delivery applications.

PLGA-PEG is the most widely used polymer for making biodegradable drug delivery systems. The self-assembly of PLGA-PEG block copolymers generally yields NPs of sizes greater than 150 nm (Karnik, 2008). Although smaller particles can be synthesized, they generally suffer from low drug encapsulation and rapid drug release (Karnik, 2008). The present inventors reported that typical maximum drug loading in PLGA-PEG was found to be 7.1 wt/wt % (Verma, 2012, incorporated herein by reference in its entirely). Other PEG based polymers showed drug loading ranging from 4.3 to 11.2 wt/wt % (Shuai, 2004; He, 2010; Missirlis, 2006).

Nanoparticles have been developed as sustained release vehicles used in the administration of small molecule drugs as well as protein and peptide drugs and nucleic acids. The drugs are typically encapsulated in a polymer matrix which is biodegradable and biocompatible. As the polymer is degraded and/or as the drug diffuses out of the polymer, the drug is released into the body. Typically, polymers used in preparing these particles are polyesters such as poly(lactide-co-glycolide) (PLGA), polyglycolic acid, poly-beta-hydroxybutyrate, polyacrylic acid ester, etc. These particles can also protect the drug from degradation by the body. Furthermore, these particles can be administered using a wide variety of administration routes. Various types of materials used for synthesizing nanoparticle drug carriers have been disclosed, for example, in US. Pat. No. 2011/0300219. Amphiphilic compound assisted nanoparticles for targeted delivery have been disclosed, for example, in US. Pat. No. 2010/0203142.

Targeting controlled release polymer systems (e.g., targeted to a particular tissue or cell type or targeted to a specific diseased tissue but not normal tissue) is desirable. It can enhance the drug effect at the target site and reduce the amount of a drug present in tissues of the body that are not targeted. Therefore, with effective drug targeting, it may be possible to reduce the amount of drug administered to treat a particular disease or condition and undesirable side effects may also be reduced.

Various benefits can be obtained through delivery of therapeutic agents through a mucosal tissue. For example, mucosal delivery is generally non-invasive, thereby avoiding uncomfortable aspects of intravenous, intramuscular, or subcutaneoud delivery means. Application of a therapeutic agent to a mucosal tissue can also reduce the effect of first-pass metabolism and clearance by circulating immune cells. However, given the tendency of natural bodily fluids to clear applied therapeutic agents from the site of administration, the administration of therapeutic agents to mucosal sites, such as the eye, nose, mouth, stomach, intestine, rectum, vagina, or lungs, among others, can be problematic.

Topical administration is the most common delivery method employed for treating diseases and conditions affecting the eye, such as corneal diseases. Common topical formulations, such as eye drops or ointments, suffer from low ocular bioavailability due to rapid drainage through the naso-lacrimal duct, near constant dilution by tear turnover, and low drug permeability across the corneal epithelium. As a result, topical formulations are normally administered multiple times daily in order to achieve therapeutic efficacy, resulting in a higher potential for side effects and lower patient compliance.

Recently, formulations using NPs as drug carriers have been proposed to overcome the limitation associated with topical administration methods. NP carriers have been shown to improve drug stability in water and also prolong drug activity by releasing encapsulated compounds in a controlled manner (Ludwig, 2005; Nagarwal 2009; Liu, 2012). NPs formulated using biodegradable polymers, such as poly(lactic-co-glycolic acid) (PLGA), have been tested for ocular topical drug delivery applications (Diebold, 1990; Zimmer, 1995). Poly(ethylene glycol)-based NPs have attracted significant attention due to their ability to improve the stability of drug carrier systems in physiological environments (Bazile, 1995; Dhar, 2008; Dong, 2007; Esmaeili, 2008).

The synthesis of surface-functionalized NP drug delivery systems has been explored. In order to achieve mucoadhesion, the synthesis typically requires two-stage synthesis whereby the first stage involves the formation of NPs, while the second stage involves the conjugation of ligands on the surface of these NPs. Recently, a new technology demonstrated the formation of targeting NPs using one-step synthesis whereby the formation of the NP and the surface functionalization can be accomplished in one step (U.S. Pat. No. 8,323,698, incorporated herein by reference). This technology is particularly useful for applications where minimal targeting ligand is required, e.g. for systemic bolus injections where the number of targeting ligands on the surface must be controlled to minimize systemic immunogenicity. When nanoparticles are formed using the one-step method, targeting ligands may be detected within the core of the nanoparticles. Thus, this methodology may not be ideal where maximum targeting is desired.

The surfaces of polymeric NPs have been functionalized with molecular ligands that can selectively bind to the ocular mucosa to increase precorneal drug retention (du Toit, 2011; Khutoryanskiy, 2011; Shaikh, 2011). To date, the most widely used method to achieve mucoadhesion exploits electrostatic interactions between the negatively charged sialic acid moieties of the corneal mucin and cationic polymers such as chitosan (Sogias, 2008). However, the electrostatic interactions may be hindered by various counter ions in the tear fluid, resulting in the clearance of these NPs by tear turnover.

A number of molecular targeting groups have been suggested in the past for targeting the human mucosal lining: U.S. Pat. No. 7,803,392 B2 filed Dec. 8, 2011, entitled "pH-sensitive mucoadhesive film-forming gels and wax-film composites suitable for topical and mucosal delivery of molecules"; US Pat. 2005/0196440, filed Sep. 8, 2005, entitled "Mucoadhesive drug delivery devices and methods of making and using thereof"; US Pat. 2005/0281775, filed Dec. 22, 2005, entitled "Mucoadhesive and bioadhesive polymers"; EP 2167044 A1, filed Dec. 11, 2008, entitled "Mucoadhesive vesicles for drug delivery"; WO 2005/117844, filed Sep. 17, 2009, entitled "Mucoadhesive nanocomposite delivery system"; WO 2010/096558, filed Feb. 18, 2010, entitled "Bi-functional co-polymer use for ophthalmic and other topical and local applications"; US Pat. 2013/0034602, filed Jul. 30, 2012, entitled "Enteric-coated capsule containing cationic nanoparticles for oral insulin delivery", EP Pat. 2510930 A1, filed Apr. 15, 2011, entitled "Nanoparticles comprising half esters of poly (methyl vinyl ether-co-maleic anhydride) and uses thereof"; U.S. Pat. No. 8,242,165 B2, filed Oct. 26, 2007, entitled "Mucoadhesive nanoparticles for cancer treatment"; EP Pat. 0516141 B1 filed May 29, 1992, entitled "Pharmaceutical controlled-release composition with bioadhesive properties"; WO 1998/030207 A1, filed Jan. 14, 1998, entitled "Chitosan-gelatin a microparticles"; EP Pat. 1652517 B1, filed Jun. 17, 2004, entitled "Hyaluronic acid nanoparticles"; U.S. Pat. No. 8,361,439 B1, filed Aug. 20, 2012, entitled "Pharmaceutical composition of nanoparticles". However, these documents only describe mucoadhesive materials that undergo physical interaction with the mucous lining (e.g. electrostatic interaction between cationic chitosan materials with the negatively charged mucin layer). The main disadvantage of physical interaction is that it is unspecific and much weaker compared to covalent interactions.

A few studies have reported molecular targeting groups with potential to covalently bind to mucosal tissue. Phenylboronic acid (PBA), which contains a phenyl substituent and two hydroxyl groups attached to boron, has been reported to form a complex with the diol groups of sialic acid at physiological pH (Matsumoto, 2010; Matsumoto, 2010; Matsumoto, 2009). Another class of molecules that can covalently bind to the mucous membrane is polymeric thiomers (Ludwig, 2005). These thiomers are capable of forming covalent disulfide linkage with cysteine-rich subdomains of the mucous membrane (Khutoryanskiy, 2010). Typical examples of polymeric thiomers include the following conjugates: poly(acrylic acid)/cysteine (Gugg, 2004), chitosan/N-acetylcysteine (Schmitz, 2008), alginate/cysteine (Bernkop-Schnurch, 2008) chitosan/thio-glycolic acid (Sakloetsakun, 2009) and chitosan/thioethylamidine (Kafedjiiski, 2006). A recent study also suggested that polymers with acrylate end groups are also capable of binding to the thiol moieties of mucous membrane through Michael addition (Davidovich-Pinhas and Bianco-Peled 2010). The study demonstrated that the poly(ethylene glycol) diacrylate formed stable covalent linkage with thiol groups of freshly extracted porcine small intestinal mucin under physiological conditions, which was confirmed using NMR characterization.

It is desirable to provide targeted nanoparticle delivery systems for controlled delivery of a payload to a mucosal site. In particular, it is desirable to provide improved mucoadhesive delivery systems that can be retained at a mucosal site for a sufficient period of time to provide sustained release of the payload. It is particularly desirable to be able to tune such delivery systems such that the extent of targeting and adhesion can be controlled without substantially compromising the stability of the delivery system.

SUMMARY

The present disclosure relates generally to a mucoadhesive nanoparticle delivery system.

In a first aspect, the present disclosure provides a nanoparticle composition useful for delivery of a payload to a mucosal site, the nanoparticle comprising a plurality of amphiphilic macromolecules, the macromolecules comprising: a hydrophobic portion; a hydrophilic portion comprising multiple functional moieties; and a mucosal targeting moiety, wherein at least a portion of said functional moieties on the hydrophilic portion are conjugated to the mucosal targeting moiety.

In further aspect, the present disclosure provides a nanoparticle composition useful for delivery of a payload to a mucosal site, the nanoparticle comprising a plurality of amphiphilic macromolecules, the macromolecules comprising: a hydrophobic portion comprising a biocompatible polymer selected from a from polylactide, a polyglycolide, poly(lactide-co-glycolide), poly($\varepsilon$-caprolactone), or a combination thereof; a hydrophilic portion comprising a biocompatible polymer selected from polysaccharide, polynucleotide, polypeptide, or a combination thereof, the hydrophilic portion comprising multiple functional moieties; and a mucosal targeting moiety selected from a phenylboronic acid (PBA) derivative, a thiol derivative or an acrylate derivative, wherein at least a portion of said functional moieties of the hydrophilic portion are conjugated to the mucosal targeting moiety.

In a further embodiment, there is provided a nanoparticle composition useful for delivery of a payload to a mucosal site, the nanoparticle comprising a plurality of amphiphilic macromolecules, the macromolecules each comprising: a hydrophobic biocompatible polymer selected from a from polylactide, a polyglycolide, poly(lactide-co-glycolide), poly($\varepsilon$-caprolactone), or a combination thereof, the hydrophobic polymer forming the core of the nanoparticle; a hydrophilic biocompatible polymer selected from polysaccharide, polynucleotide, polypeptide, or a combination thereof, having multiple functional moieties, the hydrophilic portion forming the shell of the nanoparticle; at least a portion of the functional moieties being conjugated to a mucosal targeting moiety selected from a phenylboronic acid (PBA) derivative, a thiol derivative or an acrylate derivative.

In a further embodiment, there is provided a nanoparticle composition useful for delivery of a payload to a mucosal site, the nanoparticle comprising a plurality of amphiphilic macromolecules, the macromolecules comprising: a hydrophobic portion comprising a polylactide; a hydrophilic portion having multiple functional moieties, said hydrophilic portion comprising dextran; and a mucosal targeting moiety being a phenylboronic acid (PBA) derivative, wherein at least a portion of said functional moieties of the hydrophilic portion are conjugated to the mucosal targeting moiety.

In a further embodiment, there is provided a nanoparticle composition useful for delivery of a payload to a mucosal site, the nanoparticle comprising a plurality of amphiphilic macromolecules, the macromolecules each comprising a hydrophobic polylactide polymer conjugated to a hydrophilic dextran polymer having multiple functional moieties, at least a portion of said functional moieties being conjugated to a phenylboronic acid (PBA) derivative.

In a further embodiment, there is provided a Dextran-p-PLA block copolymer, wherein at least a portion of the functional groups on the Dextran are conjugated to a targeting moiety capable of forming a high affinity bond with a target at a mucosal site.

In some embodiments, the nanoparticle is formed by conjugating the polylactide to the dextran to form a nanoparticle and subsequently surface-functionalizing the nanoparticle by conjugating at least a portion of the functional moieties of the dextran to the PBA derivative to achieve a desired surface density of the PBA derivative.

In some embodiments, the nanoparticle is formed by conjugating the polylactide to the dextran to form a nanoparticle and subsequently reacting the functional moieties of the dextran with PBA such that substantially all of the PBA is located in the shell/on the surface of the nanoparticle.

In some embodiments, the core of the nanoparticle is substantially free of targeting moiety.

In another aspect, there is provided a pharmaceutical composition comprising a nanoparticle composition as defined in herein, and a pharmaceutically acceptable carrier.

In another aspect, there is provided a mucoadhesive delivery system for delivering a payload to a mucosal surface, the delivery system comprising a nanoparticle composition as defined herein; a pharmaceutically acceptable carrier; and a payload.

In another aspect, there is provided a method of treating or preventing a disease or condition comprising administering to a subject an effective amount of a nanoparticle composition or pharmaceutical composition as described herein.

In another aspect, there is provided a use of the nanoparticle composition or pharmaceutical composition as described herein for treating a disease capable of being treating by administering a therapeutic agent to a mucosal site.

In another aspect, there is provided a use of the nanoparticle composition as described herein in the manufacture of a medicament for treating a disease capable of being treating by administering a therapeutic agent to a mucosal site.

In another aspect, there is provided a nanoparticle composition or pharmaceutical composition as described herein for use in treating a disease capable of being treating by administering a therapeutic agent to a mucosal site.

In another aspect, there is provided a commercial package comprising the nanoparticle composition or pharmaceutical composition as described herein, together with instructions for use in treating a disease.

In another aspect, there is provided a method of preparing a nanoparticle composition useful for delivery of a payload to a mucosal site, the method comprising: a) preparing an amphiphilic macromolecule comprising a hydrophilic portion and a hydrophobic portion, the hydrophilic portion comprising multiple functional moieties; b) assembling a plurality of said macromolecules under suitable conditions to form a nanoparticle having a hydrophobic core and a hydrophilic shell; and c) conjugating at least a portion of said functional moieties on the hydrophobic portion to a mucosal targeting moiety to provide a surface-functionalized nanoparticle.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
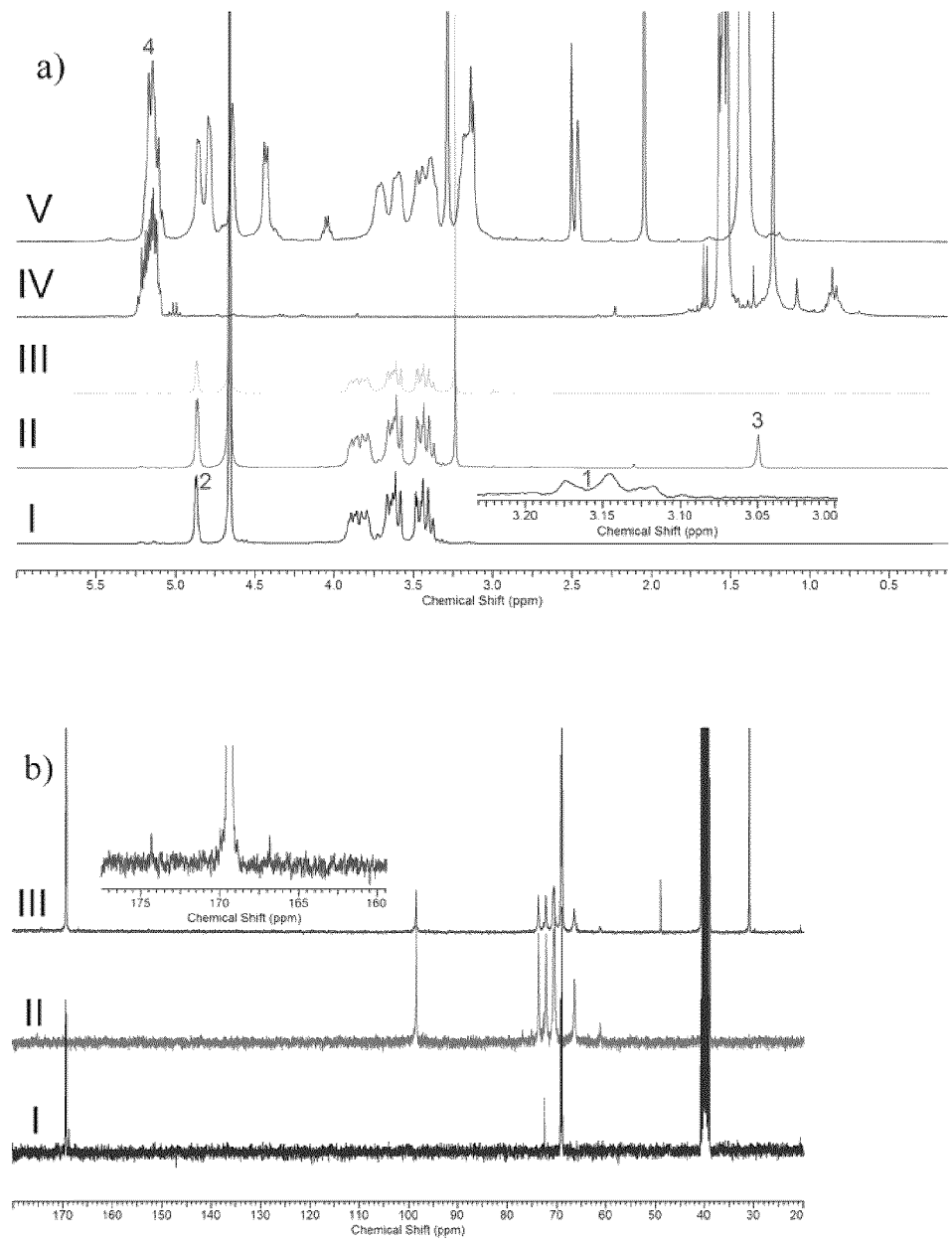
FIG. 1 is NMR spectra at various steps of block copolymer synthesis: a) Proton NMR of I. Dextran 6 kDa (D2O), II. Dextran-NH-Et-NH-Boc (D2O), III. Dextran-NH-Et-NH2 (D2O), IV. PLA 20 kDa (DMSO-d6), V. Dextran-Et-PLA, or PLA20-Dex6 (DMSO-d6); b) Carbon NMR of block copolymer I. PLA 20 kDa, II. Dextran 6 kDa, III Dex-Et-PLA (PLA20-Dex6) confirming conjugation of Dextran and PLA.

Generally, the present disclosure relates to a mucoadhesive nanoparticle delivery system. The nanoparticles are formed from amphiphilic macromolecules, such as block copolymers, comprising a hydrophilic portion and a hydrophobic portion. The hydrophobic portion comprises multiple functional groups capable of being conjugated to a targeting moiety, such as a mucosal targeting moiety. In an aqueous environment, the hydrophilic portion forms the shell of the nanoparticle providing a surface that can be functionalized by coating the nanoparticle with a desired surface density of the targeting moiety. The size of the nanoparticles and the surface density of the targeting moieties can be tuned without substantially compromising the stability of the particles. The nanoparticles are useful for delivering a wide variety of payloads to a mucosal site in a subject and are capable of providing sustained release of the payload. The nanoparticles demonstrate good loading capacity and loading efficiency.

The present disclosure also relates to components useful in the preparation of the mucoadhesive nanoparticles, as well as compositions, methods, processes, commercial packages, kits and uses related thereto.

Macromolecules

The nanoparticles of the present disclosure are generally formed by the association or assembly of amphiphilic macromolecules. The macromolecules are composed of at least a hydrophobic portion and at least one hydrophilic portion. The macromolecule may comprise a hydrophobic polymer conjugated to a hydrophilic polymer. Such macromolecules are capable of self-assembly to form nanoparticles according to methods well known to those skilled in the art, including nanoprecipitation methods.

A "polymer," as used herein, refers to a molecular structure comprising one or more repeat units (e.g. monomers), connected by covalent bonds. The repeat units may be identical, or in some cases, there may be more than one type of repeat unit present within the polymer. Polymers may be obtained from natural sources or they may be chemically synthesized. In some cases, the polymer is a biopolymer, such as a polysaccharide, polypeptide or polynucleotide. Biopolymers may comprise naturally-occurring monomers or derivatives or analogs thereof, for example, derivatives or analogs comprising modified sugars, nucleotides or amino acids. Several such modifications are known to those skilled in the art. In some cases, the polymer is a synthetic polymer, such as polylactide (PLA), polyglycolide (PGA), or poly (lactide-co-glycolide) (PLGA) or poly(ε-caprolactone) (PCL).

If more than one type of repeat unit is present within the polymer, then the polymer is said to be a "copolymer." The repeat units forming a copolymer may be arranged in any fashion. For example, the repeat units may be arranged in a random order, in an alternating order, or in "blocks". As used herein, a "block copolymer" comprises two or more distinct blocks or regions, e.g. at least a first block comprising a first polymer and a second block comprising a second polymer. It should be understood that, in this context, the terms "first" and "second" do not describe a particular order or number of elements but are merely descriptive. A block copolymer may have two (a "diblock copolymer"), three (a "triblock copolymer"), or more distinct blocks.

Block copolymers may be chemically synthesized or may be polymeric conjugates. As used herein, a "polymeric conjugate" describes two or more polymers that have been associated with each other, usually by covalent bonding of two or more polymers together. Thus, a polymeric conjugate may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer. For instance, a block copolymer may comprise a first block comprising a first polymer, a second block comprising a second polymer, and a third block comprising a third polymer or the first polymer, etc. In addition, it should be noted that block copolymers can also be formed, in some instances, from other block copolymers. For example, a first block copolymer may be conjugated to another polymer to form a new block copolymer containing multiple types of blocks. The polymers may be conjugated by any means known in the art and may optionally be connected by an appropriate linker moiety.

An amphiphilic block copolymer generally has a hydrophobic portion and a hydrophilic portion, or at least a relatively hydrophilic portion and a relatively hydrophobic portion when two portions are considered relative to each other. A hydrophilic polymer is one that generally attracts water and a hydrophobic polymer is one that generally repels water. A hydrophilic or a hydrophobic polymer can be identified, for example, by preparing a sample of the polymer and measuring its contact angle with water (typically, the hydrophilic polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer.

In some embodiments, the macromolecule is a copolymer comprising a hydrophobic portion and a hydrophilic portion. In some embodiments, the macromolecule is a diblock copolymer comprising a first hydrophilic polymer and a second hydrophobic polymer. Such configurations are generally useful for forming nanoparticles for encapsulating hydrophobic agents of interest in an aqueous environment, such as under physiologic conditions, since the hydrophobic portions will shelter the hydrophobic agent in the core region of the nanoparticle and the hydrophilic portion will form the shell of the nanoparticle by orienting toward the aqueous environment.

In one embodiment, the macromolecule is a Dextran-b-PLA (Dex-b-PLA) diblock copolymer, which may optionally be functionalized on the dextran portion with one or more targeting moieties, such as a mucosal targeting moiety.

In some embodiments, the macromolecule is a triblock copolymer comprising a first hydrophilic polymer, a second hydrophobic polymer, and third hydrophilic polymer. Such configurations are generally useful for forming nanoparticles for encapsulating hydrophilic agents of interest in an aqueous environment, such as under physiologic conditions.

Since the macromolecule will be exposed to bodily tissues, it is preferable that the macromolecule comprises a biocompatible polymer, for example, the polymer does not induce a significant adverse response when administered to a living subject, for example, it can be administered without causing significant inflammation, irritation and/or acute rejection by the immune system.

In some embodiments, the biocompatible polymer is biodegradable, for example, the polymer is able to degrade, chemically and/or biologically, within a physiological environment, such as when exposed to a body tissue. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of hours, days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Non-limiting examples of biodegradable polymers include, but are not limited to, polysaccharides, polynucleotides, polypeptides, poly(lactide) (or poly(lactic acid)), poly(glycolide) (or poly(glycolic acid)), poly(orthoesters), poly(caprolactones), polylysine, poly(ethylene imine), poly (acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In certain embodiments, copolymers may contain poly (ester-ether)s, e.g., polymers having repeat units joined by ester bonds (e.g., R—C(O)—O—R' bonds) and ether bonds (e.g., R—O—R' bonds). In some embodiments, the nanoparticle may further include a polymer able to reduce immunogenicity, for example, a poly(alkylene glycol) such as poly(ethylene glycol) ("PEG"). The amount of PEG in the nanoparticle should be limited however, so as not to substantiality compromise the tunability of the nanoparticles, which is enhanced by selection of a polymer with a backbone having multiple functional groups per monomer unit, such as a polysaccharide, as compared to PEG which has only reactive functional group per polymer chain. In some embodiments, the nanoparticle composition is free of PEG.

The hydrophobic portion of the macromolecule generally comprises a hydrophobic polymer, for example, a hydrophobic polymer selected from polyesters, polyorthoester, polycarbonates, polyimides, polybenzimidazoles, polyurethanes, polyureas, polysulfides, polyethers, polysulfones, phenolic and amino plastics, chitin and lipopolysaccharides, cholesterol, proteoglycans, and combinations thereof. In an aqueous environment, e.g. under physiological conditions, the hydrophobic portion will substantially form the core of the nanoparticle.

In some embodiments, the hydrophobic portion of the macromolecule comprises a biocompatible polymer, for example, selected from polylactide (PLA), polyglycolide (PGA), poly(lactide-co-glycolide) (PLGA), poly(ε-caprolactone) (PCL), and combinations thereof. Such polymers are also biodegradable. In a PLGA polymer, the ratios of lactide to glycolide may be varied. In some embodiments, the hydrophobic portion of the macromolecule comprises polylactide (PLA). In some embodiments, the hydrophobic portion of the macromolecule comprises polyglycolide (PGA). In some embodiments, the hydrophobic portion of the macromolecule comprises poly(lactide-co-glycolide) (PLGA). In some embodiments, the hydrophobic portion of the macromolecule comprises poly(ε-caprolactone) (PCL).

In some embodiments, the hydrophobic portion is a polymer comprising 2 or more repeat units. The hydrophilic portion may comprise, for example, from 2 to 200,000 repeat units depending on the size of the hydrophobic portion desired.

In some embodiments, the molecular weight of the hydrophobic portion is in the range of about 100 g/mol to about 2,000,000 g/mol. In some embodiments, the molecular weight of the hydrophobic portion is in the range of about 500 g/mol to about 200,000 g/mol. In some embodiments, the molecular weight of the hydrophobic portion is in the range of about 1,000 g/mol to about 100,000 g/mol. The unit "g/mol" in this case refers to the weight of the hydrophobic portion per mol of the macromolecule prior to conjugation with a targeting moiety.

In some embodiments, the molecular weight of the hydrophobic portion is about 0.1 kDa to about 2000 kDa. In some embodiments, the molecular weight of the hydrophobic portion is about 0.5 kDa to about 200 kDa. In some embodiments, the molecular weight of the hydrophobic portion is about 1 kDa to 100 kDa. These values represent ranges prior to conjugation with a targeting moiety.

The hydrophilic portion of the macromolecule generally comprises a polymer having multiple reactive functional groups capable of being coupled to a targeting moiety. For example, the polymer may comprise a backbone made up of multiple monomer units, each monomer unit having multiple functional groups available for conjugation to a targeting moiety. Each monomer unit may, for example, have 2, 3, 4 or 5 functional groups. In some embodiments, each monomer unit has 4 functional groups. The functional groups may, for example, be independently selected from OH groups, thiol groups, ketone groups, amine groups, and carboxylic acid groups, among others. For example, a sugar moiety in a dextran polymer may have 4 OH groups available for conjugation to a targeting moiety (see Scheme 1).

The proportion of functional moieties conjugated to a targeting moiety can be controlled to effect targeting. In some embodiments, at least 10%, 20%, 30%, 40%, 50%, 60%, 70%, 80%, 90%, 95%, 98%, 99% or 100% of the functional moieties on the surface of the nanoparticle are conjugated to a targeting moiety.

The selection of a hydrophilic polymer having multiple functional moieties per monomer unit allows for enhanced tunability of the nanoparticles as compared to, for example, conventional PEG-based nanoparticles having only one reactive functional group at the terminal end of each PEG chain. Furthermore, in some embodiments, the hydrophilic polymers of the present disclosure are more hydrophilic than a PEG polymer such that the hydrophilic portion of the macromolecule is less likely to orient toward the core of the nanoparticle during nanoparticle formation. Since the targeting moieties will typically be conjugated to the hydrophilic portion, this results in a nanoparticle wherein substantially all of the targeting moiety is on the surface of the nanoparticle) for targeting. In such embodiments, the core of the nanoparticle is substantially free of targeting moiety (i.e. substantially no targeting moiety in the core of the nanoparticle.

In some embodiments, the hydrophilic portion of the macromolecule having multiple functional groups comprises a polymer selected from a polysaccharide, a polynucleotide, a polypeptide, or a combination thereof. The polysaccharide, polynucleotide, or polypeptide may be based on naturally-occurring monomers, or derivatives or analogues thereof. Such derivatives and analogues are known to those skilled in the art and can be readily obtained or synthesized. In some embodiments, polysaccharides, for example, dextran, are preferred since there are multiple functional groups per each monomer unit.

In some embodiments, the hydrophilic portion of the macromolecule comprises a "polysaccharide", e.g. a polymer of monosaccharide units joined together by glycosidic linkages. Any suitable polysaccharide may be used accordance with the present disclosure. In some embodiments, the polysaccharide is composed of 4- to 8-carbon ring monomers, such as 5-carbon ring monomers. The monomer rings may be heterocyclic, form example, comprising one or more N, O or S atoms in the monomer ring. The polysaccharide may be a "homopolysaccharide", where all of the monosaccharides in the polysaccharide are the same type, or a "heteropolysaccharide", where more than one type of monosaccharide is present. In some embodiments, the polysaccharide is a "homopolysaccharide". In some embodiments, the polysaccharide is a "heteropolysaccharide". In some embodiments, the polysaccharide is a linear polysaccharide. In some embodiments, the polysaccharide is a branched polysaccharide. In some embodiments, the polysaccharide has a reducing end that can be modified for conjugation purposes. In some embodiments, the polysaccharide is a homopolysaccharide with a reducing end.

In some embodiments, the polysaccharide is composed of monomers of glucose, fructose, lactose or a combination thereof.

In some embodiments, the polysaccharide is selected from dextran, chitosan, alginate, hyaluronic acid, heparin, chondroitin sulphate, pectin, pullulan, amylose, cyclodextrin, carboxymethylcellulose or a polysaccharide with thiol functional groups conjugated to the polymer backbone.

In some embodiments, the polysaccharide is dextran, alginate, hyaluronic acid, chitosan, cyclodextrin, or carboxymethylcellulose. In some embodiments, the polysaccharide is dextran.

In some embodiments, the hydrophilic portion comprises a polynucleotide, e.g. a polymer of nucleotides. As used herein, a "nucleotide" refers to a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide may be, for example, ribose sugars (a "ribonucleic acid," or "RNA"), or deoxyribose sugars (a "deoxyribonucleic acid," or "DNA"). In some cases, the polymer may comprise both ribose and deoxyribose sugars. Examples of bases include, but not limited to, the naturally-occurring bases (e.g., adenosine or "A," thymidine or "T," guanosine or "G," cytidine or "C," or uridine or "U"). The nucleotide may be a naturally-occurring nucleotide or a derivative or analog thereof. Several derivatives and analogs are known to those skilled in the art.

In some embodiments, the hydrophilic portion comprises a polypeptide, e.g. a polymer of amino acids. The amino acid may be a naturally-occurring amino acid or a derivative or analog thereof. Several derivatives and analogs are known to those skilled in the art. In some embodiments, at least a portion (e.g. greater than 50%, 60%, 70%, 80%, 90%, 95%, 98%, 99%, 100%) of the nucleotides in the polynucleotide have side chains with reactive functional groups capable of being conjugated to the targeting moiety.

In some embodiments, the hydrophilic portion is a polymer comprising 2 or more repeat units. The hydrophilic portion may comprise, for example, 2 to 100,000 repeat units depending on desired size of the nanoparticle.

In some embodiments, the molecular weight of the hydrophilic portion ranges from about 100 g/mol to about 1,000,000 g/mol. In some embodiments, the molecular weight of the hydrophilic portion ranges from about 500 g/mol to 100,000 g/mol. In some embodiments, the molecular weight of the hydrophilic portion ranges from about 1,000 g/mol to about 50,000 g/mol. The unit "g/mol" in this case refers to the weight of the hydrophilic portion per mol of the macromolecule prior to conjugation with a targeting moiety.

In some embodiments, the molecular weight of the hydrophilic portion ranges from about 0.1 kDa to about 1,000 kDa. In some embodiments, the molecular weight of the hydrophilic portion ranges from about 0.5 kDa to 100 kDa. In some embodiments, the molecular weight of the hydrophilic portion ranges from about 1 kDa to 50 kDa. These values represent ranges prior to conjugation with a targeting moiety.

The relative amount of hydrophobic polymer to hydrophilic polymer in the macromolecule may be any suitable ratio that provides the desired characteristics of the resulting nanoparticle. In some embodiments, the molecular weight of the hydrophobic portion is larger than the molecular weight of the hydrophilic portion. In some embodiments, the molecular weight of the hydrophilic portion is larger than the molecular weight of the hydrophobic portion.

In some embodiments, the ratio of the molecular weight of the hydrophobic portion to the hydrophilic portion (hydrophobic portion:hydrophilic portion) is a about 0.1:1 to 100:1. In some embodiments, the molecular weight ratio is about 0.5:1 to about 50:1. In some embodiments, the molecular weight ratio is about 1:1 to about 10:1. In some embodiments, the molecular weight ratio is about 1:1 to about 5:1, about 1:1 to about 4:1, about 1:1 to about 3:1, or about 1:1 to about 2:1. In some embodiments, the molecular weight ratio is about 5:1, 4:1, 3:1, 2:1, 1:1, 1:2, 1:3, 1:4 or 1:5. These values prepresent ratios before conjugation of the targeting moiety. A skilled person will be able to determine a suitable ratio based on the particular polymers selected and the agent of interest to be encapsulated.

Targeting

The macromolecules described herein are conjugated to a targeting moiety, such that the targeting moiety located on the surface of the nanoparticle when the nanoparticle is formed to thereby surface-functionalize nanoparticle. The interaction between the targeting moiety and a target at the mucosal site directs the nanoparticle to a particular site and/or increases the retention time of the nanoparticle at a particular site compared to a nanoparticle with no targeting moiety. Any suitable targeting moiety may be selected. Examples of targeting moieties include, but are not limited to, small molecules, polynucleotides, polypeptides, polysaccharides, fatty acids, lipids, and antibodies.

The targeting moiety may be a mucosal targeting moiety. As used herein, a "mucosal targeting moiety" is a targeting moiety capable of binding to a target expressed at the mucosal site. In some embodiments, the nanoparticles may comprise more than one type of mucosal targeting moiety. For example, an individual macromolecule may be functionalized with two or more different targeting moieties, or the nanoparticle may be formed from two or more macromolecules, each being functionalized with a different targeting moiety.

The term "binding," as used herein, refers to the interaction between a corresponding pair of molecules or portions thereof that exhibit mutual affinity or binding capacity, typically due to specific or non-specific binding or interaction, including, but not limited to, biochemical, physiological, electrostatic and/or chemical interactions. In some cases, the targeting moiety is able to selectively bind to a target expressed at the mucosal site, for example, a molecule, receptor or residue expressed at the mucosal site. "Selective binding", as used herein, refers to a targeting moiety, which may be a small molecule or a large molecule, that is able to preferentially bind to or recognize a particular target or subset of targets, to a substantially higher degree than to others. The target may, for example, be a biological substrate that is preferentially expressed at the mucosal site, such as mucin or a receptor or a glycoprotein or a polysaccharide or residue expressed on the surface of an epithelial cell. In some cases, the binding is a high affinity binding the binding, such as covalent bonding, van der Waal force or hydrogen bonding. Preferably, the binding is covalent binding. For example, in some cases, the target may possess functional groups reactive with the targeting moiety and in a particular configuration that permits covalent binding of the targeting moiety.

In some embodiments, the targeting moiety is capable of binding to carbohydrate residues that contain cis-diol groups, for example, galactose, N-acetylgalactosamine, N-acetyl-glucosamine, fucose, and sialic acids. Such carbohydrate residues may, for example, be present on mucin. In some embodiments, the carbohydrate residue is a sialic acid residue. In some embodiments, the targeting moiety is a boronic acid derivative capable of binding a cis-diol group on a sialic acid residue. In some embodiments, the targeting moiety is a phenylboronic acid (PBA) derivative.

In some embodiments, the targeting moiety is a thiol derivative or an acrylate derivative capable of binding to thiol groups of cysteine moieties. Cysteine moieties may, for example, be present on mucin. In some embodiments, the targeting moiety is a thiol derivative, such as cysteamine. In some embodiments, the targeting molecule may be cysteamine derivative capable of forming a disulfide linkage with a cysteine moiety on the mucous membrane. In some embodiments, the targeting moiety is an acrylate derivative capable of binding to hydroxyl groups of the glycoproteins on the mucous membrane. Acrylate derivatives include, but are not limited to methacrylate, ethyl acrylate, and diacrylate. In some embodiments, the targeting moiety is an acrylate derivative selected from methacrylate, ethyl acrylate, and diacrylate.

In some embodiments, the targeting moiety is a phenylboronic acid (PBA) derivative, a thol derivative or an acrylate derivative.

In some embodiments, the targeting moiety is the hydrophobic portion of the macromolecule comprises PLA; the hydrophilic portion comprises dextran; and the targeting moiety comprises PBA. In some embodiments, the targeting moiety is the hydrophobic portion is PLA; the hydrophilic portion is dextran, and the targeting moiety is PBA.

In some embodiments, the targeting moiety is a biological moiety. Non-limiting examples of biological moieties include a peptide, a protein, an enzyme, a nucleic acid, a fatty acid, a hormone, an antibody, a carbohydrate, a peptidoglycan, a glycopeptide, or the like. In some cases, the biological moiety may be relatively large, for example, for peptides, nucleic acids, or the like. For example, the biological moiety may have a molecular weight of at least about 1,000 Da, at least about 2,500 Da, at least about 3000 Da, at least about 4000 Da, or at least about 5,000 Da, etc. Relatively large targeting moieties may be useful, in some cases, for differentiating between cells. For instance, in some cases, smaller targeting moieties (e.g., less than about 1000 Da) may not have adequate specificity for certain targeting applications, such as mucosal targeting applications. In contrast, larger molecular weight targeting moieties can offer a much higher targeting affinity and/or specificity. For example, a targeting moiety may offer smaller dissociation constants, e.g., tighter binding. However, in other embodiments, the targeting moiety may be relatively small, for example, having a molecular weight of less than about 1,000 Da or less than about 500 Da.

Nanoparticles

Another aspect of the disclosure is directed to nanoparticles formed generally from the association of macromolecules, such as the macromolecules described above. The nanoparticles demonstrated effective targeting and adhesion, as well as sustained release of payload at the mucosal site.

Under appropriate conditions, the macromolecules are capable of assembling to form a nanoparticle of the core-shell type, where the core of the nanoparticle is relatively hydrophobic in comparison to the shell. Alternatively, under different conditions, the core of the nanoparticle may be relatively hydrophilic in comparison to the shell. The shell provides a surface of the nanoparticles, which may comprise a targeting moiety at a desired surface density, such that the nanoparticles are coated with the targeting moiety.

The nanoparticles may have a substantially spherical shape (i.e., the particles generally appear to be spherical). Such nanoparticles may also be referred to as "nanospheres" or "nanovesicles" due to their generally spherical shape and the formation of a cavity within the nanoparticle. It will be understood that the particles, for example, upon swelling or shrinkage, may adopt a non-spherical configuration.

The nanoparticles formed have an average particle size of less than about 1000 nm (1 micrometer). In some embodiments, the average particle size is less than about 500 nm, less than about 300 nm, less than about 200 nm, less than about 150 nm, less than about 100 nm, less than about 50 nm, less than about 30 nm, less than about 10 nm, less than about 3 nm, or less than about 1 nm in some cases. In some cases, particles less than 150 mn are preferred, for example, such particles are better able to penetrate the tear layer of the eye compared to larger particles.

In some embodiments, the average particle size is between about 0.1 nm and about 1000 nm, about 1 nm and about 500 nm, about 1 nm and about 300 nm, about 1 nm and about 200 nm, about 1 nm and about 150 nm, about 1 nm and about 100 nm, about 1 nm and about 50 nm, about 10 nm and about 150 nm, about 10 nm and about 100 nm, about 10 nm and about 75 nm, about 10 nm and about 60 nm, and about 10 nm and about 50 nm, or about 20 and about 40 nm.

As used herein, "particle size" refers to the average characteristic dimension of a population of nanoparticles formed, where the characteristic dimension of a particle is the diameter of a perfect sphere having the same volume as the particle. A population of nanoparticles may, for example, include at least 20 particles, at least 50 particles, at least 100 particles, at least 300 particles, at least 1,000 particles, at least 3,000 particles, at least 5,000 particles, at least 10,000 particles, or at least 50,000 particles. Various embodiments of the present invention are directed to such populations of particles.

In some embodiments, the particles may each be substantially the same shape and/or size, in which case the population is "monodisperse". For example, the particles may have a distribution of particle sizes such that no more than about 5% or about 10% of the particles have a particle size greater than about 10% greater than the average particle size of the particles, and in some cases, such that no more than about 8%, about 5%, about 3%, about 1%, about 0.3%, about 0.1%, about 0.03%, or about 0.01% have a particle size greater than about 10% greater than the average particle size of the particles. In some cases, no more than about 5% of the particles have a particle size greater than about 5%, about 3%, about 1%, about 0.3%, about 0.1%, about 0.03%, or about 0.01% greater than the average particle size of the particles.

In some embodiments, the particles have an interior core and an exterior shell which forms the surface of the nanoparticle, where the shell has a composition different from the core i.e., there may be at least one polymer or moiety present in shell but not in the core (or vice versa), and/or at least one polymer or moiety present in the core and/or the shell at differing concentrations.

In some cases, the core of the particle is more hydrophobic than the shell of the particle. In some cases, a drug or other payload may be hydrophobic, and therefore readily associates with the relatively hydrophobic interior of the particle. The drug or other payload may thus be contained within the interior of the particle, which may thus shelter it from the external environment surrounding the particle (or vice versa). A targeting moiety present on the surface of the particle may allow the particle to become localized at a particular targeting site, for instance, a mucosal site. The drug or other payload may then, in some cases, be released from the particle and allowed to interact with the particular targeting site.

Yet another aspect of the disclosure is directed to nanoparticles having more than one polymer or macromolecule present. For example, in some embodiments, particles may contain more than one distinguishable macromolecule, and the ratios of the two (or more) macromolecules may be independently controlled, which allows for the control of properties of the particle. For instance, a first macromolecule may be a biocompatible polymeric conjugate, such as a block copolymer, comprising a targeting moiety, and a second macromolecule may comprise a biocompatible polymer but no targeting moiety, or the second macromolecule may contain a distinguishable biocompatible polymer from the first macromolecule. Control of the amounts of these macromolecules within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

Tunable Nanoparticles

The nanoparticles described herein are highly tunable.

For example, the size of the nanoparticles can be tuned by adjusting the molecular weight and/or composition of the hydrophobic portion and/or the hydrophilic portion. The particular targeting moiety selected, as well as the surface density of the targeting moiety on the surface of the nanoparticles, will also impact the particle size.

It should be noted that increasing size of the hydrophilic and/or hydrophobic polymer components does not always result in a larger particle size. For example, in some cases, longer polymer chains may be more flexible and capable of folding to produce a more compact particle whereas a shorter polymer chain may be confined to a more linear configuration. Selection of a branched versus a linear polymer can also impact particle size. A skilled person will be able to select suitable polymers for a particular application.

The hydrophilic potion of the macromolecules will form the shell of the nanoparticles in an aqueous environment. The hydrophilic portion is selected such that it has multiple functional moieties for conjugation to a targeting moiety. The proportion of functional moieties conjugated to a targeting moiety can be controlled, at least in part, by the amount of targeting moiety added to the conjugation reaction. In general, the more functional moieties present on the hydrophilic portion, the higher the degree of tunability of the nanoparticles. In general, the nanoparticles disclosed herein are thus more tunable than PEG-based nanoparticles having only one functional moiety per PEG chain, or other similar polymers.

By adjusting the surface density of the targeting moiety, the extent of targeting can be controlled. A high surface density of the targeting moiety can be achieved with the nanoparticles disclosed herein due to the presence of multiple functional moieties on the hydrophilic portion. Advantageously, a skilled person will be able to control the extent of targeting without substantially compromising the stability of the nanoparticle delivery system. In some embodiments, an optimal density can be determined in which maximum targeting is achieved without substantially compromising the stability of the nanoparticle.

In some embodiments, a majority (e.g. at least 50%, 60%, 70%, 80%, 90%, 95%, 98%, 99%, or 100%) of the mucosal targeting moieties are located on the surface of the nanoparticle. It is understood that, in some cases, a portion of the mucosal targeting moieties may be located within the core of the nanoparticle when the nanoparticle forms, depending on the components of the nanoparticle and the method utilized. For instance, where a one-step method is used, it is possible that some of the targeting moieties may orient toward the core of the particles.

The selection of a hydrophilic polymer having multiple functional moieties along the polymer backbone renders the hydrophilic portion of the molecule more hydrophilic than other polymers, such as PEG, thus the hydrophilic portion is more likely to orient toward an aqueous environment. Since the targeting moiety is conjugated to the hydrophilic portion, typically after formation of a nanoparticle, substantially all of the targeting moieties are located on the surface of the nanoparticle as opposed to the core.

In some embodiments, substantially all (e.g. at least 95%, 96%, 97%, 98%, 99%, or 100%) of the mucosal targeting moieties are located on the surface of the nanoparticle. Localizing substantially all of the targeting moieties to the surface of the nanoparticles enhances targeting efficiency. The selection of a hydrophilic polymer having multiple functional moieties along the polymer backbone renders the hydrophilic portion of the molecule more hydrophilic than other polymers, such as PEG having only one functional moiety, thus the hydrophilic portion is more likely to orient toward an aqueous environment. Since the targeting moiety is conjugated to the hydrophilic portion, typically after formation of a nanoparticle, substantially all of the targeting moieties are located on the surface of the nanoparticle as opposed to the core.

The nanoparticles can be tuned by controlling the surface density of the targeting moieties on the nanoparticle. A skilled person will be able to precisely tune the nanoparticle for a particular application without substantially compromising the stability of the nanoparticles.

In some embodiments, the surface density of the targeting moiety is about 1 per $nm^2$ to 15 per $nm^2$, about 1 per $nm^2$ to 10 per $nm^2$, about 1 per $nm^2$ to 5 per $nm^2$, about 1 per $nm^2$ to about 15 per $nm^2$, about 3 per $nm^2$ to about 12 per $nm^2$, or from about 5 per $nm^2$ to about 10 per $nm^2$.

In some embodiments, the surface density of the targeting moiety is about 1, 2, 3, 4, 5, 6, 7, 8, 8, 9, 11, 12, 13, 14 or 15 per $nm^2$.

In some embodiments, the nanoparticle is approximately 10 nm in size and the density of targeting moieties on the surface of the nanoparticle (i.e. surface density) ranges from about 50 to about 3,500, from about 500 to about 3500, or from about 1000 to about 3500 per nanoparticle.

In some embodiments, the nanoparticle is approximately 30 nm in size and the density of targeting moieties on the surface of the nanoparticle (i.e. surface density) ranges from about 50 to about 30000, from about 1000 to about 30000, or from about 10000 to about 30000 per nanoparticle.

In some embodiments, the nanoparticle is approximately 50 nm in size and the density of targeting moieties on the surface of the nanoparticle (i.e. surface density) ranges from about 50 to about 90000, from about 3000 to about 90000, or from about 30000 to about 90000 per nanoparticle.

In some embodiments, the nanoparticle is approximately 100 nm in size and the density of targeting moieties on the surface of the nanoparticle (i.e. surface density) ranges from about 50 to about 350000, from about 10000 to about 350000, or from about 100000 to about 350000 per nanoparticle.

In some embodiments, the nanoparticle is approximately 150 nm in size and the density of targeting moieties on the surface of the nanoparticle (i.e. surface density) ranges from about 50 to about 800000, from about 30000 to about 800000, or from about 300000 to about 800000 per nanoparticle.

In some embodiments, the nanoparticle is approximately 200 nm in size and the density of targeting moieties on the surface of the nanoparticle (i.e. surface density) ranges from about 50 to about 1,500,000, from about 60000 to about 1,500,000, or from about 600000 to about 1,500,000 per nanoparticle.

In some embodiments, the nanoparticle is approximately 250 nm in size and the density of targeting moieties on the surface of the nanoparticle (i.e. surface density) ranges from about 50 to about 2,500,000, from about 100,000 to about 2,500,000, or from about 1,000,000 to about 2,500,000 per nanoparticle.

In some embodiments, the nanoparticle is approximately 300 nm in size and the density of targeting moieties on the surface of the nanoparticle (i.e. surface density) ranges from about 50 to about 3,500,000, from about 150,000 to about 3,500,000, or from about 1,500,000 to about 3,500,000 per nanoparticle.

In some embodiments, the surface density of the targeting moiety tunable by the amount of targeting moiety added in the reaction during the functionalization step(s).

In some embodiments, the density of a phenylboronic acid derivative on the nanoparticle surface is tuneable by the amount of phenylboronic acid added in the reaction to control the extent of mucoadhesion properties of the nanoparticles.

In some embodiments, the density of a cysteamine derivative on the nanoparticle surface is tuneable by the amount of cysteamine derivative added in the reaction to control the extent of mucoadhesion properties of the nanoparticles.

In some embodiments, the density of an acrylate derivative on the nanoparticle surface is tuneable by the amount of acrylate derivative added in the reaction to control the extent of mucoadhesion properties of the nanoparticles.

The optimal density of surface functional groups may be determined by those skilled in the art in order to achieve balance between the extent of mucoadhesion and the colloidal stability of the nanoparticles.

In some embodiments, the nanoparticles are dispersed in aqueous medium. The aqueous medium may, for example, be a physiologically compatible aqueous medium.

Controlled Release

A controlled release system, as used herein, refers to a nanoparticle delivery system capable of delivering a payload, such as a therapeutic agent, a diagnostic agent, a prognostic, a prophylactic agent, to a body tissue, such as a mucous membrane, where the payload is released in a predesigned or controlled manner. For example, the active agent may be released in a constant manner over a predetermined period of time, the active agent may be released in a cyclic manner over a predetermined period of time, or an environmental condition or external event may trigger the release of the active agent. The controlled release polymer system may include a polymer that is biocompatible, and in some cases, the polymer is biodegradable. In some cases, the nanoparticles disclosed herein are part of a controlled release delivery system. The nanoparticles disclosed herein demonstrated sustained release of payload.

The mucosal targeting moiety assists in retaining the nanoparticles at the mucosal site, i.e. for a longer time that the same nanoparticle without the targeting moiety, such that controlled delivery of a payload at the mucosal site can be achieved. The controlled delivery may include sustained delivery.

In some embodiments, in the payload is released from the nanoparticle for a sustained period of at least 24, 36, 48, 60, 72, 84, of 96 hours. In some embodiments, the payload is released from the nanoparticle for a sustained period of at least 1, 2, 3, 4, 5, 6, 7 or 8 days. In some embodiments, the payload is released is released from the nanoparticle for a sustained period of at least 1 week. In some embodiments, the payload is released is released from the nanoparticle for a sustained period of at least 1 month.

In some embodiments at least 50% of the payload is released within the first 24 hours. In other embodiments, at least 10% the payload is released within the first 6 hours.

Payload

A wide variety of payloads can be loaded into the nanoparticles described herein. As used herein, the "payload" may be any agent of interest to be delivered to a mucosal site, for example, a therapeutic agent (e.g. drug), a diagnostic agent, a prophylactic agent, an imaging agent, or a combination thereof. In some embodiments, the payload is a single agent of interest. In other embodiments, the payload comprises more than one agent of interest, for example, a combination of two or more agents of interest. In some embodiments, the payload comprises 2, 3 or 4 agents of interest. For example, the payload may comprise two or more agents of interest selected from a therapeutic agent, a diagnostic agent, a prophylactic agent, an imaging agent and combinations thereof.

When combined with a payload, the nanoparticles described herein are useful as a mucoadhesive nanoparticle delivery system for delivering the payload to a mucosal site. In some embodiments, the payload is predominantly encapsulated within the core of the nanoparticle. By "predominantly" it is meant that more than 60%, 70%, 80%, 90%, 95% or 99% of the payload is encapsulated within the core of the nanoparticle. It will be understood that, depending on the composition of the nanoparticle and the payload, a portion of the payload could also be distributed within the shell of the nanoparticle and/or on the surface of the nanoparticle.

In some embodiments, the payload comprises a hydrophobic agent. For example, the payload may be a hydrophobic therapeutic agent, a hydrophobic diagnostic agent, a hydrophobic prophylactic agent or a hydrophobic imaging agent. In one embodiment, the payload is a hydrophobic therapeutic agent. In one embodiment, the payload is a hydrophobic diagnostic agent. In one embodiment, the payload is a hydrophobic prophylactic agent. In one embodiment, the payload is a hydrophobic imaging agent. The encapsulation of hydrophobic compounds in the nanoparticles is due to the hydrophobic interaction between the hydrophobic agent and the hydrophobic portions of the copolymers that form the core of the nanoparticles.

In some embodiments, the payload comprises a hydrophilic agent. For example, the payload may be a hydrophilic therapeutic agent, a hydrophilic diagnostic agent, a hydrophilic prophylactic agent or a hydrophilic imaging agent. In one embodiment, the payload is a hydrophilic therapeutic agent. In one embodiment, the payload is a hydrophilic diagnostic agent. In one embodiment, the payload is a hydrophilic prophylactic agent. In one embodiment, the payload is a hydrophilic imaging agent. It will be understood that the composition of the nanoparticle would be modified to encapsulate a hydrophilic payload, for example, a triblock copolymer comprising a first hydrophilic block, and second hydrophobic block and a third hydrophilic block could be used. Such modifications are well known to those skilled in the art.

The nanoparticles described herein were found to have good loading capacity and efficiency. The loading capacity of various drugs using exemplary Dex-b-PLA (optionally surface functionalized with PBA) nanoparticles is demonstrated in the Examples. In some embodiments, the nanoparticles disclosed herein have higher loading capacity than reported for conventional PEG-based polymers. Naturally, loading capacity will be affected by the composition of the nanoparticles and the choice of payload.

In some embodiments, the loading capacity is in the range of about 1 to about 40% wt/wt, about 1 to about 30% wt/wt., about 1 to about 20%, 1 to about 10%, about 1% to about 8%, about 1% to about 6%, about 1% to about 5%, about 1% to about 3%, or about 1% to about 2%. The loading capacity (%) is calculated here as the molecular weight of encapsulated drug over the entire weight of the nanoparticle multiplied by 100. The total weight of the nanoparticle refers to the weight of the nanoparticle including the targeting moiety and the encapsulated drug.

In some embodiments, the loading capacity is up to about 40%, up to about 30% wt/wt., up to about 20%, up to about 10%, up to about 8%, up to about 6%, up to about 5%, up to about 3%, up to about 2%, or up to about 1%.

In some embodiments the payload has a molecular weight of about 0.001 kDa to 100 kDa, about 0.01 kDa to 50 kDa, about 0.1 kDa to 10 kDa.

In some embodiments, the payload has a diameter of about 0.01 nm to about 300 nm, about 0.01 nm to about 100 nm, about 0.01 nm to about 50 nm.

Non-limiting examples of potentially suitable therapeutic agents include antimicrobial agents, analgesics, antiinflammatory agents, IOP lowering agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic agents may be selected from contraceptives and vitamins as well as micro- and macronutrients. Still other examples include antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

Further non-limiting examples of drugs include timolol, betaxolol, metipranolol, dorzolamide, brinzolamide, neptazane, acetazolamide, alphagan, xalatan, bimatoprost, travaprost, olopatadine, ketotifen, acyclovir, gancyclovir, valcyclovir, doxorubicin, mitomycin, cisplatin, daunorubicin, bleomycin, actinomycin D, neocarzinostatin, carboplatin, stratoplatin, Ara-C. Other examples include Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb); Ceclor, Lorabid, Dynabac, Prozac, Darvon, Permax, Zyprexa, Humalog, Axid, Gemzar, Evista (Eli Lily); Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.); Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer); Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn); Lopid, Accrupil, Dilantin, Cognex, Neurontin, Loestrin, Dilzem, Fempatch, Estrostep, Rezulin, Lipitor, Omnicef, FemHRT, Suramin, or Clinafloxacin (Warner Lambert).

Further non-limiting examples of therapeutic agents that can be included within a particle of the present invention include acebutolol, acetaminophen, acetohydroxamic acid, acetophenazine, acyclovir, adrenocorticoids, allopurinol, alprazolam, aluminum hydroxide, amantadine, ambenonium, amiloride, aminobenzoate potassium, amobarbital, amoxicillin, amphetamine, ampicillin, androgens, anesthetics, anticoagulants, anticonvulsants-dione type, antithyroid medicine, appetite suppressants, aspirin, atenolol, atropine, azatadine, bacampicillin, baclofen, beclomethasone, belladonna, bendroflumethiazide, benzoyl peroxide, benzthiazide, benztropine, betamethasone, betha nechol, biperiden, bisacodyl, bromocriptine, bromodiphenhydramine, brompheniramine, buclizine, bumetanide, busulfan, butabarbital, butaperazine, caffeine, calcium carbonate, captopril, carbamazepine, carbenicillin, carbidopa & levodopa, carbinoxamine inhibitors, carbonic anhydsase, carisoprodol, carphenazine, cascara, cefaclor, cefadroxil, cephalexin, cephradine, chlophedianol, chloral hydrate, chlorambucil, chloramphenicol, chlordiazepoxide, chloroquine, chlorothiazide, chlorotrianisene, chlorpheniramine, 6× chlorpromazine, chlorpropamide, chlorprothixene, chlorthalidone, chlorzoxazone, cholestyramine, cimetidine, cinoxacin, clemastine, clidinium, clindamycin, clofibrate, clomiphere, clonidine, clorazepate, cloxacillin, colochicine, coloestipol, conjugated estrogen, contraceptives, cortisone, cromolyn, cyclacillin, cyclandelate, cyclizine, cyclobenzaprine, cyclophosphamide, cyclothiazide, cycrimine, cyproheptadine, danazol, danthron, dantrolene, dapsone, dextroamphetamine, dexamethasone, dexchlorpheniramine, dextromethorphan, diazepan, dicloxacillin, dicyclomine, diethylstilbestrol, diflunisal, digitalis, diltiazen, dimenhydrinate, dimethindene, diphenhydramine, diphenidol, diphenoxylate & atrophive, diphenylopyraline, dipyradamole, disopyramide, disulfuram, divalporex, docusate calcium, docusate potassium, docusate sodium, doxyloamine, dronabinol ephedrine, epinephrine, ergoloidmesylates, ergonovine, ergotamine, erythromycins, esterified estrogens, estradiol, estrogen, estrone, estropipute, etharynic acid, ethchlorvynol, ethinyl estradiol, ethopropazine, ethosaximide, ethotoin, fenoprofen, ferrous fumarate, ferrous gluconate, ferrous sulfate, flavoxate, flecamide, fluphenazine, fluprednisolone, flurazepam, folic acid, furosemide, gemfibrozil, glipizide, glyburide, glycopyrrolate, gold compounds, griseofiwin, guaifenesin, guanabenz, guanadrel, guanethidine, halazepam, haloperidol, hetacillin, hexobarbital, hydralazine, hydrochlorothiazide, hydrocortisone (cortisol), hydroflunethiazide, hydroxychloroquine, hydroxyzine, hyoscyamine, ibuprofen, indapamide, indomethacin, insulin, iofoquinol, iron-polysaccharide, isoetharine, isoniazid, isopropamide isoproterenol, isotretinoin, isoxsuprine, kaolin & pectin, ketoconazole, lactulose, levodopa, lincomycin liothyronine, liotrix, lithium, loperamide, lorazepam, magnesium hydroxide, magnesium sulfate, magnesium trisilicate, maprotiline, meclizine, meclofenamate, medroxyproyesterone, melenamic acid, melphalan, mephenyloin, mephobarbital, meprobamate, mercaptopurine, mesoridazine, metaproterenol, metaxalone, methamphetamine, methaqualone, metharbital, methenamine, methicillin, methocarbamol, methotrexate, methsuximide, methyclothinzide, methylcellulose, methyldopa, methylergonovine, methylphenidate, methylprednisolone, methysergide, metoclopramide, matolazone, metoprolol, metronidazole, minoxidil, mitotane, monamine oxidase inhibitors, nadolol, nafcillin, nalidixic acid, naproxen, narcotic analgesics, neomycin, neostigmine, niacin, nicotine, nifedipine, nitrates, nitrofurantoin, nomifensine, norethindrone, norethindrone acetate, norgestrel, nylidrin, nystafin, orphenadrine, oxacillin, oxazepam, oxprenolol, oxymetazoline, oxyphenbutazone, pancrelipase, pantothenic acid, papaverine, para-aminosalicylic acid, paramethasone, paregoric, pemoline, penicillamine, penicillin, penicillin-v, pentobarbital, perphenazine, phenacetin, phenazopyridine, pheniramine, phenobarbital, phenolphthalein, phenprocoumon, phensuximide, phenylbutazone, phenylephrine, phenylpropanolamine, phenyl toloxamine, phenyloin, pilocarpine, pindolol, piper acetazine, piroxicam, poloxamer, polycarbophil calcium, polythiazide, potassium supplements, pruzepam, prazosin, prednisolone, prednisone, primidone, probenecid, probucol, procainamide, procarbazine, prochlorperazine, procyclidine, promazine, promethazine, propantheline, propranolol, pseudoephedrine, psoralens, syllium, pyridostigmine, pyrodoxine, pyrilamine, pyrvinium, quinestrol, quinethazone, uinidine, quinine, ranitidine, rauwolfia alkaloids, riboflavin, rifampin, ritodrine, alicylates, scopolamine, secobarbital, senna, sannosides a & b, simethicone, sodium bicarbonate, sodium phosphate, sodium fluoride, spironolactone, sucrulfate, sulfacytine, sulfamethoxazole, sulfasalazine, sulfinpyrazone, sulfisoxazole, sulindac, talbutal, tamazepam, terbutaline, terfenadine, terphinhydrate, teracyclines, thiabendazole, thiamine, thioridazine, thiothixene, thyroblobulin, thyroid, thyroxine, ticarcillin, timolol, tocamide, tolazamide, tolbutamide, tolmetin trozodone, tretinoin, triamcinolone, trianterene, triazolam, trichlormethiazide, tricyclic antidepressants, tridhexethyl, trifluoperazine, triflupromazine, trihexyphenidyl, trimeprazine, trimethobenzamine, trimethoprim, tripclennamine, triprolidine, valproic acid, verapamil, vitamin A, vitamin B12, vitamin C, vitamin D, vitamin E, vitamin K, xanthine, and the like.

As another example, if the targeting moiety targets a cancer cell, then the payload may be an anti-cancer drug such as 20-epi-1,25 dihydroxyvitamin D3,4-ipomeanol, 5-ethynyluracil, 9-dihydroxtaxol, abiraterone, acivicin, aclarubicin, acodazole hydrochloride, acronine, acylfulvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, anti-dorsalizing morphogenetic protein-1, antiestrogen, antineoplaston, antisense oligonucleotides, aphidicolin glycinate, apoptosis gene modulators, apoptosis regulators, apurinic acid, ARA-CDP-DL-PTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisaziridinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caracemide, carbetimer, carboplatin, carboxamide-amino-triazole, carboxyamidotriazole, carest M3, carmustine, carn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethylnorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocarmycin SA, ebselen, ecomustine, edatrexate, edelfosine, edrecolomab, eflornithine, eflornithine hydrochloride, elemene, elsamitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ilmofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iododoxorubicin, iproplatin, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide 7, lobaplatin, lombricine, lometrexol, lometrexol sodium, lomustine, lonidamine, losoxantrone, losoxantrone hydrochloride, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, O6-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazofurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine; ribozymes, RII retinamide, RNAi, rogletimide, rohitukine, romurtide, roquinimex, rubiginone B1, ruboxyl, safingol, safingol hydrochloride, saintopin, sarcnu, sarcophytol A, sargramostim, SDI 1 mimetics, semustine, senescence derived inhibitor 1, sense oligonucleotides, signal transduction inhibitors, signal transduction modulators, simtrazene, single chain antigen binding protein, sizofuran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine, vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride. In one embodiment, the therapeutic agent is doxorubicin.

In some embodiments, the therapeutic agent is an agent used for treating or preventing a disease or condition that affects the eye (e.g. an ophthalmic agent). Non-limiting examples of ophthalmic agents include lubricants, demulcents, antibiotics, antivirals (e.g. acyclovir, gancyclovir, valcyclovir), antiallergic agents (e.g. antihistamine, e.g. olopatadine), IOP lowering agents, counterirritants, acetazolamide, alphagan, antazoline, aspirin, atropine, azelastine, bacitracin, betaxolol, bimatoprost, botanical drugs including zeaxanthine lutein, lycopene brimonodine, brinzolamide, carbachol, carteolol, ciprofloxacin, ofloxacin, cromalyn, cyclosporine (including cyclosporine prodrugs and cyclosporine derivatives), other immunomodulators, dapiprazole, dexamethasone, diclofenac, dipivifren, dorzolamide, epinephrine, erythromycin, fluorometholone, flurbiprofen, gentamycin, glaucoma medications (e.g. prostaglandins, carbonic anhydrase inhibitors, epinephrine or alpha-agonists, beta-blockers), gramicidin, homatropine, hydrocortisone, hyoscine, keterolac, ibuprofen, ketotifen, latanaprost, levobunolol, levocabastine, levofloxin, lotepprednol, medrysone, methazolamide, metipranolol, naphazoline, natamycin, nedocromil, neomycin, neptazane, neuroprotective agents, nonsteroidal anti-inflammatory agents, nepafanec, norfloxacin, ofloxacin, olopatadine, oxymetazoline, pemirolast, pheniramine, phenylephrine, pilocarpine, povidone, prednisolone, proparacaine, scopolamine, tetracaine, steroids, sulfacetamide, tetrahydrozoline, hypertonic tears, timolal, tobramycin, travaprost, trifluridine, trimethiprim, tropicamide, unoprostone, xalatan, and zinc. Prodrugs and related compounds, as well as new active pharmaceutical ingredients can be used with the delivery system described herein.

In one embodiment, the therapeutic agent is an ophthalmic agent selected from cycloprorin A, timolol, betaxolol, metipranolol, dorzolamide, brinzolamide, natamycin, neptazane, acetazolamide, alphagan, xalatan, bimatoprost, travaprost, olopatadine, ketotifen, acyclovir, gancyclovir, valcyclovir. In one embodiment, the therapeutic agent is cyclosporine A, natamycin, olopatadine, brinzolamide or dorzolamine.

In one embodiment, the therapeutic agent is an ophthalmic agent used to treat glaucoma, such as an agent used to reduce a sign and/or symptom of glaucoma, for example, and agent used to reduce intraocular pressure associated with ocular hypertension. In some embodiments, the therapeutic agent is a glaucoma medication, such as a prostaglandin, carbonic anhydrase inhibitor, epinephrine or alpha-agonist, or a beta-blocker. In some embodiments, the therapeutic agent is Dorzolamide, Brinzolamide, Brimonidine, timolol, or latanoprost.

In one embodiment, the therapeutic agent is an ophthalmic agent used to treat allergic conjunctivitis, such as an agent used to reduce a sign and/or symptom of allergic conjunctivitis. In one embodiment, the therapeutic agent is olopatadine.

In one embodiment, the therapeutic agent is an ophthalmic agent used to treat keratoconjunctivitis sicca (KCS) or "dry eye", such as an agent used to reduce a sign and/or symptom of KCS. In one embodiment, the therapeutic agent is cyclosporine A.

In one embodiment, the therapeutic agent is cyclosporine A. In one embodiment, the therapeutic agent is dorzolamide. In one embodiment, the therapeutic agent is natamycin. In one embodiment, the therapeutic agent is olopatadine.

In some embodiments, the therapeutic agent is an antibiotic, for example, a fluoroquinolone, vancomycin, cephalosporin, gentamycin, erythromycin, azithromycin, a sulfa drug, bacitracin, gatifloxacin, levofloxin, moxifloxacin, or ofoxacin.

In some embodiments, the therapeutic agent is an antiviral, for example, acyclovir, gancyclovir, valcyclovir.

In some embodiments, the therapeutic agent is an antiallergy agent, for example, an antihistamine. In one embodiment, the therapeutic agent is olopatadine.

In some embodiments, the nanoparticle composition comprising the therapeutic agent is administered to the anterior surface of the eye.

In some embodiments, the ophthalmic agent is formulated in a dosage form for administration to the eye surface, such as a drop, ointment or gel. In some embodiments, the ophthalmic agent is formulated in a dosage form for administration to the eye via a contact lens.

Diagnostic Agent

In another embodiment, the payload is a diagnostic agent. For example, the payload may be a fluorescent molecule; a gas; a metal; a commercially available imaging agent used in positron emissions tomography (PET), computer assisted tomography (CAT), single photon emission computerized tomography, x-ray, fluoroscopy, and magnetic resonance imaging (MRI); or a contrast agents. Non-limiting examples of suitable materials for use as contrast agents in MRI include gadolinium chelates, as well as iron, magnesium, manganese, copper, and chromium. Examples of materials useful for CAT and x-ray imaging include, but are not limited to, iodine-based materials.

Radionucleotide

As another example, the payload may include a radionuclide, e.g., for use as a therapeutic, diagnostic, or prognostic agent. Among the radionuclides used, gamma-emitters, positron-emitters, and X-ray emitters are suitable for diagnostic and/or therapy, while beta emitters and alpha-emitters may also be used for therapy. Suitable radionuclides for use with various embodiments of the present invention include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, or $^{18}$F. The radionucleotide may be contained within the nanoparticle (e.g., as a separate species), and/or form part of a macromolecule or polymer that forms the nanoparticle.

Pharmaceutical Compositions

Another aspect of the disclosure is related to pharmaceutical compositions comprising a nanoparticle composition as defined herein, and a pharmaceutically acceptable carrier. Pharmaceutical compositions can be prepared in a manner well known in the pharmaceutical art, and can be administered by a variety of routes of administration, depending upon whether local or systemic effect is desired and upon the area to be treated.

In some embodiments, the pharmaceutical composition is administered to a desired mucosal site in a subject. The pharmaceutical composition can be administered to a desired mucosal site by any suitable route of administration. In some embodiments, the route of administration is non-parenteral, such as topical. As used herein, topical administration may include, for example, administration to a mucous membrane via the mouth, eye, ear, nose, esophagus, stomach, small intestine, large intestine, rectum, vagina, urethra, penis, uterus, etc. It is understood that administration of a therapeutic agent to a mucosal site may provide local and/or systemic effect, for example, depending on the ability of the agent to be absorbed into the circulation via the mucous membrane.

Pharmaceutical compositions and formulations for topical administration generally include ointments, lotions, creams, gels, drops, suppositories, sprays, liquids and powders. For topical administration to a mucous membrane of the gut, an oral dosage form such as a liquid, emulsion, tablet, caplet or capsule may be used. Conventional pharmaceutical carriers, excipients and dulients may be employed.

In some embodiments, the compositions are administered in a dosage form suitable for topical or transdermal administration. Non-limiting examples of dosage forms suitable for topical or transdermal administration of a pharmaceutical composition as disclosed herein include ointments, pastes, creams, lotions, gels, powders, solutions, suspensions, emulsions, sprays, inhalants, or patches. The composition is typically admixed under sterile conditions with a pharmaceutically acceptable carrier and any needed preservatives or buffers as may be required.

In some embodiments, the composition is in a dosage form suitable for oral administration. Such a dosage form may, for example, be useful for administration to an oral, esophageal, gastric or intestinal mucosal site. The composition may or may not be swallowed depending on the target mucosal site. For example, the dosage form could be a mouth wash. In some embodiments, the oral dosage form is a liquid dosage form, such as a suspension, solution or emulsion. In some embodiments, the dosage form is a solid dosage from, such as a powder, tablet, capsule or caplet.

In some embodiments, the composition is in a dosage form suitable for rectal or vaginal administration. In some embodiments, the composition for rectal or vaginal administration is in the form of a suppository. In some embodiments, the composition for rectal or vaginal administration is in the form of a liquid, such as a douche or enema. In some embodiments, the composition for rectal or vaginal administration is in the form of a cream, ointment or gel, which may optionally be applied using an applicator.

In some embodiments, the composition is in a dosage form suitable for nasal or pulmonary administration. In some embodiments, the dosage form for nasal or pulmonary administration is a spray or inhalant. In one embodiment, the dosage form is a spray. In one embodiment, the dosage form in an inhalant, which may be administered with an inhaler.

In some embodiments, the composition is in a dosage form suitable for ocular or otic administration, i.e. administration to the eye or ear. In some embodiments, the dosage form for ocular or otic administration is a drop. In some embodiments, the composition is in a dosage form suitable for ocular administration, such as a drop, gel or ointment. Such drop, gel or ointment may, for example, be applied to the anterior surface of the eye.

Parenteral routes of administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump.

In some embodiments, parenteral routes are desirable since they avoid contact with the digestive enzymes that are found in the alimentary canal. According to such embodiments, the nanoparticle compositions may be administered by injection (e.g., intravenous, subcutaneous or intramuscular, intraperitoneal injection), rectally, vaginally, topically (as by powders, creams, ointments, or drops), or by inhalation (as by sprays).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Ointments, pastes, creams, and gels may contain, in addition to the nanoparticle delivery system of the present disclosure, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the inventive conjugates of this invention, excipients such as lactose, talc, silicic acid, aluminum hydroxide, calcium silicates, and polyamide powder, or mixtures thereof. Sprays can additionally contain customary propellants such as chlorofluorohydrocarbons.

Pharmaceutical compositions for oral administration can be liquid or solid. Liquid dosage forms suitable for oral administration of inventive compositions include pharmaceutically acceptable emulsions, microemulsions, solutions, suspensions, syrups, and elixirs. In addition to an encapsulated or unencapsulated conjugate, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants, wetting agents, emulsifying and suspending agents, sweetening, flavoring, and perfuming agents. As used herein, the term "adjuvant" refers to any compound which is a nonspecific modulator of the immune response. In certain embodiments, the adjuvant stimulates the immune response. Any adjuvant may be used in accordance with the present invention. A large number of adjuvant compounds is known in the art (Allison Dev. Biol. Stand. 92:3-11, 1998; Unkeless et al. Annu. Rev. Immunol. 6:251-281, 1998; and Phillips et al. Vaccine 10:151-158, 1992).

Solid dosage forms for oral administration include capsules, tablets, caplets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

Dosage

It will be appreciated that the exact dosage of the nanoparticle or components thereof, such as a therapeutic agent, may be determined by a physician in view of the patient to be treated. In general, dosage and administration are adjusted to provide an effective amount of the inventive conjugate to the patient being treated. As used herein, the "effective amount" refers to the amount necessary to elicit the desired biological response. As will be appreciated by those of ordinary skill in this art, the effective amount may vary depending on such factors as the desired biological endpoint, the drug to be delivered, the target tissue, the route of administration, etc. Additional factors which may be taken into account include the severity of the disease state; age, weight and gender of the patient being treated; diet, time and frequency of administration; drug combinations; reaction sensitivities; and tolerance/response to therapy.

The compositions described herein may be formulated in unit dosage form for ease of administration and uniformity of dosage. The expression "unit dosage form" as used herein refers to a physically discrete unit appropriate for the patient to be treated. It will be understood, however, that the total daily dosage of the composition of the present invention may be decided by a physician. For any composition, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of conjugates can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices may be useful in some embodiments. The data obtained from cell culture assays and animal studies can be used in formulating a range of dosage for human use.

Kits and Commercial Packages

The present disclosure also provides any of the above-mentioned compositions in kits or commercial packages, optionally with instructions for use or administration of any of the compositions described herein by any suitable technique as previously described. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, but can also include the composition of the invention and instructions of any form that are provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating the compositions of the invention in some cases. The kits also can include other containers with one or more solvents, surfactants, preservative and/or diluents (e.g., normal saline (0.9% NaCl), or 5% dextrose) as well as containers for mixing, diluting or administering the components in a sample or to a subject in need of such treatment.

The compositions of the kit may be provided as any suitable form, for example, as liquid solutions or as dried powders. When the composition provided is a dry powder, the composition may be reconstituted by the addition of a suitable diluent, which may also be provided. In embodiments where liquid forms of the composition are used, the liquid form may be concentrated or ready to use. The diluent will depend on the components of the composition and the mode of use or administration. Suitable diluents for drug compositions are well known, for example as previously described, and are available in the literature. The diluent will depend on the conjugate and the mode of use or administration.

The present disclosure also encompasses, in another aspect, promotion of the administration of the nanoparticle delivery system described herein. In some embodiments, one or more compositions of the invention are promoted for the prevention or treatment of various diseases such as those described herein via administration of any one of the compositions of the present invention. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

Methods of Treatment and Use

The nanoparticle compositions disclosed herein may be useful in the treatment or prevention of any disease or condition capable of being treated via controlled delivery of a therapeutic agent to a mucosal site. As used herein "treating" includes preventing, reducing or alleviating one or more signs and/or symptoms of the disease or condition. The nanoparticle compositions provide controlled release of the therapeutic agent and are surface-functionalized for targeting and retention of the nanoparticles at the mucosal site such that sustained release at the mucosal site can be achieved.

In some embodiments, there are provided methods of treating a disease or condition in a subject by administering an effective amount of a composition or component thereof as defined herein. In other embodiments, there are provided uses of the compositions or components thereof as defined herein for treating and/or preventing a disease or condition. In other embodiments, there are provided uses of the compositions or components thereof as defined herein for the manufacture of a medicament to treating and/or preventing a disease or condition. In other embodiments, there are provided compositions or components thereof disclosed herein for the manufacture of a medicament to treating and/or preventing a disease or condition. In other embodiments, there are provided compositions or components thereof as defined herein for the treatment of a disease or condition.

In some embodiments, the disease or condition to be treated is a disease or condition capable of being treated via delivery of a therapeutic agent to a mucosal site, such as a mucosal site of the mouth, eye, ear, nose, esophagus, stomach, small intestine, large intestine, rectum, vagina, urethra, penis or uterus. In some embodiments, the disease or condition to be treated is a disease or condition affecting the mouth, eye, ear, nose, esophagus, stomach, small intestine, large intestine, rectum, vagina, urethra, penis, or uterus. In some embodiments, the disease or condition to be treated is a disease or condition affecting the mouth, eye, ear or nose. In some embodiments, the disease or condition to be treated is a disease or condition affecting the rectum, vagina, urethra, penis, or uterus. In some embodiments, the disease or condition to be treated is a disease or condition affecting the esophagus, stomach, small intestine or large intestine.

In some embodiments, the disease or condition to be treated is a disease or condition affecting the eye. Non-limiting examples include abrasion, acanthamoeba keratitis, actinic keratosis, acute allergic blepharoconjunctivitis, allergic conjunctivitis, adenoviral keratoconjunctivitis, aniridia, atopic keratoconjunctivitis, bacterial conjunctivitis, bacterial keratitis, band keratopathy, basal cell carcinoma, Bell's palsy, blepharitis, bullous keratopathy, canaliculitis, caruncular cyst, cataract, chalazion, chlamydial conjunctivitis, climatic droplet keratopathy, concretions, conjunctival intraepithelial neoplasia, conjunctival lymphoma, conjunctival papilloma, conjunctival pigmented lesions, conjunctival scarring, conjunctivitis, conjunctivochalasia and chemosis, corneal collagen cross-linking, corneal edema, corneal graft-lamellar keratoplasty, corneal graft rejection, corneal infiltrates, crocodile shagreen, crystalline keratopathy, cysts of the eye lids, dacryocystitis, dellen, dendritic ulcer, dermatochalasis and blepharochalasis, Descemet's membrane breaks, disciform keratitis, disciform keratitis, keratoconjunctivitis sicca, ectopia lentis, ectropion, endophthalmitis, entropion, epiblepharon and epicanthic folds, epibulbar choristomas, epiphora, episcleritis, epithelial and fibrous ingrowth, epithelial basement membrane dystrophy, exposure keratopathy, eyelid trauma, filamentary keratopathy, filtering bleb, flash burns, floppy eyelid syndrome, follicular conjunctivitis, Fuchs' endothelial dystrophy, Fuchs' heterochromic iridocyclitis, fungal keratitis, giant papillary conjunctivitis, glaucoma-acute angle closure, gonococcal keratoconjunctivitis, granular dystrophy, hemangioma, herpes simplex keratitis, herpes simplex primary blepharokeratoconjunctivitis, herpes zoster ophthalmicus, hordeolum-internal and external, hyphema-blunt trauma, hypopyon, infectious crystalline keratopathy, interstitial keratitis, iridocorneal dysgenesis, iridocorneal endotheliopathy, iris cysts, iritis, iron lines, keratoconus, keratoconus forme frusta, keratoglobus, lattice stromal dystrophy, leukocoria, lice, limbal stem cell deficiency, lipid keratopathy, macular stromal dystrophy, marginal keratitis, meesmann's dystrophy, melanoma-conjunctival and eyelid, melanoma and nevus of the iris, membranous and pseudomembranous conjunctivitis, molluscum contagiosum, mooren's ulcer, nasolacrimal duct obstruction-congenital, neurotrophic keratopathy, nevus-eyelid, ocular cicatricial pemphigold, ophthalmia neonatorum, pannus and pseudopterygia, pellucid marginal degeneration, perforation-corneal, peripheral ulcerative keratitis, persistent epithelial defect, phlyctenulosis, pingueculum, posterior capsular opacification, posterior polymorphous dystrophy, preseptal cellulitis, pseudoexfoliation of the lens capsule, pterygium, ptosis and pseudoptosis, punctual stenosis, pyogenic granuloma, recurrent corneal erosion syndrome, Reis-Buckler's dystrophy, retention cyst and lymphangiectasia, rheumatoid arthritis, rosacea keratitis, Salzmann nodular degeneration, scleritis, sebaceous cell carcinoma, seborrheic keratosis, squamous cell carcinoma-lid, Stevens-Johnson syndrome, sub-conjunctival hemorrhage, superficial punctate keratopathy, superior limbic keratoconjunctivitis, synechia, Terrien's marginal degeneration, Thygeson's superficial punctate keratopathy, toxic keratopathy, trachoma, trichiasis, pseudotrichiasis, distachiasis, metaplastic lashes, trichotillomania, uveitis, vernal keratoconjunctivitis, vitamin A deficiency, vortex keratopathy, xanthelasma.

In some embodiments, the disease or condition is a disease or condition of the eye is glaucoma, keratoconjunctivitis sicca or allergic conjunctivitis, fungal infection, viral infection or bacterial infection. In some embodiments, the disease or condition of the eye is glaucoma, keratoconjunctivitis sicca or allergic conjunctivitis. In some embodiments, the disease or condition of the eye is a fungal infection, viral infection or bacterial infection.

In some embodiments, Cyclosporine A is administered for the treatment of keratoconjunctivitis sicca. In some embodiment, Olopatadine is administered for the treatment of allergic conjunctivitis. In some embodiment, Brinzolamide, Brimonidine, or Dorzolamide, are administered for the treatment of glaucoma.

In some embodiments, the composition is administered topically on the surface of the eye for treatment of diseases associated with the anterior segments of the eye.

In some embodiments, the composition is administered topically on the surface of the eye for treatment of diseases associated with the posterior segments of the eye. In some embodiments, the composition is administered intranasally to target the nasal mucosa. In some embodiments, the composition is administered orally to target the oral mucosa. In some embodiments, the composition is administered intravenously to target the gastrointestinal mucin for treatment of diseases associated with the intestine. In some embodiments, the composition is administered vaginally to target the vaginal mucosa. In some embodiments, the composition administered rectally to target the rectal mucosa.

In some embodiments, the disease or condition to be treated is selected from one or more of acquired angioedema, acrodermatitis enteropathica, acute serous conjunctivitis, adenomatous polyposis of the colon, adenoviridae infections, adenovirus-related cold, allergic asthma, allergic contact cheilitis, allergic rhinitis, allergies, amyloidosis of gingiva and conjunctiva mental retardation, analgesic asthma syndrome, Anderson's triad, angina bullosa haemorrhagica, angular conjunctivitis, asthma, asthmatic Bronchitis, atrophic glossitis, atrophic rhinitis, attenuated familial polyposis, Behcet's disease, benign migratory glossitis, benign mucosal penphigoid, black hairy tongue, Brodie pile, bronchitis, bullous penphigoid, candidiasis, canker sores, carbon baby syndrome, cariomegaly, catarrh, catarrhal or mucopurulent conjunctivitis, central papillary atrophy, cervical polyps, cheilitis, cheilitis exfoliativa, cheilitis glandularis, cheilitis granulomatosa, cholecystitis, cicatrizing conjunctivitis, ciliary discoordination due to random ciliary orientation, ciliary dyskinesia, colitis, colorectal adenomatous polyposis, colorectal polyps, conjunctivitis ligneous, conjunctivitis with pseudomembrane, coronavirus-related cold, costello syndrome, coxsackievirus-related cold, Crohn's disease, cronkhite-Canada syndrome, cystic Fibrosis, cystitis, dermatostomatitis, desquamative gingivitis, dextrocardia-bronchiectasis-sinusitis, drug-induced ulcer of the lip, duodenal ulcer, dyskeratosis congenital, dyskeratosis congenita of Zinsser-Cole-Engman, echovirus-related cold, Ectodermal dysplasia, enterocolitis, eosinophilic cystitis, epidemic kaposi's sarcoma, epulis, epulis fissuratum, eruptive hemangioma, eruptive lingual papillitis, erythroplakia, esophageal ulcer, esophagitis, extrinsic asthma, familial adenomatous polyposis, familial intestinal polyposis, familial nasal acilia, familial polyposis, Fenwick ulcer, fissured tongue, flu, folicular conjunctivitis, follicular hamartoma, food allergy related asthma, Fordyce's disease, Gardner syndrome, gastresophageal reflux-related chronic cough, gastric erosion, gastric reflux, gastric ulcer, gastritis, gastritis, gastroesophageal reflux disease, giant papillary conjunctivitis, gonorrhea, growth-hormone secreting pituitary adenoma, hairy leukoplakia, hemophilus influenzae B, hemorrhagic conjunctivitis, hemorrhagic proctocolitis, herpes, human papillomavirus, immotile cilia syndrome, inclusion conjunctivitis, influenza A, influenza B, interstitial cystitis, intraoral dental sinus, intrinsic asthma, invasive candidiasis, irritative conjunctivitis, Jadassohn-Lewandowsky syndrome, kaposiform hemangio-endothelioma, keratoconjunctivitis, keratosis pharynges, laryngopharyngeal reflux, leprosy, leukoencephalopathy, leukoplakia, leukoplakia with tylosis and esophageal carcinoma, lipogranulomatosis, logic syndrome, lower esophageal ulcer, lymphocytic colitis, lymphoma, mucosa-associated lymphoid tissue, major ulcerative stomatitis, malignant peptic ulcer, Melkersson-Rosenthal syndrome, membranous conjunctivitis, mouth ulcers, mucinous carcinoma, mucocele, mucoepidermoid, mucoepidermoid carcinoma, mucoepithelial dysplasia, Witkop type, mucosal leishmaniasis, mucosal lichen planus, mucosal squamous cell carcinoma, mucositis, mucous cyst of oral mucosa, Nagayama's spots, nasal polyp, necrotizing entercolitis, necrotizing periodontal diseases, nicotine stomatitis, ophthalmia neonatorum, oral Crohn's disease, oral florid papillomatosis, oral fordyce granules, oral thrush, oral ulcer, orthomyxovirus-related cold, Osler-Rendu-Weber syndrome, pancolitis, papillary conjunctivitis, parainfluenza, paramyxovirus-related cold, paucigranulocytic asthma, pemphigus, pemphigus foliaceus, pemphigus volgaris, Penign peptic ulcer, penphigus vulgaris, peptic ulcer, periadenitis mucosa necrotica, periodic fever, pharyngoconjunctival fever, Pinguecula, plasma cell cheilitis, plasmoacanthoma/plasma cell gingivitis, primary ciliary dyskinesia, proctitis pseudomembranous colitis, pseudomycoma peritonei, psoriasis on mucous membranes, psychiatric disorders associated celiac disease, pterygium, pterygium of the conjunctiva, purulent conjunctivitis, recurring scarring apthae, reflux laryngitis, refractory celiac disease, Rhinitis, rhinosporidiosis, ritter syndrome, rostan asthma, salicylate-sensitive asthma, Schafer syndrome, sinusitis, Sjogren syndrome, spring catarrh, sprue, Stevens-Johnson syndrome, stomal ulcer, stomatitis, superior limbic keratoconjunctivitis, Sutton disease, swime flu, systemic candidiasis, Takahara's disease, the clap, thrush, trumpeter's wart, tuberculous disease of the mucous, ulcerative colitis, ulcerative conjunctivitis, ulcerative proctosigmoiditis, urban Schosser Spohn synfrome, vaginal candidiasis, vasomotor rhinitis, vestibular papillomatosis, Vincent's angina, vulvovaginal gingival syndrome, white sponge nevus, xanthogranulomatous cholecystitis, xerostomia Subject The subject may be a human or non-human animal. In some embodiments, the subject is a mammal. Non-limiting examples of mammals include human, dog, cat, horse, donkey, rabbit, cow, pig, sheep, goat, rat, mouse, guinea pig, hamster, and primate. In some embodiments, the subject is a human.

Methods of Manufacture

In another aspect, the present disclosure provides a process for the preparation of macromolecules useful in the formation of a mucoadhesive nanoparticle delivery system. The macromolecule is typically an amphiphilic copolymer, in particular, a block copolymer, which is conjugated to a plurality of mucosal targeting moieties. The macromolecules are capable of assembly under suitable conditions to form a nanoparticle, i.e. of the core-shell type. In an aqueous environment, the nanoparticle has a hydrophobic core and a hydrophilic shell, the shell providing a surface of the nanoparticle, the surface of the nanoparticle being coated in a desired amount (i.e. surface density) of the mucosal targeting moiety for controlled targeting and adhesion of the nanoparticle.

The macromolecules disclosed herein may be made by any suitable process known to those skilled in the art, for example, using suitable conjugation techniques. Starting materials, including hydrophobic polymer and hydrophilic polymer, may be purchased from various commercial suppliers. Where desired, the starting materials can be prepared by those of skill in the art. For example, where polymers comprising modified backbone residues are desired. Exemplary methods for making macromolecules useful in the formation of a mucoadhesive delivery system are described below.

In some embodiments, there is provided a method of preparing a nanoparticle composition.

In some embodiments, the method is carried out in a series of steps, such as, preparation of an amphiphilic macromolecule, nanoparticle formation, and conjugation to a targeting moiety (i.e. coating of the surface of the nanoparticle with a desired surface density of the targeting moiety). Alternatively, the hydrophilic portion comprising multiple functional groups may first be coupled to a desired amount of the targeting moiety, followed by conjugation of the functionalized hydrophilic portion to a hydrophobic polymer, which may be in the form of a hydrophobic nanoparticle (i.e. coating the surface of a hydrophobic nanoparticle with a functionalized hydrophilic polymer). When the hydrophobic polymer is modified for conjugation, one end of the polymer will typically become more hydrophilic (e.g. presence of a carboxyl group). Such polymers can assemble to form hydrophobic nanoparticles in aqueous medium. Preparation of the nanoparticles in a controlled sequence results in surface-functionalized nanoparticles wherein substantially all (e.g. greater than 90%, 95%, 96%, 97%, 98%, 99%) of the targeting moieties are located on the surface of the nanoparticle formed by the hydrophilic portion of the macromolecules.

In one embodiment, the method of preparing a nanoparticle composition useful for delivery of a payload to a mucosal site comprises preparing an amphiphilic macromolecule comprising a hydrophilic portion and a hydrophobic portion, the hydrophilic portion comprising multiple functional moieties; b) assembling a plurality of said macromolecules under suitable conditions to form a nanoparticle having a hydrophobic core and a hydrophilic shell; and c) conjugating at least a portion of said functional moieties on the hydrophobic portion to a mucosal targeting moiety, to thereby provide a surface-functionalized nanoparticle.

In some embodiments, a) comprises conjugation of a hydrophilic polymer to a hydrophobic polymer to form a diblock copolymer.

In some embodiments, the hydrophilic polymer is dextran and the hydrophobic polymer is PLA.

In some embodiments, the targeting moiety is a phenylboronic acid derivative, a thiol derivative or an acrylate derivative. In some embodiments, the targeting moiety is a phenylboronic acid (PBA) derivative.

In some embodiments, step b) is performed before step c). However, in other embodiments, step c) is performed before step b).

In some embodiments, the surface density of the mucosal targeting moiety on the nanoparticle is controlled by the amount of mucosal targeting moiety introduced into the reaction.

In some embodiments, the process comprises reductive animation between the multimer and a suitable linker. In some embodiments, the reaction takes place between the amine end of N-protected-ethylenediamine and the reducing end of a multimer having multiple functional groups per monomer unit, such as a polysaccharide, a polynucleotide or a polypeptide. Any suitable N-protecting group can be used. In some embodiments, the N-protecting group is tert-butoxycarbonyl (BOC).

The choice of a hydrophilic polymer having multiple functional groups per monomer unit enables tuning of the resulting nanoparticle to control particle size, targeting and/or adhesion at a mucosal site, as described further below. In some embodiments, the hydrophilic polymer is a polysaccharide. In some embodiments, the hydrophilic polymer is dextran. Therefore, in some embodiments, the reaction takes place between N-BOC-ethylenediamine and an aldehyde of the reducing end of a dextran polymer. The reaction may be carried out in a suitable solvent, such as a borate buffer solution, in the presence of a reducing agent, such as $NaCNBH_3$. The mixture is stirred for a sufficient amount of time to complete the reaction, for example, about 24 to 120 hours. In one embodiment the mixture is stirred for about 24, 48, 72, 96, or 120 hours. In some embodiments, this step is carried out at room temperature. In some embodiments, this step is carried out in the dark.

The mixture may then be washed to remove any unreacted molecules or catalysts. In one embodiment methanol is used in the washing step. The end-modified dextran can optionally be dried before continuing the process.

The protecting group is then removed followed by conjugation of the amine-terminated multimer to a hydrophobic polymer in a suitable solvent to provide an amphiphilic macromolecule. In one embodiment, hydrochloric acid and triethyl amien are used for the removal of the protecting group. The macromolecule may be washed, for example, using methanol, to remove unreacted polymer.

The conjugation of the amine-terminated multimer with a hydrophobic polymer takes place in a suitable solvent. In one embodiment, the solvent is DMSO, acetone, or acetonitrile. Catalysts may be employed to drive the reaction. In one embodiment, the catalysts are EDC and Sulfo-NHS.

The mixture may then be washed to remove any unreacted molecules or catalysts. In one embodiment methanol is used in the washing step. Additional washing step may be used to remove unreacted polymer. In one embodiment, the unreacted polymer is dextran. The final mixture is dissolved in a suitable solvent, centrifuged and the resulting supernatant is collected. In one embodiment, the suitable solvent is acetone or acetonitrile. The final product is dried. In one embodiment, vacuum dessicator is used to dry the product.

In another aspect, the present disclosure provides a process for the preparation of nanoparticles useful in the formation of a mucoadhesive nanoparticle delivery system. The polymers or macromolecules described herein may be formed into a nanoparticle using techniques known to those skilled in the art. The geometry formed by the particle from the macromolecule may depend on factors such as the size and composition of the polymers that form the macromolecule. In addition, also as discussed below, in some cases, the particle may include an agent of interest, such as a therapeutic, diagnostic or imaging agent. For example, in some embodiments, the nanoparticle may contain a therapeutic agent, such as a drug. The agent of interest may be incorporated into the particle during formation of the particle, e.g., by including the agent in a solution containing the polymers that are used to form the particle, and/or the agent may be incorporated in the particle after its formation.

In addition, the method may employ additional polymers or macromolecules distinguishable from the polymers or macromolecules discussed above. As previously discussed, first and second (or more) macromolecules may be combined together at different ratios to produce particles comprising the first and second (or more) macromolecules, keeping in mind that, in some embodiments, it is desirable to have hydrophilic portions with multiple functional groups present in the shell of the nanoparticle for tunable targeting of the nanoparticles via coupling of the functional groups to a mucosal targeting moiety, such as a targeting moiety capable of forming high affinity binding to a target at the mucosal site.

In some embodiments, the targeting moieties are conjugated to the macromolecules following nanoparticle formation.

The present disclosure also provides a process for conjugating targeting moieties on the surface of the nanoparticles formed using the amphiphilic macromolecules described herein. In some embodiments, the conjugation is between the functional groups of the hydrophilic portion (e.g. the backbone of a hydrophilic polymer) and the functional groups of the targeting moieties. In some embodiment, catalysts, for example, EDC, are used for the conjugation reaction. In some embodiments, the functional groups of the polymer backbone are modified into other types of functional groups prior to the conjugation reaction. In one embodiment, $NaIO_4$ is used to oxidize hydroxyl groups into aldehyde groups. The mixture may be washed, for example, using methanol, to remove nonconjugated targeting moieties. In some embodiment, dialysis is used to remove the unreacted molecules.

In some cases, the method may include conjugation with more than one type of targeting moiety. The surface density of targeting moiety on the resulting nanoparticles may be controlled by adjusting the amount of material in the reaction mixture.

In some embodiments, conjugation and nanoparticle formation may occur as a single-step reaction, for example, according to a single-step reaction as described in U.S. Pat. No. 8,323,698. However, a single-step reaction such as this will result in a nanoparticle having a detectable amount of targeting moieties located within the core of the nanoparticle, thereby decreasing the targeting efficiency of the particles compared to a more controlled sequence as described above.

Specific reaction conditions can be determined by those of ordinary skill in the art using no more than routine experimentation.

Embodiment of the Method

An exemplary method of preparing a Dextran-b-PLA (Dex-b-PLA) block copolymer is described below in Example 1 (Verma, 2012). Briefly, an exemplary procedure for the synthesis of Dex-b-PLA may be divided into three stages: reductive amination between Dextran and N-Boc-ethylenediamine, deprotection of the Boc group, and conjugation of the amine-modified Dextran end group with carboxyl-terminated PLA. Reductive amination may be carried out by dissolving Dex in a borate buffer and mixing it with N-Boc-ethylenediamine and $NaCNBH_3$ in dark condition for about 72 hrs. After the reaction, the mixture is washed with methanol and dried in vacuum desiccator. The sample is then dissolved in DI-$H_2O$ and treated with hydrochloric acid and triethyl amine for the deprotection of the Boc group. The conjugation of amine-terminated Dextran and PLA was carried out in DMSO with EDC and Sulfo-NHS as catalysts for about 4 hrs. The final product was washed several times with methanol. The wash sample was further dissolved in acetone and centrifuged. The supernatant was extracted carefully in order to separate from free unreacted Dextran that have been precipitated. Finally, the supernatant containing Dex-b-PLA was dried in vacuum desiccator.

Thus, in some embodiments, there is provided a method of preparing a Dex-b-PLA macromolecule, the method comprising: 1) reductive amination between Dextran and N-Boc-ethylenediamine, 2) deprotection of the Boc group, and 3) conjugation of the end modified Dextran with PLA (Scheme 1). The first step of the synthesis involves reductive amination between the aldehyde on the reducing end of Dextran and the amine group of N-Boc-ethylenediamine cross-linker. The reducing agent, $NaCNBH_3$ was added to the borate buffer solution and the mixture was stirred for 72 hours in dark conditions at room temperature. The mixture was then washed in methanol to remove any unreacted molecules or catalysts. The end-modified Dextran was dried overnight in vacuo. The dried Dextran was re-dissolved in de-ionized water (DI-$H_2O$). The deprotection of Boc group was performed first by adding HCl for 1 hour to cleave the amide bond between the Boc group and the protected amine moiety. Subsequently, TEA was added to increase the pH of the solution up to 9 to deprotonate the $NH_3^+$ end groups which were deprotected. The mixture was then washed twice using methanol and dried in vacuo. An NMR sample of the dried product was prepared in $D_2O$ ( ). The amine terminated Dextran and carboxyl terminated PLA20 (Mw~20 kDa, 6 g, 0.3 mmol) were dissolved in DMSO. The conjugation between the two polymers was facilitated by adding catalysts EDC (120 mg, 0.773 mmol) and Sulfo-NHS (300 mg, 1.38 mmol) and allowing reaction to proceed for 4 hours at room temperature. The resulting Dex-b-PLA was twice precipitated and purified using excess methanol. In order to remove free Dextran, the mixture was dissolved in acetone (30 mL) to form a cloudy suspension. This was centrifuged at 4000 rpm for 10 minutes and the supernatant was extracted carefully. The supernatant was purged with air to remove the solvent and then dried overnight in vacuo to obtain the final copolymers.

To functionalize the polymers, Dex-b-PLA may be dissolved in DMSO (30 mg/ml), and added slowly into water under mild stirring. Periodate oxidation of the Dextran surface was carried out by adding 60 mg of $NaIO_4$ and stirring for an hour. Subsequently, glycerol was added to quench the unreacted $NaIO_4$. Various amounts of PBA (i.e. 40 mg for Dex-b-PLA_40 PBA) were added to the mixture, along with $NaCNBH_3$, for 24 hours. All reactions were carried out in the dark. The mixture was then dialyzed in water for 24 hrs to remove any unreacted solutes, through changing the wash medium 4 times.

The polymers or macromolecules described herein may be formed into a nanoparticle using techniques know to those skilled in the art, including those discussed in detail below. The geometry formed by the particle from the polymer or macromolecule may depend on factors such as the polymers that form the particle. In addition, also as discussed below, in some cases, the particle may include a hydrophilic agent or a hydrophobic agent of interest, depending on the structure of the particle. For example, the particle may contain a drug or other therapeutic agent. The hydrophilic or hydrophobic agent may be incorporated in the particle during formation of the particle, e.g., by including the agent in a solution containing the polymers that are used to form the particle, and/or the agent may be incorporated in the particle after its formation.

The Dex-b-PLA NPs were prepared using nanoprecipitation method: 1 mL of Dex-b-PLA in DMSO (10 mg/mL) was added in a drop-wise manner to 10 mL of DI-$H_2O$ under constant stirring in order to form NPs. This was stirred for 30 minutes and then dynamic light scattering (DLS) samples were prepared by extracting 3 mL samples into polystyrene cuvettes. The sizes of the NPs were analyzed using 90Plus Particle Size Analyzer (Brookhaven, $\lambda$=659 nm at 90°). The volume averaged multimode size distribution (MSD) mean diameters were used from the results.

In addition, the method may employ additional polymers or macromolecules, which may be distinguishable from the polymers or macromolecules discussed above. As previously discussed, the first and second macromolecules may be combined together at different ratios to produce particles comprising the first and second macromolecules.

In some cases, the method may include conjugation with more than one type of targeting moiety. The surface density of targeting moiety on the resulting nanoparticles may be controlled by adjusting the amount of material in the reaction mixture.

Alternatively, the reaction may occur as a single-step reaction, i.e., the conjugation is performed without using intermediates such as N-hydroxysuccinimide or a maleimide, such as that described in U.S. Pat. No. 8,323,698. However, such method results in a nanoparticle having a portion of the targeting moiety located in the core of the particle. Thus, typically, a multi-step approach will be used to achieve higher targeting efficiency.

Specific reaction conditions can be determined by those of ordinary skill in the art using no more than routine experimentation.

Particular Embodiments

In some embodiments, there is provided a nanoparticle composition useful for delivery of a payload to a mucosal site, the nanoparticle comprising a plurality of amphiphilic macromolecules, the macromolecules comprising: a hydrophobic portion comprising a biocompatible polymer selected from a from polylactide, a polyglycolide, poly(lactide-co-glycolide), poly($\varepsilon$-caprolactone), or a combination thereof; a hydrophilic portion comprising a biocompatible polymer selected from polysaccharide, polynucleotide, polypeptide, or a combination thereof, the hydrophilic portion comprising multiple functional moieties; and a mucosal targeting moiety selected from a phenylboronic acid (PBA) derivative, a thiol derivative or an acrylate derivative, wherein at least a portion of said functional moieties of the hydrophilic portion are conjugated to the mucosal targeting moiety.

In some embodiments, there is provided a nanoparticle composition useful for delivery of a payload to a mucosal site, the nanoparticle comprising a plurality of amphiphilic macromolecules, the macromolecules each comprising: a hydrophobic biocompatible polymer selected from a from polylactide, a polyglycolide, poly(lactide-co-glycolide), poly($\varepsilon$-caprolactone), or a combination thereof, the hydrophobic polymer forming the core of the nanoparticle; a hydrophilic biocompatible polymer selected from polysaccharide, polynucleotide, polypeptide, or a combination thereof, having multiple functional moieties, the hydrophilic portion forming the shell of the nanoparticle; at least a portion of the functional moieties being conjugated to a mucosal targeting moiety selected from a phenylboronic acid (PBA) derivative, a thiol derivative or an acrylate derivative.

In some embodiments, there is provided a nanoparticle composition useful for delivery of a payload to a mucosal site, the nanoparticle comprising a plurality of amphiphilic macromolecules, the macromolecules comprising: a hydrophobic portion comprising a polylactide; a hydrophilic portion having multiple functional moieties, said hydrophilic portion comprising dextran; and a mucosal targeting moiety being a phenylboronic acid (PBA) derivative, wherein at least a portion of said functional moieties of the hydrophilic portion are conjugated to the mucosal targeting moiety.

In some embodiments, there is provided a nanoparticle composition useful for delivery of a payload to a mucosal site, the nanoparticle comprising a plurality of amphiphilic macromolecules, the macromolecules each comprising a hydrophobic polylactide polymer conjugated to a hydrophilic dextran polymer having multiple functional moieties, at least a portion of said functional moieties being conjugated to a phenylboronic acid (PBA) derivative.

In some embodiments, the macromolecule is Dextran-p-PLA. In some embodiment, the functionalized macromolecule is Dextran-p-PLA_PBA.

In some embodiments, the nanoparticle is formed by conjugating the polylactide to the dextran to form macromolecule, then forming a nanoparticle, and subsequently surface-functionalizing the nanoparticle by conjugating at least a portion of the functional moieties of the dextran to the PBA derivative to achieve a desired surface density of the PBA derivative.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

In the claims, as well as in the specification above, all transitional phrases such as "comprising," "including," "carrying," "having," "containing," "involving," "holding," "formed from", "composed of," and the like are to be understood to be open-ended, i.e., to mean including but not limited to.

Only the transitional phrases "consisting of" and "consisting essentially of" shall be closed or semi-closed transitional phrases, respectively.

The following examples are intended to illustrate certain exemplary embodiments of the present disclosure. However, the scope of the present disclosure is not limited to the following examples.

EXAMPLES

Example 1. Synthesis and Characterisation of Dex-b-PLA 1.1 Materials

Acid-terminated poly(D,L-lactide) (PLA, $M_w$~10, 20 and 50 kDa) and PLGA-PEG (PLGA $M_w$~40 kDa, PEG $M_w$~6 kDa) were purchased from Lakeshore Biomaterials (Birmingham, Ala., USA). PLA was purified by dissolving in dimethyl sulfoxide (DMSO) and precipitating in methanol to remove residual monomers. Dextran (Dex, $M_r$~1.5, 6, and 10 kDa), hydrochloric acid (HCl), triethylamine (TEA), N-(3-dimethylaminopropyl)-N-ethylcarbodiimide (EDC), and sodium cyanoborohydride (NaCNBH$_3$) were purchased from Sigma Aldrich (Oakville, ON, Canada), and used without further purification. N-Hydroxysulfosuccinimide (Sulfo-NHS) and N-Boc-ethylenediamine were purchased from CNH Technologies (Massachusetts, USA). Doxorubicin-HCl (MW=580 Da, Intatrade GmBH, Bitterfield, Germany) was deprotonated by adding TEA (2M equivalent) in the aqueous solution of Doxorubicin-HCl, and the hydrophobic form of Doxorubicin was extracted using Dichloromethane (DCM) (Chittasupho, 2009). Borate buffer was prepared at a concentration of 0.05M with pH of 8.2 by mixing boric acid and sodium hydroxide. Whole sheep blood (in Alsever's) was purchased from Cedarlane (Burlington, ON, Canada). Veronal Buffer solution (VBS, 5×) was purchased from Lonza Walkersville Inc (Walkersville, Md., USA). Tritium [$^3$H]-PLA-radiolabeled nanocrystals were purchased from PerkinElmer (Boston, Mass., USA).

1.2 Synthesis of Dex-b-PLA

The synthesis of the linear block copolymer is divided into three stages: 1) reductive amination between Dextran and N-Boc-ethylenediamine, 2) deprotection of the Boc group, and 3) conjugation of the end modified Dextran with PLA (Scheme 1). The first step of the synthesis involves reductive amination between the aldehyde on the reducing end of Dextran and the amine group of N-Boc-ethylenediamine cross-linker. In a typical reaction, Dex6 ($M_r$~6 kDa, 6 g, 1 mmol) was dissolved in 15 mL of borate buffer (0.05 M, pH 8.2) with 4 g (2.5 mmol) of N-Boc-ethylenediamine. The reducing agent, NaCNBH$_3$ (1 g, 15 mmol), was added to the borate buffer solution and the mixture was stirred for 72 hours in dark conditions at room temperature. The mixture was then washed in methanol to remove any unreacted molecules or catalysts. The end-modified Dextran was dried overnight in vacuo. H NMR samples were prepared by dissolving the end-modified Dextran in D$_2$O (30 mg/mL). The dried Dextran was re-dissolved in de-ionized water (DI-H$_2$O). The deprotection of Boc group was performed first by adding HCl (~4 M) for 1 hour to cleave the amide bond between the Boc group and the protected amine moiety. Subsequently, TEA was added to increase the pH of the solution up to 9 to deprotonate the NH$_3^+$ end groups which were deprotected. The mixture was then washed twice using methanol and dried in vacuo. An NMR sample of the dried product was prepared in D$_2$O (30 mg/mL). The amine terminated Dextran and carboxyl terminated PLA20 (Mw~20 kDa, 6 g, 0.3 mmol) were dissolved in DMSO. The conjugation between the two polymers was facilitated by adding catalysts EDC (120 mg, 0.773 mmol) and Sulfo-NHS (300 mg, 1.38 mmol) and allowing reaction to proceed for 4 hours at room temperature. The resulting Dex-b-PLA was twice precipitated and purified using excess methanol. In order to remove free Dextran, the mixture was dissolved in acetone (30 mL) to form a cloudy suspension. This was centrifuged at 4000 rpm for 10 minutes and the supernatant was extracted carefully. The supernatant was purged with air to remove the solvent and then dried overnight in vacuo to obtain the final copolymers. NMR samples were prepared at a concentration of 30 mg/mL in DMSO-d6 for proton NMR and 150 mg/mL in DMSO-d6 for carbon NMR.

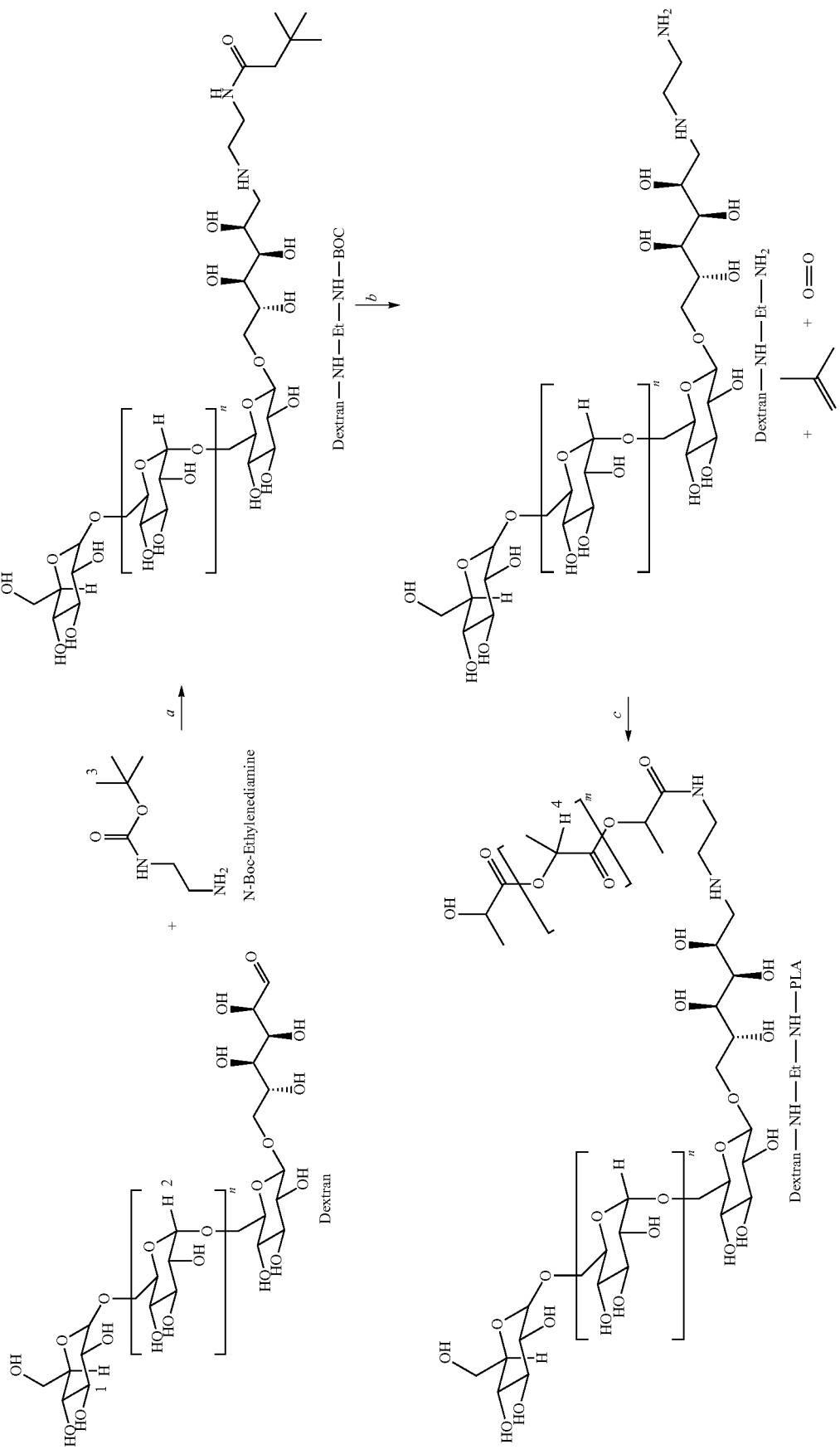

1.3 Characterization of Dex-b-PLA Using Nuclear Magnetic Resonance (NMR)

The various stages of Dex-b-PLA synthesis were verified using H NMR spectroscopy (Bruker 300 MHz). The final polymer conjugation was also verified using C NMR spectroscopy (Bruker 300 MHz). Before any modification, Dextran was dissolved in $D_2O$ (30 mg/mL) and acid terminated PLA was dissolved in $CDCl_3$ (5 mg/mL) for preparing NMR samples. As mentioned in the previous synthesis methods, the end products from the first two steps were dissolved in $D_2O$, whereas the final product, Dex-b-PLA, was dissolved in DMSO-d6 for the NMR analysis.

1.4 Dex-b-PLA NP Formation by Nanoprecipitation

The Dex-b-PLA NPs were prepared using nanoprecipitation method: 1 mL of Dex-b-PLA in DMSO (10 mg/mL) was added in a drop-wise manner to 10 mL of DI-$H_2O$ under constant stirring in order to form NPs. This was stirred for 30 minutes and then dynamic light scattering (DLS) samples were prepared by extracting 3 mL samples into polystyrene cuvettes. The sizes of the NPs were analyzed using 90Plus Particle Size Analyzer (Brookhaven, $\lambda=659$ nm at 90°). The volume averaged multimode size distribution (MSD) mean diameters were used from the results.

1.5 Transmission Electron Microscopy

The particle size and the morphology of the Dex-b-PLA NPs were further verified using Transmission Electron Microscopy (TEM, Philips CM10) with the accelerating voltage of 60 kV and the Lanthanum Hexaboride filament (LaB6). 300 Mesh Formvar coated copper grids (Canemco & Marivac) were used for this experiment. The NP suspension in water was prepared using the nanoprecipitation method as mentioned above. A drop of the NP suspension was placed onto the grid, and the grid was briefly stained with aqueous phosphotungstic acid solution. The copper grid with the NP suspension was dried under ambient environment overnight before imaging under TEM.

1.6 Results and Discussion

The synthesis of Dex-b-PLA block copolymers was analyzed using H NMR spectrometer. As shown in FIG. 1a I, the 4.86 ppm multiplet was assigned to the proton on carbon 1 of Dextran repeating units. The 3.14 ppm multiplet was assigned to the proton on carbon 5 of the non-reducing end the integral ratio between these two multiplets was used to confirm the MW of Dextran. The reductive amination reaction of Dextran and N-Boc-ethylenediamine was confirmed by the presence of 1.3 ppm peak (Boc group) after removing unreacted free N-Boc-ethylenediamine (FIG. 1a II). The subsequent deprotection of Boc group exposing the —$NH_2$ end-group on Dextran was verified by the disappearance of the 1.3 ppm peak (FIG. 1a III). It was shown that the 1.3 ppm peaks were completely removed after the deprotection steps using HCl and TEA. After the conjugation of the —$NH_2$ terminated Dextran with COOH-terminated PLA (FIG. 1a IV), the excess free Dextran molecules were removed by precipitating in acetone. The final product shows peaks corresponding to both the Dextran (multiplets at 4.86 ppm) and the PLA (multiplets at 5.2 ppm) which confirm the conjugation of the two polymers (FIG. 1a V). The linear end-to-end conjugation of PLA and Dextran was also confirmed by Carbon NMR (FIG. 1b). The peak at 166.81 ppm is assigned to the carbon on PLA that attaches to the amine terminal of the ethylenediamine linker, while 169 ppm peak is the carbonyl carbon on PLA backbone (FIG. 1b).

Figure 2A:
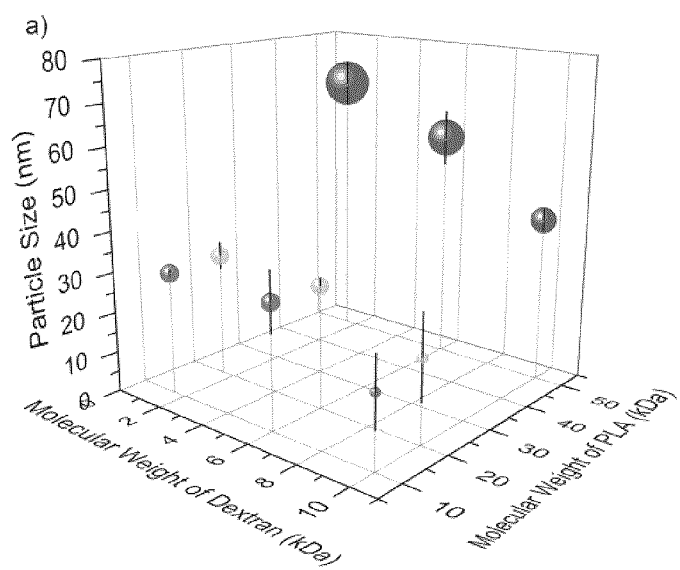
FIG. 2 shows particle size and morphology of dextran-b-PLA NPs: a) Effect of MW's of PLA and Dextran on the sizes of the NPs formed from nine different polymers using PLA with MW 10 kDa (red), 20 kDa (green) and 50 kDa (blue), and Dextran with MW 1.5 kDa, 6 kDa and 10 kDa. The black bars represent the standard deviation of the particle sizes of each block copolymer; b) TEM image of PLA20-Dex6 NPs (Scale bar is 100 nm) to demonstrate spherical shape of the nanoparticles.
Figure 2B:
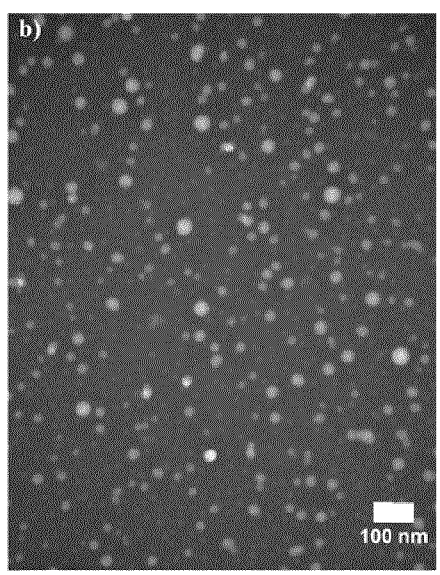

The size and morphology of NPs using nine formulations of Dex-b-PLA block copolymers are shown in FIG. 2. Varying the MW of PLA and Dextran resulted in creating NPs with different sizes ranging from 15 to 70 nm. As shown in FIG. 2a, increasing the MW of PLA increased the particle size whereas increasing the MW of Dextran decreased the particle size. The NP core, formed by PLA, was predicted to increase in size with increasing MW's of the PLA chains as demonstrated previously (Riley 1999; Riley 2001) and it was confirmed here by the NPs composed of PLA MW of 10 kDa, 20 kDa and 50 kDa. We postulate that the effect of Dextran MW on NP size is likely due to Dextran configuration on the NP surface. Zahr et al. found that hydrophilic chains, such as PEG, at MW of 5 kDa or longer would be able to "fold-down" onto the particle surface creating a mushroom conformation (Zahr 2006). Similarly, this phenomenon may explain why the NPs with longer Dextran chains lead to smaller hydrodynamic diameters. The shorter Dextran chain length has a smaller degree of freedom and confined to linear structure compared to those with longer chain length. The TEM image of NPs composed of PLA20-Dex6 ($MW_{PLA}$~20 kDa, $MW_{Dextran}$~6 kDa) confirmed the particles exhibit spherical structure (FIG. 2b).

Dex-b-PLA NPs with sizes under 50 nm have been synthesized using the simple process of bulk nanoprecipitation. PLGA-PEG block copolymer was used as a commercial benchmark, which formed NPs with size 133.9±6.1 nm following the same procedure. The particle size for PLGA-PEG is in agreement to previous literature values (Dhar 2009). PLGA-PEG NPs have been able to achieve smaller particle sizes but it required the assistance of microfluidic devices for enhanced control (Karnik 2008). The particle size of Dex-b-PLA NPs, on the other hand, can be controlled simply by changing the MW of the compositional polymers as exemplified in FIG. 2a.

Example 2. Encapsulation and In Vitro of Doxorubicin in Dex-b-PLA NPs Via Nanoprecipitation The encapsulation of Doxorubicin in the Dex-b-PLA NPs was accomplished using nanoprecipitation method. Dex-b-PLA and Doxorubicin were both dissolved in DMSO (Dex-b-PLA concentration of 7 mg/mL, with varying drug concentrations). 1 mL of the DMSO solution is added drop-wise into 10 mL of water under stirring and continued to stir for additional 30 minutes. The NPs in water were filtered through syringe filter (pore size=200 nm) to remove the drug aggregates and subsequently filtered through Amicon filtration tubes (MWCO=10 kDa, Millipore) to further remove any remaining free drugs in the suspension. The filtered NPs containing encapsulated Doxorubicin were resuspended and diluted in DMSO. Consequently, the drug loading (wt %) in the polymer matrix was calculated by measuring concentration of the Doxorubicin in the mixture by obtaining the absorbance of the solution at 480 nm using Epoch Multi-Volume Spectrophotometer System (Biotek). The measurements were obtained in triplicates (n=3, mean±S.D). The absorbance measured from same procedure using the polymers without the drugs was used as the baseline. The absorbance was correlated with the concentration of the Doxorubicin in DMSO by using standard calibration obtained. The same procedure was used for PLGA-PEG to encapsulate Doxorubicin for comparative analysis. The encapsulation efficiency (%) and drug loading (wt %) were calculated using the two equations (Eq. 1 and Eq. 2).

$$\text{Encapsulation efficiency (\%)} = \frac{\text{mass of drug encapsulated}}{\text{mass of initial drug feed}} \times 100\% \quad (1)$$

$$\text{Drug loading (wt \%)} = \frac{\text{mass of drug encapsulated}}{\text{mass of the nanoparticle}} \times 100\% \quad (2)$$

Figure 3:
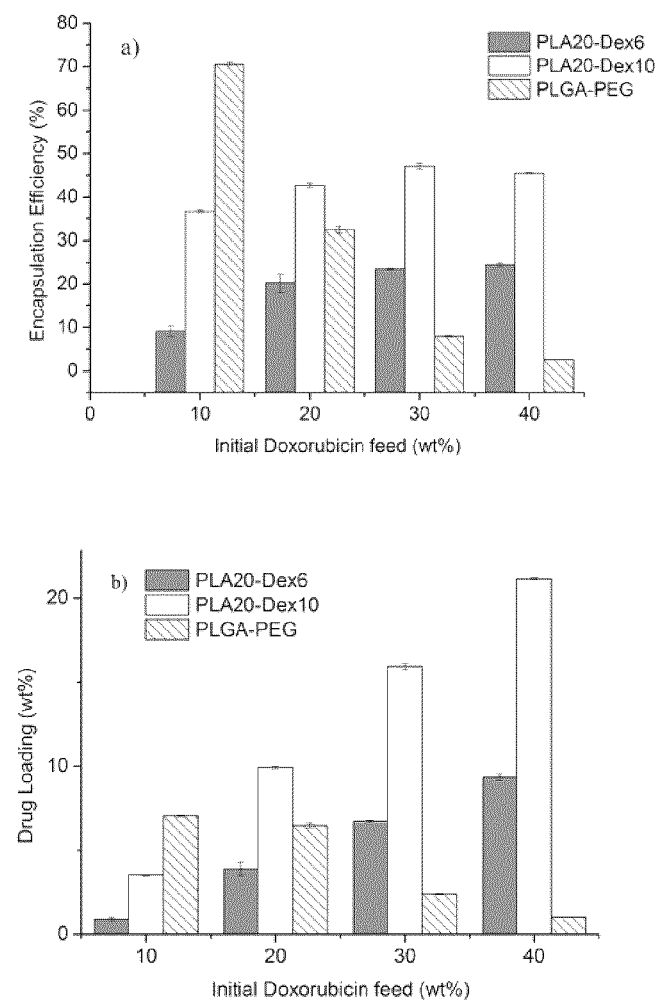
FIG. 3 is a graph of drug encapsulation in NPs: a) Doxorubicin encapsulation efficiency in Dex-b-PLA and PLGA-PEG NPs using nanoprecipitation and b) the corresponding drug loading wt %. Solid gray columns are for PLA20-Dex6 NPs, solid white columns are for PLA20-Dex10 NPs and columns with diagonal lines pattern are for PLGA-PEG NPs (n=3; mean±S.D).

Based on the size tuning as shown in FIG. 2, PLA20-Dex10 (MWPLA~20 kDa, MWDextran~10 kDa) and PLA20-Dex6 were selected for analyzing the encapsulation efficiencies and the drug loading using Doxorubicin as a model hydrophobic drug (FIG. 3). The particle sizes for PLA20-Dex10 and PLA20-Dex6 were 20.5 and 30.1 nm respectively. Doxorubicin compounds were incorporated into NPs through nanoprecipitation method. Both Dextran based NPs, PLA20-Dex10 and PLA20-Dex6 NPs, were found to encapsulate large amounts of Doxorubicin with maximum loadings of 21.2 and 10.5 wt % respectively. The maximum loadings were achieved at 40 wt % initial loading, and further increase in the initial loading did not increase the drug loading in the NPs due to aggregation of the particles. It is speculated that PLA20-Dex10, with longer Dextran chain than PLA20-Dex6, is likely to have more Doxorubicin weakly associated on the NP surface or encapsulated near the surface of the NPs during nanoprecipitation. This effect was minimized by conducting ultrafiltration (MWCO=10 kDa) after the nanoprecipitation ensuring that the non-specifically bound drugs were removed from the NP suspension. The maximum drug loading in PLGA-PEG NPs, used as a control, was found to be 7.1 wt %. It was found that excess initial loading caused more drug precipitation and particle aggregation during nanoprecipitation for PLGA-PEG NPs, whereas Dex-b-PLA NPs showed negligible size increases even at their maximum drug loading. The maximum Doxorubicin loading achieved with PLA20-Dex10 NPs were considerably higher than the most reported values using PEG based NPs in the literatures, which varied over 4.3-11.2% for poly(ε-caprolactone)-PEG copolymers (Shuai 2004; He 2010), 8.7% for poloxamer 407 and PEG hydrogel system (Missirlis 2006), and 18% for PEG-poly(β-benzyl-L-aspartate) based NPs (Kataoka 2001). The increased drug loading is most likely due to the greater hydrophilicity of Dextran compared to PEG (Alpert 1990), which in turn reduces the probability of Dextran chains from the block copolymers associating in the hydrophobic core of the NPs. The encapsulation efficiency and the total drug payload using the Dex-b-PLA system is comparable to commercially available liposomal systems such as the FDA approved Doxil®, which has a drug loading of 12.5% and DaunoXome®, which has Daunorubicin loading of 7.9% (Drummond 1999). The concentration of Doxorubicin in the Doxil® formulation translates into 6.25 mg/m² when Doxil® is administered at 50 mg/m² (Drummond 1999; Safra 2000). The same physiological concentration of Doxorubicin can theoretically be achieved using only 30 mg/m² of PLA20-Dex10 NP-Doxorubicin formulation.

Example 3. In Vitro Release of Doxorubicin from Dex-b-PLA NPs

Using the procedure described in the previous example, drug encapsulated NPs were prepared and filtered to remove non-encapsulated drug aggregates. A purified sample of NPs-drug suspension was collected to measure the maximum absorbance and this was used as the 100% release point. Subsequently, the NP-drug suspension was injected into a Slide-a-Lyzer Dialysis cassette (MWCO=20 kDa, Fisher Scientific) and dialyzed against 200 mL of phosphate buffered saline (PBS, pH 7.4) at 37° C. under mild stirring. At predetermined time intervals, 1 mL of the release medium was extracted and the same volume of fresh new PBS was added to the release medium. The extracted release medium was used to perform UV-Vis absorption measurements at 480 nm in triplicates (n=3, mean±S.D). The release medium was replaced several times to maintain the concentration of Doxorubicin in the medium below 3 µg/mL and to stay below the solubility limit of the Doxorubicin in PBS. Replacing the medium was also expected to prevent the adhesion of released Doxorubicin to the glass walls of the beaker or the magnetic stir bar. The release of Doxorubicin from PLGA-PEG was also obtained with identical procedure for comparative analysis. Free Doxorubicin, without any polymers, release was also observed using the same procedure and all three release profiles from the NPs were normalized using the free Doxorubicin release data along with encapsulation efficiency data. This normalization resulted in a release curve for only encapsulated Doxorubicin. All experiments were performed in dark environment, and the beakers were sealed with Parafilm to prevent evaporation of PBS.

Figure 4:
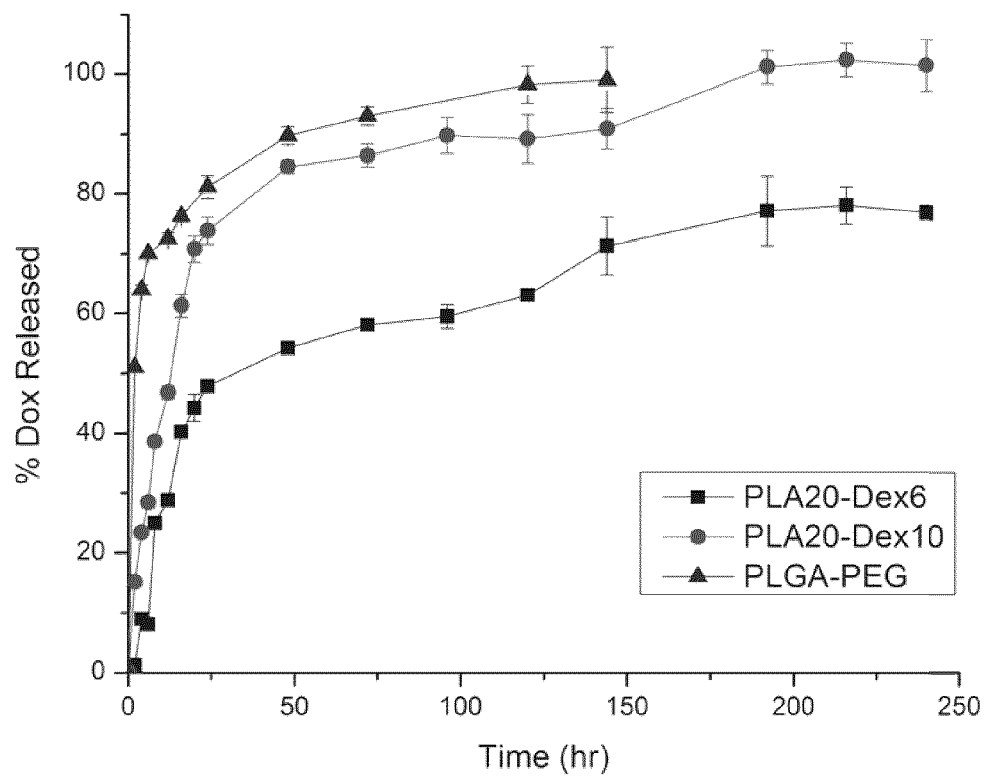
FIG. 4 is a graph of in vitro Doxorubicin cumulative release profiles from Dex-b-PLA and PLGA-PEG NPs conducted in PBS at 37° C. Solid square (■) are for PLA20-Dex10, solid circles (●) are for PLA20-Dex6 and solid triangles (▲) are for PLGA-PEG NPs (n=3; mean±S.D).

The in vitro release of Doxorubicin from the NPs was carried out in pH 7.4 PBS buffer at 37° C. As shown in FIG. 4, the release profile of Doxorubicin from NPs was characterized with an initial burst followed by a sustained-release phase. It is possible that the burst-release region corresponds to drugs non-specifically bound on the surface of the NPs, or drugs encapsulated near the surface of the NPs during the nanoprecipitation procedure (Magenheim 1993). PLA20-Dex6 and PLA20-Dex10 NPs exhibited burst-release region within the initial 24 hours, releasing up to 48% and 74% respectively. The subsequent sustained-release phase of Doxorubicin from PLA20-Dex6 and PLA20-Dex10 NPs continued for 192 hours with similar rate of release from both NPs. The sustained-release phase may correspond to the diffusional release of the drugs from the core of the NPs. In the control study using PLGA-PEG NPs, the burst-release phase of Doxorubicin was within the first 6 hours while steady-release phase continued up to 96 hours, similar to what has been reported previously (Esmaeili 2008).

Example 4. Hemolysis Assay

Dex-b-PLA NPs were purified by using Amicon filtration tubes (MWCO=10 kDa) and centrifugation at 4100 rpm for 30 minutes. A concentration range of NPs was obtained by this process. These NPs were then incubated at 37° C. for one hour with 200 µL of sheep erythrocytes with red blood cells concentration of 1×10⁸ cells/mL to obtain a final volume of 1 mL per sample. The percent hemolysis was calculated by measuring the absorbance at 415 nm and using the absorbance at 500 nm as the baseline. The measurements were conducted in triplicates (mean±S.D). Here, VBS solution was used as the negative control and deionized water was used as the positive control. PLGA-PEG NPs were also prepared and tested in a similar manner for comparison.

Figure 5:
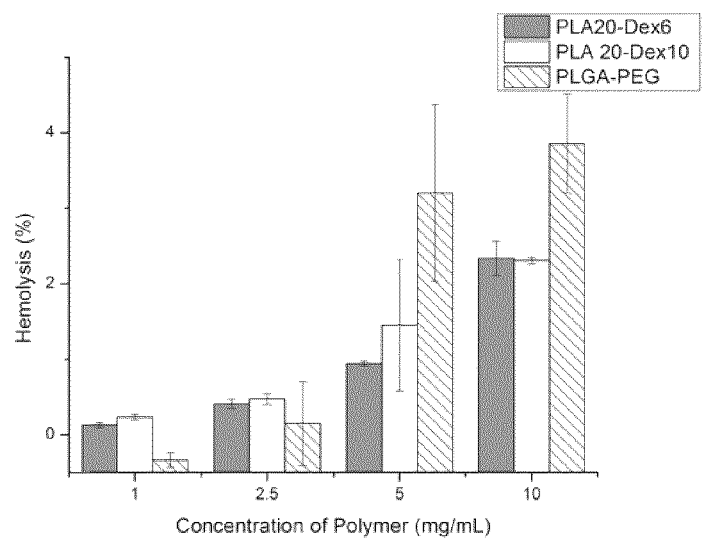
FIG. 5 is a graph of hemolytic activity of Dex-b-PLA and PLGA-PEG NPs for concentrations relevant to theoretical administered dose in blood. VBS was used as a negative control and deionized water was used as positive control in sheep erythrocytes. Solid gray columns are for PLA20-Dex6 NPs, solid white columns are for PLA20-Dex10 NPs and columns with diagonal lines pattern are for PLGA-PEG NPs (n=3; mean±S.D).

Previous work has considered hemolysis of NPs less than 5% to be biocompatible (Dobrovoiskaia 2008). It has been demonstrated that PLGA NPs stabilized by surfactants are severely hemolytic to 80% and hemolysis is reduced considerably by using a hydrophilic PEG surface in the case of PLGA-PEG NPs (Kim 2005). The same results were expected from the use of Dextran based NP formulation since Dextran derivatives such as diethylaminoethyl-dextran have low (~5%) hemolysis (Fischer 2003). The block copolymer NPs formulated previously were tested for hemolytic activity at various concentrations (1-10 mg/mL). It was shown that all formulated NPs were not significantly hemolytic (<5%) up to a concentration of 10 mg/mL in the blood (FIG. 5). The hemolysis by both PLA20-Dex6 and PLA20-Dex 10 were similar since they have the same component polymers. For comparison, Doxil® (a liposomal formulation of doxorubicin) is usually administered at the dose of 50 mg/m$^2$ (Safra 2000). This dose translates to a concentration of 0.018 mg/mL in blood for an average human being (body surface area 1.79 m$^2$ (Sacco 2010), and blood volume 5 L) (Kusnierz-Glaz 1997). The tested hemocompatible concentration (10 mg/mL) for PLA-b-Dex NPs is considerably higher than the administered dose of Doxil®. This suggests that PLA-b-Dex NPs are a safe system for intravenous administration.

Example 5. Pharmacokinetics and Biodistribution of Dex-b-PLA NPs

To ensure that all radioactivity administered to rats was associated with the particles, tritium [$^3$H]-PLA-radiolabeled nanocrystals were washed and purified in methanol prior to NP formation. Albino Wistar rats, body weight between 200 and 250 g, were fasted overnight but had free access to water. 200 μL of the NP formulations were prepared in NaCl 0.9% and injected intravenously into the tail vein at a dose of approximately 30 mg/kg. Blood (approximately 200 μL) was collected in heparinized microcentrifuge tubes by controlled bleeding of hind leg saphenous veins at the indicated time intervals. To characterize the biodistribution of NPs, rats were euthanized at 24 h after NP injections. Approximately 200 μL of blood was drawn by cardiac puncture from each mouse. Organs including heart, lungs, liver, spleen and kidneys were harvested from each animal as described previously (Gu 2008). The $^3$H content in the tissue and blood were assayed in a Wallac 1414 Liquid Scintillation Counter.

Figure 6:
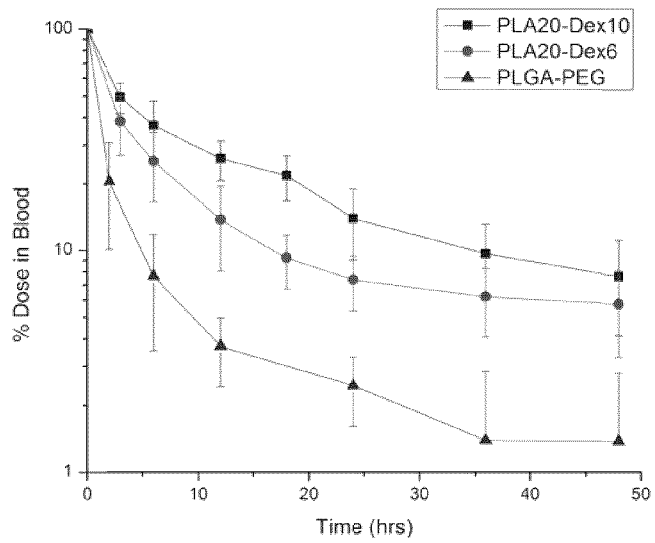
FIG. 6 is a graph illustrating pharmacokinetic profiles of Dextran-b-PLA and PLGA-PEG NPs administered at 30 mg/kg i.v. to rats. The NP concentration in blood was tracked using [3H]-PLA-radiolabeled nanocrystals. Solid square (■) are for PLA20-Dex10, solid circles (●) are for PLA20-Dex6 and solid triangles (▲) are for PLGA-PEG NPs (n=5, mean±S.D).
Figure 7:
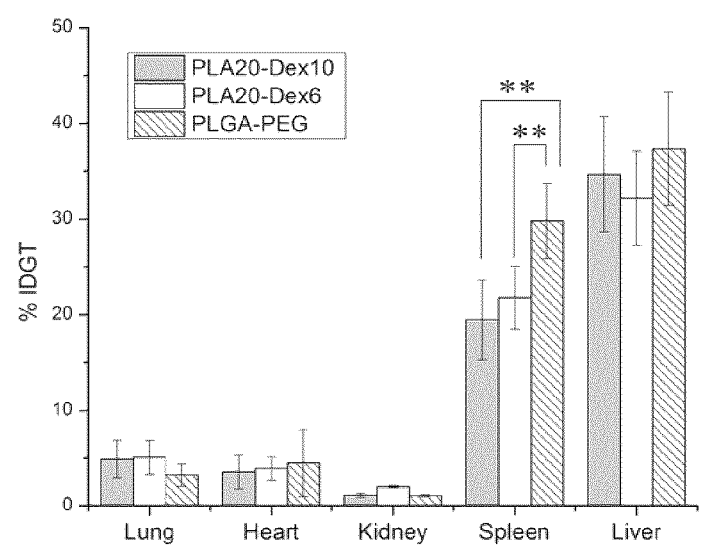
FIG. 7. Is a graph illustrating biodistribution of Dextran-b-PLA and PLGA-PEG NPs in various organs in rats 24 hour post-injection. Solid gray columns are for PLA20-Dex6 NPs, solid white columns are for PLA20-Dex10 NPs and columns with diagonal lines pattern are for PLGA-PEG NPs (n=5, mean±S.D)**: $p<0.01$.
Figure 8:
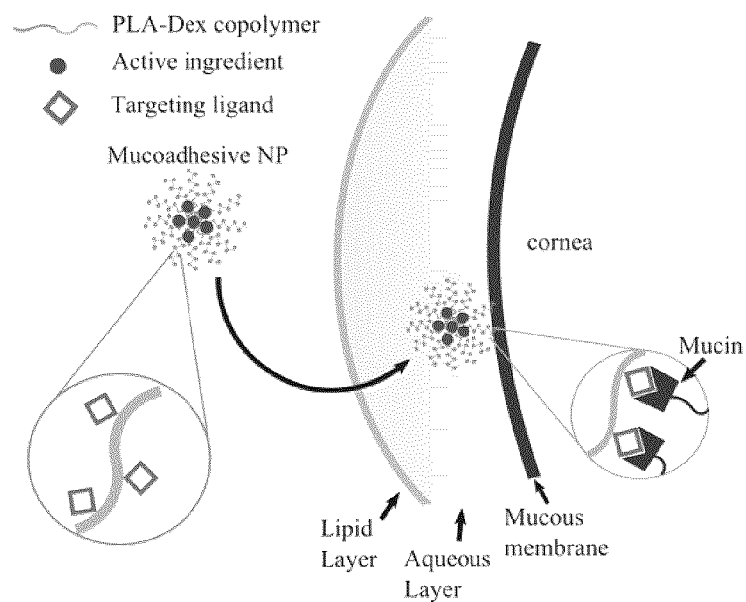
FIG. 8 is a schematic illustration of mucoadhesion using particulates onto ocular mucosa to circumvent the clearance mechanisms such as tear dilution and tear turnover. Mucoadhesive agents are present throughout the surface of the nanoparticle carriers.
Figure 9:
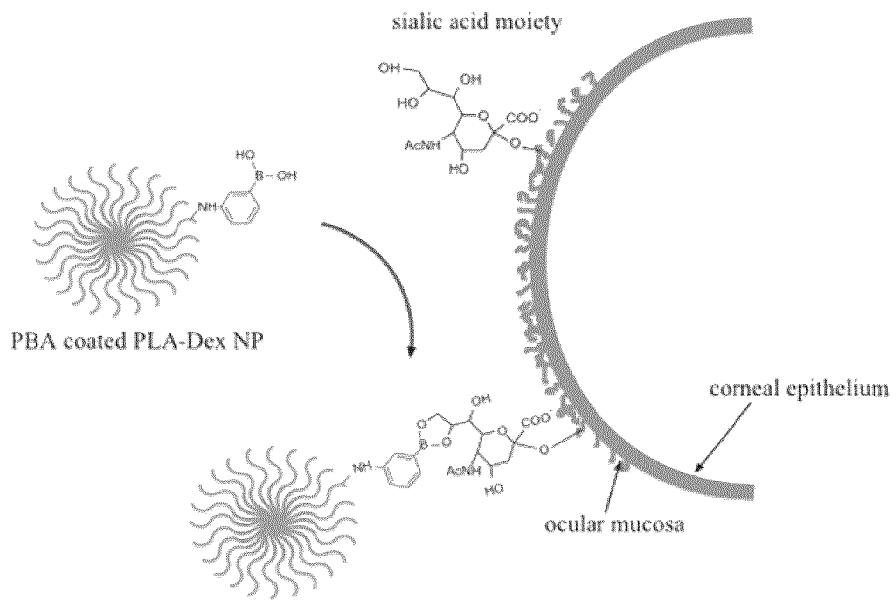
FIG. 9 is a schematic illustration of mucoadhesion of PBA modified Dextran-b-PLA NPs onto sialic acid residues present on ocular mucosa to circumvent the clearance mechanisms such as tear dilution and tear turnover.
Figure 10:
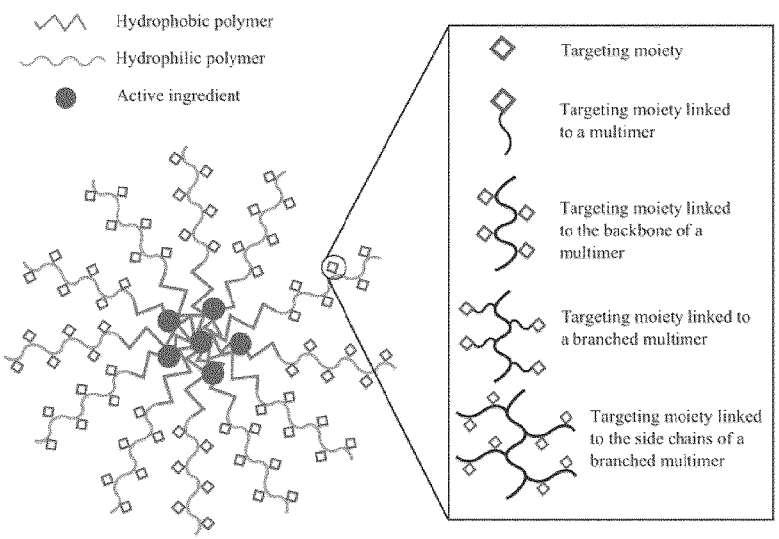
FIG. 10 is a schematic illustration of the structure of the mucoadhesive nanoparticles with variations of targeting moieties on the surface of the nanoparticles. The presence of multiple sites for conjugation of targeting moiety to the surface of the nanoparticle provides a high degree of tunability for targeting.
Figure 11:
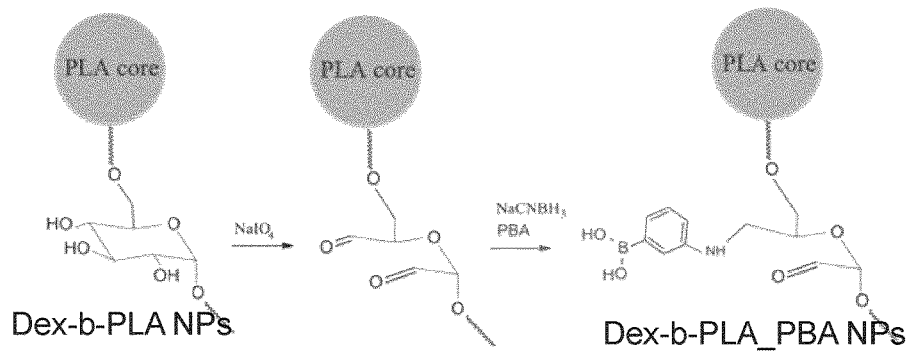
FIG. 11 is a schematic illustration of one embodiment showing the surface modified the NPs with PBA using two-step approach: periodate oxidation of the Dextran, and conjugation of the aldehyde groups on the oxidated Dextran with amine groups of PBA.

The NP circulation half-life in vivo was characterized by measuring the amount of tritium [$^3$H]-PLA-radiolabeled nanocrystals that were incorporated in the NP formulations. FIG. 6 shows NP concentration in blood circulation at predetermined time intervals after intravenous administration. It is noted that the time-dependent NP concentration in the blood were characterized by two regions of distinct slopes. The first region (first ~18 hrs) corresponds to the initial clearance of the NPs from the blood circulation, whereas the second region indicates the terminal clearance of the NPs. The former region profiles the NP volume of distribution among vascular and extravascular tissues, while the terminal half-life relates to the systemic clearance phase of the NPs from the body (Yang 2009). The initial half-life ($t_{1/2}$), terminal half-life ($t_{z1/2}$), the blood retention time for 90% of the NPs ($t_{0.9}$), and AUC (Gaucher 2009) of the three NPs are summarized in Table 1. At 24 hours postinjection, rats were euthanized, and the major organs were harvested from the animals to evaluate the biodistribution of the NPs (FIG. 7). It was observed that all three NPs had maximum accumulation in the liver and the percent distribution was similar for each NP. Higher accumulations in the spleen were observed with PLGA-PEG NPs compared to both of Dex-b-PLA NPs (p<0.01). Accumulation of NPs in all other organs was below 5% with similar amount of accumulation among the NPs in each organ.

Although all three types of NPs showed similar $t_{z1/2}$ values, both PLA20-Dex10 and PLA20-Dex6 NPs showed significantly higher values of $t_{1/2}$, $t_{0.9}$, and AUC compared to that of the model NPs composed of PLGA-PEG. Previous studies mainly focused on $t_{z1/2}$ values for NPs but the present inventors extracted $t_{0.9}$ values for comparison purposes. It was observed that $t_{0.9}$ values were only about 2 hrs for PEG-b-PLA NPs (Gaucher 2009), 6 hrs for polyvinylpyrrolidone based NPs (Gaur 2000) and about 8 hrs for chitosan based NPs (He 2010). Not only do Dex-b-PLA NPs outperform these NPs with a $t_{0.9}$ of 38.3 hrs, they are also comparable to 60 nm PEG-b-PCL system (Lee 2010) and Stealth® liposomes (Allen 1991), both of which have $t_{0.9}$ values over 48 hours. In this study, the longer blood circulation observed in Dex-b-PLA NPs, compared to PLGA-PEG NPs, is believed to be partially due to the size difference. A recent study by Rehor et al. showed that NPs with diameter of 40 nm had longer circulation half-life compared to larger NPs with diameter of 100 nm (Rehor 2008). It is hypothesized that Dex-b-PLA NPs, having smaller sizes than PLGA-PEG NPs, have increased curvature that reduce protein adsorption, which may in turn result in slower clearance rate by the RES. This is further supported by the longer blood circulation time of PLA20-Dex10 compared PLA20-Dex6 since the former has smaller particle size. In addition to their size effect on protein adsorption, it is also hypothesized that the abundant hydroxyl groups on the Dextran surface may induce sufficient hydration layer around the NPs to limit protein adsorption (Portet 2001). It has been reported that accumulation rate in tissues such as spleen increases with increase in the particle sizes (Li 2008) which is consistent with the current findings. It has also been observed that PEG coating in PEGylated particles can increase accumulation in the spleen (Peraccia 1999) whereas the neutrality (Chouly 1996) and flexibility (Passirani 1998) of dextran chains on the NP surface can cause lower protein absorption leading to lower spleen accumulation. Dex-b-PLA NPs are expected to have low complement activation as observed for dextran-poly(methyl methacrylate) NPs, whose behaviour was similar to soluble dextran (Passirani 1998). The lower accumulation of the Dex-b-PLA NPs in spleen along with lower complement activation may have attributed to their longer blood circulation (Meerasa 2011). The long circulation half-life of NP drug carriers is a crucial parameter in cancer therapy since it increases the probability of accumulating at cancerous tissues due to EPR effect: particle size below 100 nm directly promotes accumulation of NPs in the tumor sites since the vascular pores around tumor are at least 100 nm in size (Cho 2008). The size-tuneable Dex-b-PLA system developed here presents a polymeric platform for systematically studying the effect of NP size on various in vivo characteristics such as biocompatibility, blood clearance, tumor accumulation and biodistribution and screening candidates for further clinical evaluation.

TABLE 1

Blood pharmacokinetic parameters for PLA20-Dex10, PLA20-Dex6, and PLGA-PEG NPs

| | $t_{1/2}$ (hr) | $t_{z1/2}$ (hr) | $t_{0.9}$ (hr) | AUC |
|---|---|---|---|---|
| PLA20-Dex10 | 12.3 ± 2.2 | 29.8 ± 1.0 | 38.3 ± 21.5 | 1040 |
| PLA20-Dex6 | 7.2 ± 0.4 | 26.6 ± 3.1 | 17.9 ± 8.6 | 691 |
| PLGA-PEG | 3.7 ± 0.6 | 27.0 ± 2.3 | 5.0 ± 2.4 | 287 |

$t_{1/2}$: initial half-life;
$t_{z1/2}$: terminal half-life;
$t_{0.9}$: blood retention time for 90% of the NPs;
AUC: Area under curve (% dose · hr)

Statistical analysis was performed using the student t-test and statistical significance was assessed with p<0.01.

Example 6. Synthesis and Characterization of Dex-b-PLA-BLA NPs

6.1 Synthesis of Dex-b-PLA

The synthesis of Dex-b-PLA was carried out as described in Example 1 (see also, Verma, 2012). Briefly the procedure for the synthesis of Dex-b-PLA divides into three stages: reductive amination between Dextran and N-Boc-ethylenediamine, deprotection of the Boc group, and conjugation of the amine-modified Dextran end group with carboxyl-terminated PLA. Reductive amination was carried out by dissolving Dex in borate buffer and mixing it with N-Boc-ethylenediamine and $NaCNBH_3$ in dark condition for 72 hrs. After the reaction the mixture is washed with methanol and dried in vacuum desiccator. The sample is then dissolved in $DI-H_2O$ and treated with hydrochloric acid and triethyl amine for the deprotection of the Boc group. The conjugation of amine-terminated Dextran and PLA was carried out in DMSO with EDC and Sulfo-NHS as catalysts for 4 hrs. The final product was washed several times with methanol. The wash sample was further dissolved in acetone and centrifuged. The supernatant was extracted carefully in order to separate from free unreacted Dextran that have been precipitated. Finally the supernatant containing Dex-b-PLA was dried in vacuum desiccator.

6.2 Surface Functionalization of Dex-b-PLA NPs with PBA

Dex-b-PLA was dissolved in DMSO (30 mg/ml), and added slowly into water under mild stirring. Periodate oxidation of the Dextran surface was carried out by adding 60 mg of $NaIO_4$ and stirring for an hour. Subsequently, glycerol was added to quench the unreacted $NaIO_4$. Various amounts of PBA (i.e. 40 mg for Dex-b-PLA_40 PBA) were added to the mixture, along with $NaCNBH_3$, for 24 hours. All reactions were carried out in the dark. The mixture was then dialyzed in water for 24 hrs to remove any unreacted solutes, through changing the wash medium 4 times.

6.3 Characterization of Dex-b-PLA_PBA NPs

The surface modification with PBA was verified using $^1H$ NMR spectroscopy (Bruker 300 MHz). Dex-b-PLA_PBA polymers were dissolved in DMSO-d6 (25 mg/ml) for the $^1H$ NMR characterization. UV-Vis absorption measurement at 291 nm was performed with Epoch Multi-Volume Spectrophotometer System (Biotek, USA) on the Dex-b-PLA_PBA in order to quantify the amount of PBA attached to the Dextran chains. Dex-b-PLA solution with same concentration was used as the baseline for UV-vis absorption study. The NPs of Dex-b-PLA_PBA prepared using nanoprecipitation were also analyzed using 90Plus Particle Size Analyzer (Brookhaven, $\lambda=659$ nm at 90°) obtaining volume-averaged multimode size distribution (MSD) mean diameter. The particle size and morphology of Dex-b-PLA_PBA NPs were further confirmed verified using TEM (Philips CM10) with the accelerating voltage of 60 kV and the Lanthanum Hexaboride filament (LaB6). 300 Mesh Formvar coated copper grids (Canemco & Marivac) were used for this experiment. The NP suspension in water was prepared using the nanoprecipitation method as mentioned above. A drop of the NP suspension was placed onto the grid, and the grid was briefly stained with aqueous phosphotungstic acid solution (2 w/v % in water). The copper grid with the NP suspension was dried under ambient environment overnight before imaging under TEM.

Figure 12A:
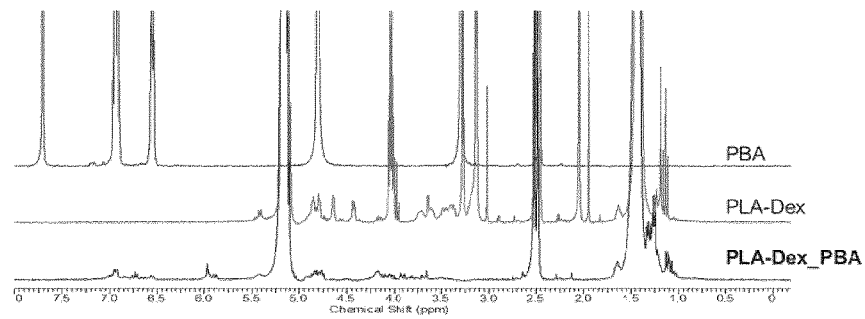
FIG. 12a demonstrates $^1$H NMR verification of the presence of PBA on the Dex-b-PLA polymer chains.

The NMR spectrum of Dex-b-PLA_PBA shows peaks corresponding to both PLA (multiplets at 5.2 ppm) and Dextran (multiplets at 4.86 ppm), while also showing multiplet peaks at 6.6 ppm and 6.9 ppm, which correspond to the protons from carbon 2 to 6 in the phenyl group of the PBA (FIG. 12a). UV absorption at 291 nm was measured to quantify the amount of PBA on the NPs with respect to the Dextran monomers. Increasing the amount of PBA in the initial reaction mixture proportionally increased the final PBA conjugation on the Dextran surface (Table 2) with the highest density of 34.6 mol % (equivalent of about 3.5 PBA conjugated per 10 Dextran monomers) achieved for Dex-b-PLA_320PBA NPs.

Figure 13:
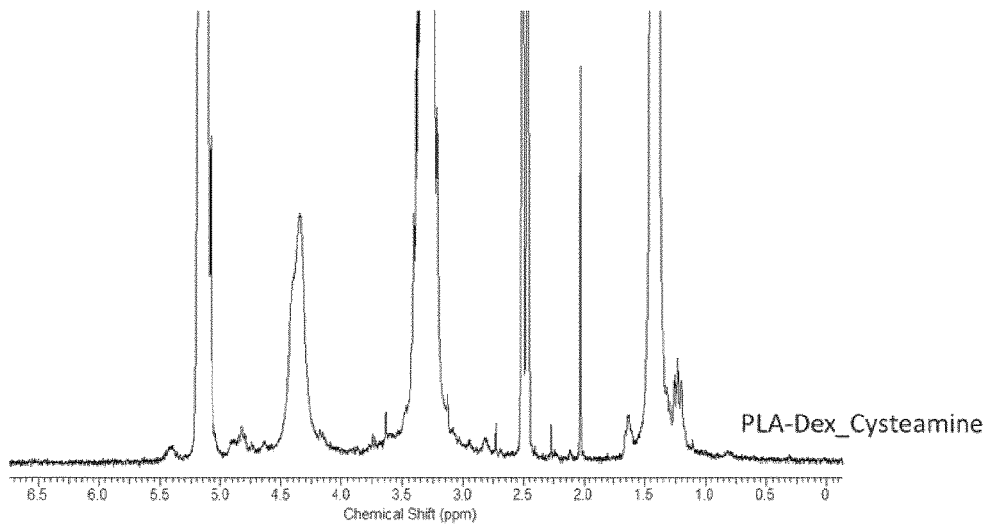
FIG. 13 demonstrates $^1$H NMR verification of the presence of cysteamine on the Dex-b-PLA polymer chains which would expose thiol groups on the surface of the NPs.
Figure 14:
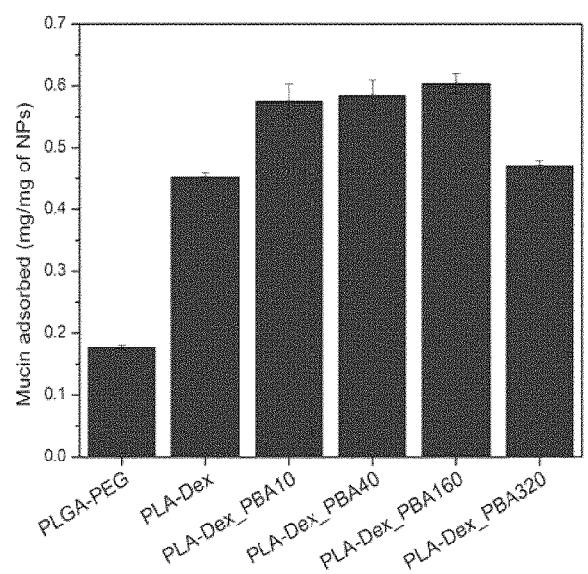
FIG. 14 demonstrates the enhanced mucoadhesion property, measured using PAS staining method, of the Dex-b-PLA NPs after surface modified with PBA.

Conjugation of Cysteamine onto the Dex-b-PLA NP surface was also demonstrated using $^1H$ NMR spectrum (FIG. 13). The peaks that correspond to the protons on carbon 1 and 2 of the cysteamine are shown as multiplets peaks near 2.7 ppm. However, higher resolution NMR characterization is required in the future to further differentiate the peaks from other noise peaks from the polymer.

Figure 12B:
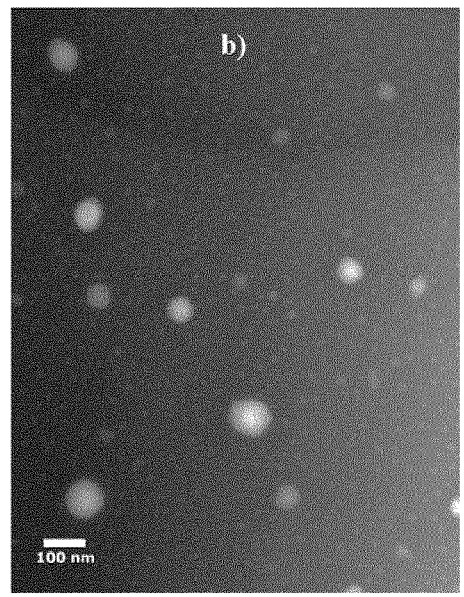
FIG. 12b demonstrates the spherical morphology of the Dex-b-PLA_PBA NPs.

The sizes and morphology of the nanoparticles were analyzed using the procedure illustrated in Example 1. The sizes of the NPs were in the range of 25 to 28 nm, which are smaller than the unmodified NPs of 47.9 nm. Without being bound by theory, it is postulated that the particle size reduction is attributed by the PBA molecules causing the Dextran chains to be less hydrophilic, leading them to form more compact shells around the PLA particle core. TEM images confirmed a spherical morphology, due to the formation of a core-shell structure of the amphiphilic block copolymers (FIG. 12b). The sizes of Dex-b-PLA_PBA NPs obtained are smaller than that normally achieved with PEG-based block copolymers such as PLGA-PEG (Karnik, 2008). We postulate that smaller NPs may be more desirable for mucoadhesion, since they provide greater surface area for interaction with the mucous membrane.

Example 7. Drug Encapsulation in Dex-b-PLA_PBA NPs

Figure 15:
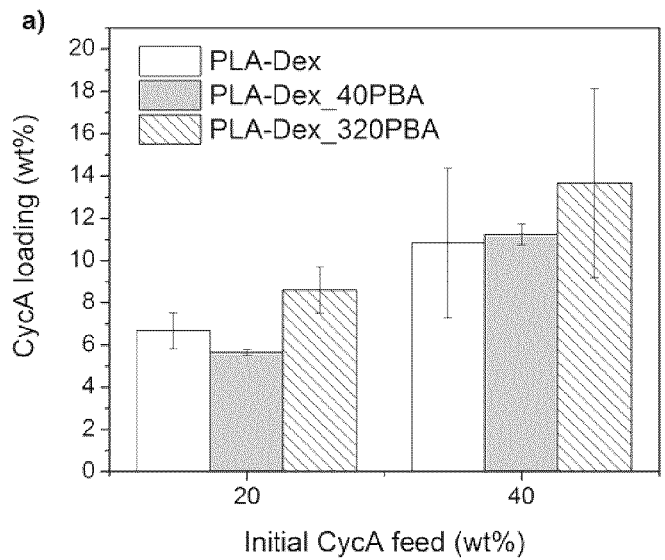
FIGS. 15 and 16 demonstrate the ability of the Dex-b-PLA_PBA NPs to load up to 13.7 wt/wt % of the drug Cyclosporine A, and their ability to release them in a sustained manner for up to 5 days in in vitro experiment.

The Cyclosporine A (CycA) encapsulation in the Dex-b-PLA and Dex-b-PLA_PBA NPs were measured using the procedure described in 0. Maximum encapsulation of CycA was achieved at an initial feed of 40 wt/wt %: Dex-b-PLA NPs encapsulated up to 10.8 wt/wt %, whereas Dex-b-PLA_40 PBA and Dex-b-PLA_320 PBA encapsulated up to 11.2 and 13.7 wt/wt %, respectively (FIG. 15). The 13.7 wt/wt % encapsulation is equivalent to 2.38 µg of CycA in 28 µL formulation (which is the same as the administration volume of commercially available RESTASIS®), whereas the commercial product contains 14 µg. Therefore, a therapeutically relevant dosage can be achieved by simply adjusting the polymer and drug concentration in the formulation.

Figure 17:
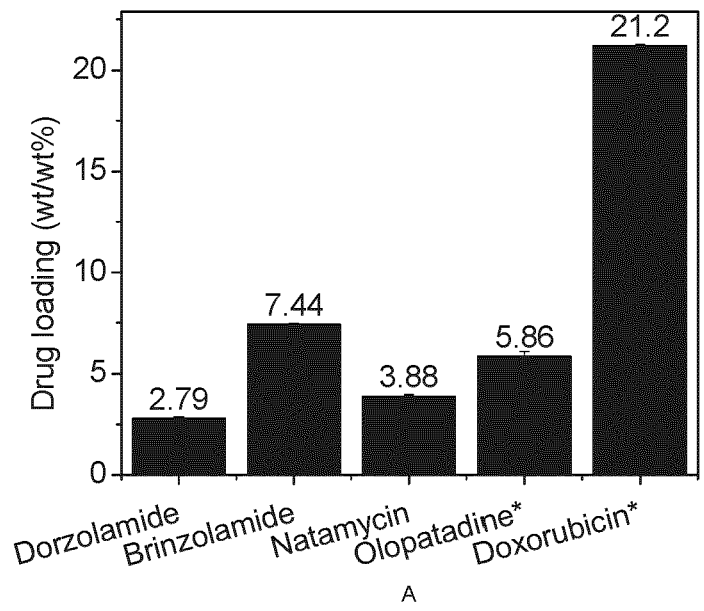
FIG. 17 demonstrates the ability of Dex-b-PLA NPs to encapsulate various bioactive agents. Olopatadine and Doxorubicin were encapsulated in Dex-b-PLA NPs. Dorzolamide, Brinzolamide, and Natamycin were encapsulated in the Dex-b-PLA_PBA NPs.
Figure 18:
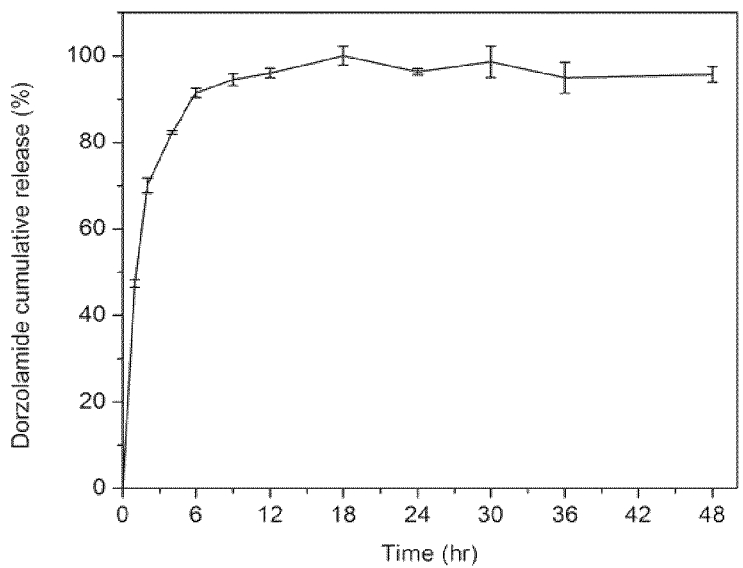
FIG. 18 demonstrates the ability of the Dex-b-PLA_PBA NPs to release Dorzolamide (used in treatment of glaucoma) in a sustained manner for up to 18 hours in in vitro experiment. The NPs were able to load up to 2.8 wt/wt % Dorzolamide.
Figure 19:
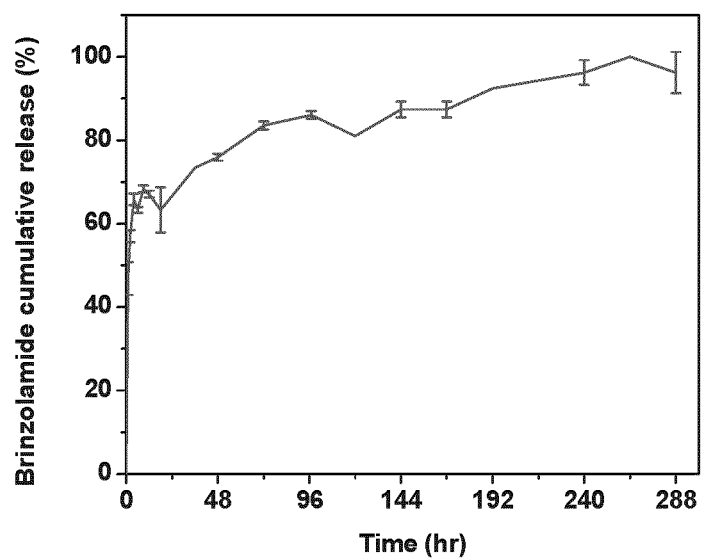
FIG. 19 demonstrates the ability of the Dex-b-PLA_PBA NPs to release Brinzolamide (used in treatment of glaucoma) in a sustained manner for up to 11 days in in vitro experiment. The NPs were able to load up to 6.54 wt/wt % Brinzolamide.
Figure 20:
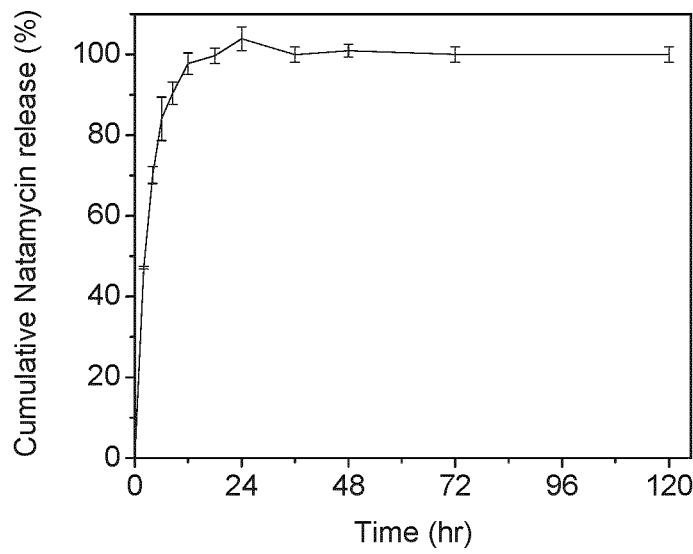
FIG. 20 demonstrates the ability of the Dex-b-PLA_PBA NPs to release Natamycin (used in treatment of ocular fungal infection) in a sustained manner for up to 24 hours in in vitro experiment. The NPs were able to load up to 3.88 wt/wt % Natamycin.
Figure 21:
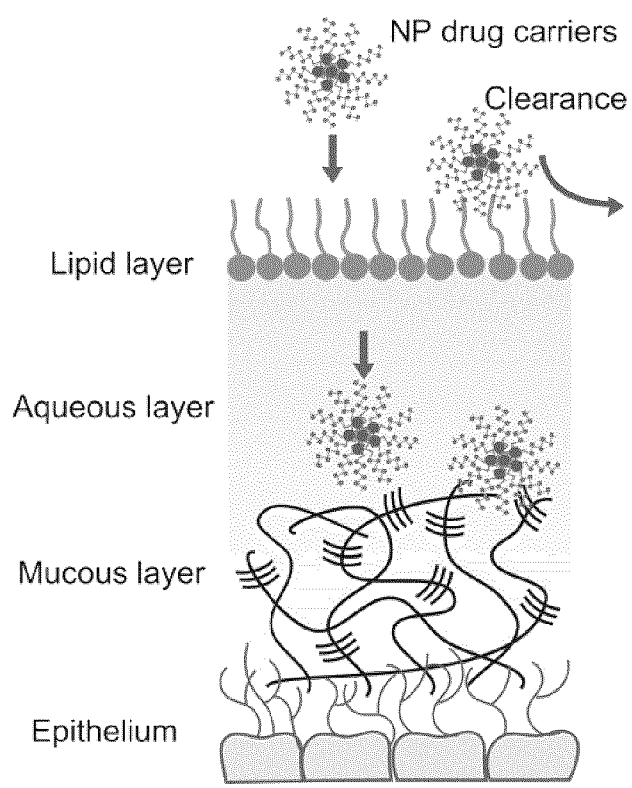
FIG. 21 is a schematic illustration of the partition of nanoparticle carriers across tear fluid lipid layer.
Figure 22:
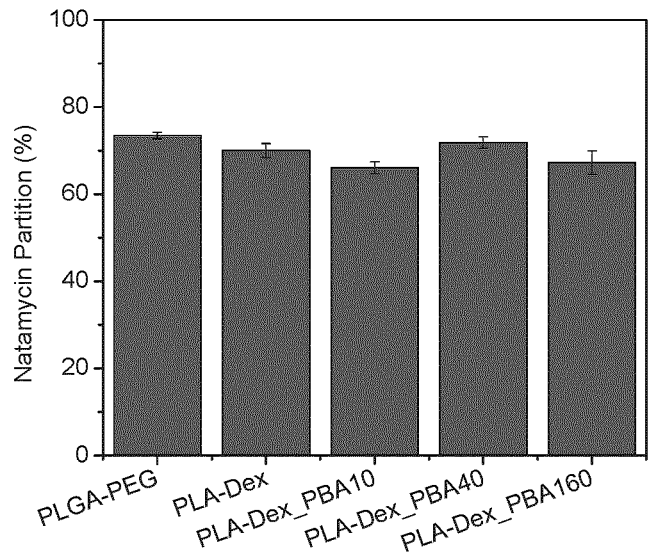
FIG. 22 demonstrates that these various types of nanoparticle carriers are capable of achieving high percentage partition across the tear fluid lipid layer.

Encapsulation of other types of bioactive agents in the Dex-b-PLA_PBA NPs has also been explored (FIG. 17). In one embodiment the bioactive agent is Dorzolamide, which is commonly used to treat glaucoma. In another embodiment the bioactive agent is Brinzolamide, which is also used to treat glaucoma. Natamycin, which is an antifungal agent, is also used as a bioactive agent in the encapsulation in the Dex-b-PLA_NPs. In other embodiments, Doxorubicn, an anti-cancer agent, and Olopatadine, antihistamine, were also explored in the encapsulation in the PLA-Dex NPs.

The encapsulation of Cyclosporine A (CycA) in the Dex-b-PLA NPs was accomplished using nanoprecipitation method. Dex-b-PLA and CycA were both dissolved in DMSO (Dex-b-PLA concentration of 7 mg/mL, with varying drug concentrations). 1 mL of the DMSO solution is added drop-wise into 10 mL of $DI-H_2O$ under mild stirring and continued to stir for additional 30 minutes. The NPs in water were filtered through syringe filter (pore size=200 nm) to remove the drug aggregates and subsequently centrifuged using Amicon filtration tubes (MWCO=10 kDa, Millipore) to further remove any remaining free drugs in the suspension. The filtered NPs containing encapsulated CycA were resuspended and diluted in Acetonitrile. Consequently, the drug loading (wt/wt %) in the polymer matrix was calculated by measuring concentration of the CycA in the mixture using High-performance liquid chromatography (HPLC, Thermo Scientific). The measurements were obtained in triplicates (n=3, mean±S.D). The absorbance measured from same procedure using the polymers without the drugs was used as the baseline. The measurements were converted to the concentration of the CycA using standard calibration obtained.

The encapsulation of Dorzolamide, Brinzolamide, and Natamycin in the Dex-b-PLA NPs were accomplished using the same method. The characterization of these drugs was performed using Multi-Volume Spectrophotometer System (Biotek, USA) instead of HPLC.

Example 8. Drug Release from Dex-b-PLA_PBA NPs In Vitro

Figure 16:
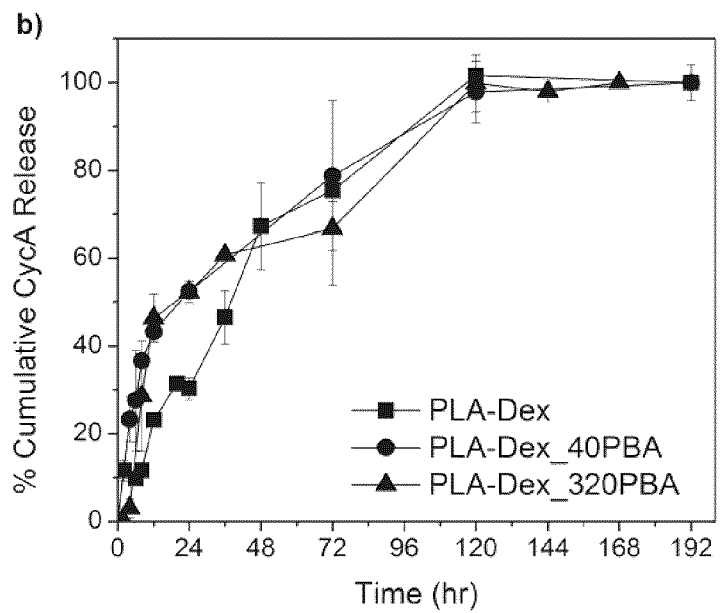

The in vitro release phenomenon of CycA from the Dex-b-PLA NPs were analyzed using the procedures described in 0. Both Dex-b-PLA and Dex-b-PLA_PBA NPs (Dex-b-PLA_40 PBA and Dex-b-PLA_320 PBA) showed a total release point at around 120 hrs (FIG. 16), which is significantly longer than previous studies involving in vitro release of CycA from micro or nanoparticles which showed up to 48 hours of sustained release (Li, 2012; Shen, 2010; Shen, 2010; Yuan, 2006). Moreover, the release rate may potentially be a significant improvement over the commercial product, which requires administering twice a day. Whereas Dex-b-PLA NPs demonstrated a sustained release rate for up to 120 hours, Dex-b-PLA_PBA NPs showed two regions of slightly different release rate. In the first 48 hrs, the Dex-b-PLA_PBA NPs released CycA at a faster rate compared to Dex-b-PLA NPs, which may be due to the release of CycA that were encapsulated near the slightly more hydrophobic surface Dex-b-PLA_PBA NPs. The subsequent slower release rate, compared to Dex-b-PLA NPs, may be due to the release of drugs from the core of the Dex-b-PLA_PBA NPs, which need to diffuse through the more compact Dextran surface. When the volume of PBA modified NP formulation were scaled to the administration volume of RESTASIS® (28 μL), the CycA release rates were in the range of μg/day, which is similar to the daily administration dosage of CycA in RESTASIS®. Therefore, it is possible to optimize the formulation by changing the concentration of the PBA modified NPs and/or the amount of CycA to achieve a clinically effective release rate and amount.

In vitro CycA release phenomena from both PBA modified and unmodified Dex-b-PLA NPs in the STF at 35° C. were analyzed by quantifying the CycA in the STF at predetermined time intervals using High Performance Liquid Chromatography (HPLC). Using the procedure described in the previous section, drug encapsulated NPs, both Dex-b-PLA and Dex-b-PLA_PBA, were prepared and filtered to remove non-encapsulated drug aggregates. A purified sample of NPs-drug suspension was collected to measure the maximum absorbance and this was used as the 100% release point. Subsequently, the NP-drug suspension was injected into a Slide-a-Lyzer Dialysis cassette (Molecular weight cut-off=20 kDa; Fisher Scientific, Canada) and dialyzed against 200 mL of simulated tear fluid (STF) at 35° C. under stirring. At predetermined time intervals, 1 mL of the release medium was extracted and the same volume of fresh new STF was added to the release medium. The extracted release medium was characterized using HPLC method (n=3, mean±S.D). The release medium was replaced several times to maintain the concentration of CycA in the medium in order to stay below its solubility limit in water. Replacing the medium was also expected to prevent the adhesion of released CycA to the glass walls of the beaker or the magnetic stir bar. The beakers were sealed with Parafilm to prevent evaporation of water.

The in vitro release study of Dorzolamide, Brinzolamide, and Natamycin in the Dex-b-PLA NPs were accomplished using the same method. The characterization of these drugs was performed using Multi-Volume Spectrophotometer System (Biotek, USA) instead of HPLC.

Example 9. Mucoadhesion Tests 9.1 In Vitro Mucoadhesion Test—Zeta Potential

Zetapotential measurements were used to analyze the interaction between mucin particles and the NPs using the procedures described in 0. Several reports in the past have used zeta potential to assess the mucoadhesive properties of drug carriers (Khutoryanskiy, 2011; Shaikh, 2011; Sogias, 2008; du Toit 2011; Takeuchi, 2005). Mucin particles at physiological pH exhibit overall negative surface charge due to the presence of carboxylate groups (sialic acid) and ester sulfates at the terminus of sugar units (Khutoryanskiy, 2011). By adhering to the sialic acid moieties of the mucin particles, the Dex-b-PLA_PBA NPs may shield the negative charges from the surface of the mucin particles and also cause aggregation of the mucin particles, thus increasing the overall surface charge. Only Dex-b-PLA_160 PBA (22.9 mol % PBA) and Dex-b-PLA_320 PBA NPs (34.6 mol %) showed significant interaction with mucin particles compared to the control study (Table 2). Low PBA surface functionalization densities do not appear to show a difference compared to unmodified NPs in terms of mucin-NP interaction. It is therefore desirable to use NPs with abundant surface functional groups, such as Dextran-based NPs, to tune the functionalization density where maximum mucoadhesion is desired. If one was to functionalize the surface of PLGA-PEG NPs, using one functional group per each PEG chain, the maximum PBA modification can be achieved is only 0.44 mol % (assuming the same MW of PEG, i.e. 10 kDa). An increased amount of PBA functionalization also increased the extent of NP-mucin interaction, which allows potential increase of mucin-NP interaction by saturating PBA on the surface. However, the functionalization of PBA causes the Dextran surface to be more hydrophobic, increasing the potential for aggregation of the NPs. It is therefore ideal to tune the amount of PBA functionalization to achieve optimal mucin-NP interaction without compromising the NP colloidal stability.

TABLE 2

PBA conjugation efficiency and diameter of unmodified and modified Dex-b-PLA NPs

| Formulation | PBA:Dex[a] (mol %) | Diameter (nm) | Zeta potential[b] (mV) |
|---|---|---|---|
| Mucin | | | −11.1 ± 0.1 |
| Dex-b-PLA | 0 | 47.9 ± 0.5 | −10.7 ± 0.6 |
| Dex-b-PLA_10PBA | 2.85 ± 0.03 | 27.5 ± 0.9 | −11.4 ± 0.2 |
| Dex-b-PLA_40PBA | 12.2 ± 0.2 | 26.7 ± 0.1 | −10.8 ± 0.4 |

TABLE 2-continued

PBA conjugation efficiency and diameter of unmodified and modified Dex-b-PLA NPs

| Formulation | PBA:Dex[a] (mol %) | Diameter (nm) | Zeta potential[b] (mV) |
|---|---|---|---|
| Dex-b-PLA__160PBA | 22.9 ± 0.3 | 25.2 ± 1.0 | −9.67 ± 0.76 |
| Dex-b-PLA__320PBA | 34.6 ± 0.2 | 28.1 ± 0.3 | −8.32 ± 0.28 |

[a]Mol % of PBA with respect to Dextran monomers;
[b]NP suspensions are mixed with mucin suspension in PBS To assess the mucoadhesive properties of PBA modified Dex-b-PLA, zeta potential was measured for quantitative analysis of interaction between mucin particles and Dex-b-PLA_PBA NP suspension. 1 w/v % mucin solution was prepared in pH 7.4 PBS by stirring overnight and the solution was subsequently sonicated for 10 minutes (Branson Digital Sonifier 450, USA). To 700 µL of mucin particle solution were added 200 µL of 0.7 mg/ml Dex-b-PLA_PBA NP suspension in PBS. A control study was also performed by adding 200 µL of PBS to the mucin particle solution. The zeta potential of mucin particles with the NP suspension and the control study were determined using a Malvern Zeta-Sizer Nano ZS90 (Malvern Instruments, Worcestershire, U.K.).

9.2 In Vitro Mucoadhesion Test—PAS Staining Method

Mucoadhesion of the NPs was measured using the in vitro PAS staining method as described above. Compared to the Dex-b-PLA and the PLGA-PEG NPs, the Dex-b-PLA_PBA NPs showed increased mucin adsorption (Table 2). Dex-b-PLA_10 PBA, Dex-b-PLA_40 PBA, and Dex-b-PLA_160 PBA NPs showed a linear increase in mucin adsorption from 0.575 to 0.605 mg/mg of NPs as the degree of PBA surface functionalization increased. However, further increase in PBA surface functionalization (i.e. Dex-b-PLA_320 PBA) decreased the amount of mucin adsorbed. Without wishing to be bound by theory, it is possible that excess functionalization of the NP surfaces with PBA causes the Dextran to become more hydrophobic. This would increase the potential for self-aggregation of the NPs, reducing the total available surface area for mucin adsorption. It is therefore ideal to tune the amount of PBA functionalization to achieve optimal mucin-NP interaction without compromising the NP colloidal stability. It is also possible that smaller NPs render higher mucin adsorption due to their larger total surface area, as shown by comparing PLGA-PEG, Dex-b-PLA, and Dex-b-PLA_PBA NPs. However, as each type of NP exhibit different surface properties, the trend is inconclusive. The Dex-b-PLA_PBA NPs all exhibited significantly higher mucin adsorption compared to the previous studies involving chitosan based NPs and thiolated NPs, which showed about 0.25 and 0.13 mg/mg of NPs respectively at 1 hr incubation (Lee, 2006).

Mucoadhesion was calculated as the amount of mucin adsorbed per mg of NPs. NP suspension (1 ml) was mixed with 1 ml of mucin solution (1 mg/ml in STF) and incubated at 37° C. for 1 hr. The mixture was then centrifuged at 15,000 rpm for 1 hr and free mucin in the supernatant was quantified using the periodic acid/Schiff (PAS) staining method (Lee, 2006). Mucin adsorption was calculated by subtracting the free mucin concentration from the initial mucin concentration. Mucin standards (0.1, 0.25 and 0.5 mg/ml) were determined using the same procedure to obtain a calibration curve.

Example 10. In Vivo Studies 10.1 Acute Response Study Using Dex-b-PLA_PBA NPs

Figure 23:
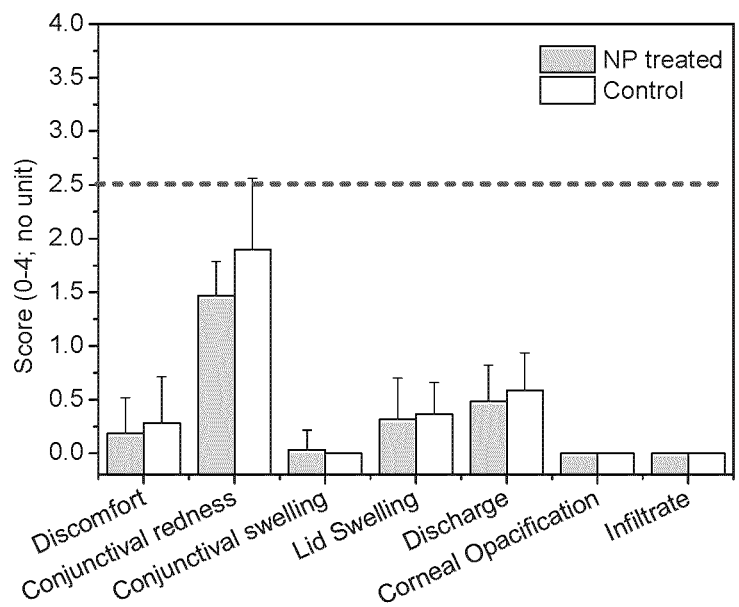
FIG. 23 demonstrates the compatibility of the exemplary NP formulation showing no short-term toxicity effect on the ocular surface in rabbits. NP treated and the control eyes (contralateral eyes) after one-time administration of the NP formulation were graded using 7 different categories (discomfort, conjunctival redness and swelling, lid swelling, discharge, corneal opacification, and infiltrate) by daily slit-lamp examination. The grades demonstrate that there is no significant increase in terms of severity of each category in the NP treated eye compared to the control eye.

To analyze the short-term biocompatibility of the NP formulation, the formulations were administered to rabbit eyes, while having contralateral eyes as control, and daily slit-lamp examination for up to 7 days was performed to analyze the ocular surface. Upon grading of the 7 categories (discomfort, conjunctival swelling and redness, lid swelling, discharge, corneal opacification, and infiltrate) from 0 (none) to 4 (severe), the control eyes showed overall higher values compared to the corresponding NP treated eyes (FIG. 23). Throughout the duration of the study, conjunctival swelling, corneal opacification, and infiltrate were not observed in any of the rabbits.

Three female rabbits (New Zealand Albino) were used for this study. The rabbits were acclimated for one week prior to the experiment. The nanoparticles are prepared using the nanoprecipitation method described in Example 4 but without the drug. The nanoparticles were filtered using 200 nm syringe filter, and further sterilized using UV irradiation inside a BioSafety Cabinet (BSC) for 1 hour. One eye was administered with NPs (28 µl 19 µg of Dex-b-PLA_PBA NPs) while the contra-lateral eye is used as control. Slit lamp examination at 0, 1, 8, 24, 48, 72, 96, 120, 144, and 168 hr after administration was used to evaluate 7 different categories (Note that 0 hr means before administration). These 7 categories (discomfort, conjunctival redness and swelling, lid swelling, discharge, corneal opacification, and infiltrate) were graded from 0 (no sign) to 4 (severe). After 168 hrs, the rabbits were euthanized, and the ocular tissues were collected in formalin for further histopathology analysis.

10.2 Histopathology Analysis of Ocular Tissues

Figure 24:
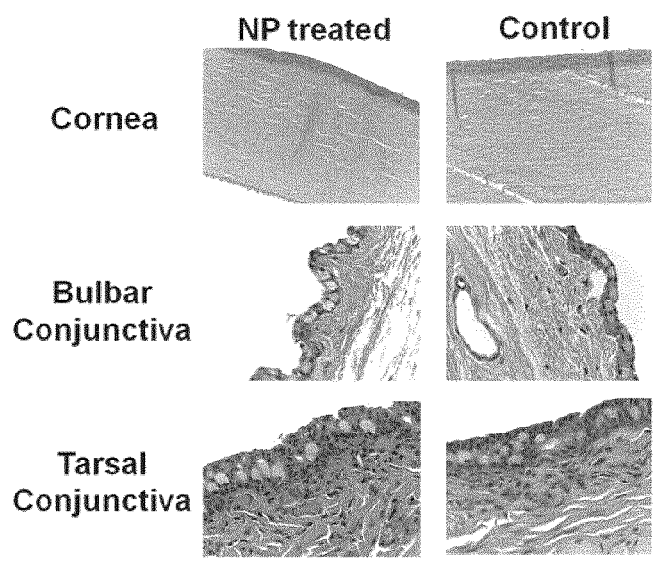
FIG. 24 shows the histopathology analysis of the cornea, bulbar and tarsal conjunctiva, one week after the administration of the exemplary NP formulation on rabbits. The results demonstrate that the structure and morphology of the ocular tissues are well-preserved after NP formulation and no sign of inflammation was observed.

After the duration of slit-lamp examination, the rabbits were euthanized and the ocular tissues (the entire ocular globe, and upper and lower eyelids) were collected for histopathology analysis (0). From examining the cornea, bulbar and tarsal conjunctivas of all the eyes, normal ocular tissues surfaces were observed in both the NP treated and the control eyes (FIG. 24). All eyes showed anterior segment with preserved architecture and morphology. No sign of inflammation, altered layer integrity, or presence of residual particles were detected in any of the eyes. Adequate number of goblet cells with preserved morphology was also shown. Presence of occasional intraepithelial and subepithelial eosinophils in tarsal conjunctiva were found in both NP treated and control eyes, suggesting that the phenomenon is not directly caused by the administration of the NP formulation.

The eyes were enucleated and collected immediately after euthanasia for histopathological evaluation. The entire upper and lower eyelids were also dissected and collected for evaluation of the tarsal conjunctiva and underlying soft tissues. Consecutive sections of the entire ocular globe and eyelids were processed for microscopic analysis: after initial fixation in 10% neutral buffered formalin, the tissue was embedded in paraffin, serially sectioned in 5 µm thick sections, and stained with hematoxylin and eosin (H&E). The histological slides were evaluated using bright field microscopy (Leica DM1000, ICC50 HD, Leica Microsystems Inc, Concord, ON).

10.3 Chronic Response Study Using Dex-b-PLA_PBA NPs

Figure 25:
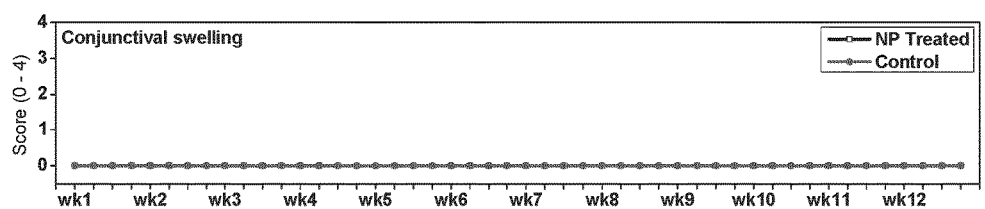
FIG. 25 demonstrates the compatibility of the exemplary NP formulation showing no long-term toxicity effect on the ocular surface in rabbits after weekly administration for up to 12 weeks. Chronic response of the ocular surfaces between NP treated and the control eyes (contralateral eyes) were evaluated similarly using 7 different categories (discomfort, conjunctival redness and swelling, lid swelling, discharge, corneal opacification, and infiltrate) by slit-lamp examination. The grades demonstrate that there is no significant difference in terms of severity of each category in the NP treated eye compared to the control eye throughout the duration of the study.
Figure 25:
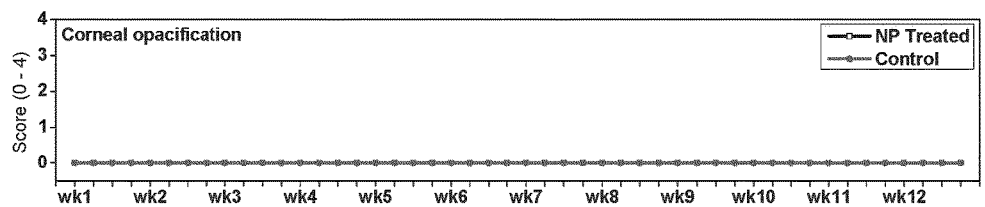
Figure 25:
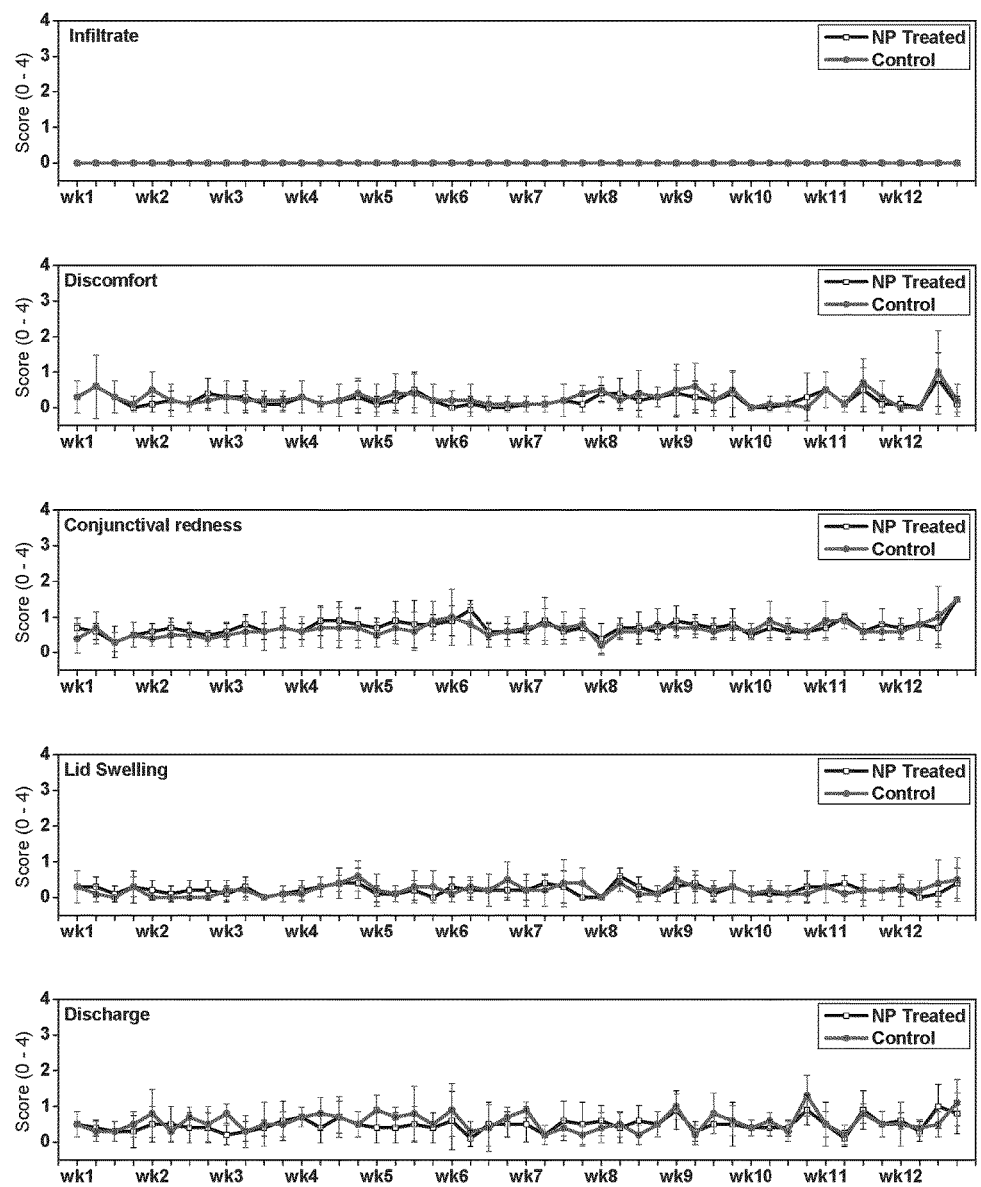

To analyze the long-term biocompatibility of the NP formulation, the formulations were administered to rabbit eyes once a week for up to 12 weeks, while having contralateral eyes as control, and daily slit-lamp examination was performed similar to above. Similar to acute response study, no sign of conjunctival swelling, corneal opacification, or infiltrate were observed in any of the rabbits at any point of the time during the study. Overall, the difference in values between the NP treated and control eyes were insignificant across all of the 7 categories throughout the duration of the study (12 weeks) (FIG. 25).

Five female rabbits (New Zealand Albino) were used for this study. The rabbits were acclimated for one week prior to the experiment. The nanoparticles are prepared using the nanoprecipitation method described in Example 4 but without the drug. The nanoparticles were filtered using 200 nm syringe filter, and further sterilized using UV irradiation inside a BioSafety Cabinet (BSC) for 1 hour. One eye was administered with NPs (28 µl; 19 µg of Dex-b-PLA_PBA NPs) once a week for 12 weeks while the contra-lateral eye is used as control. Slit lamp examination at 0, 1, 24, 48 hr after administration each week was used to evaluate 7 different categories (Note that 0 hr means before administration). These 7 categories (discomfort, conjunctival redness and swelling, lid swelling, discharge, corneal opacification, and infiltrate) were graded from 0 (no sign) to 4 (severe). After 12 weeks, the rabbits were euthanized, and the ocular tissues were collected for further histopathology analysis.

Figure 26:
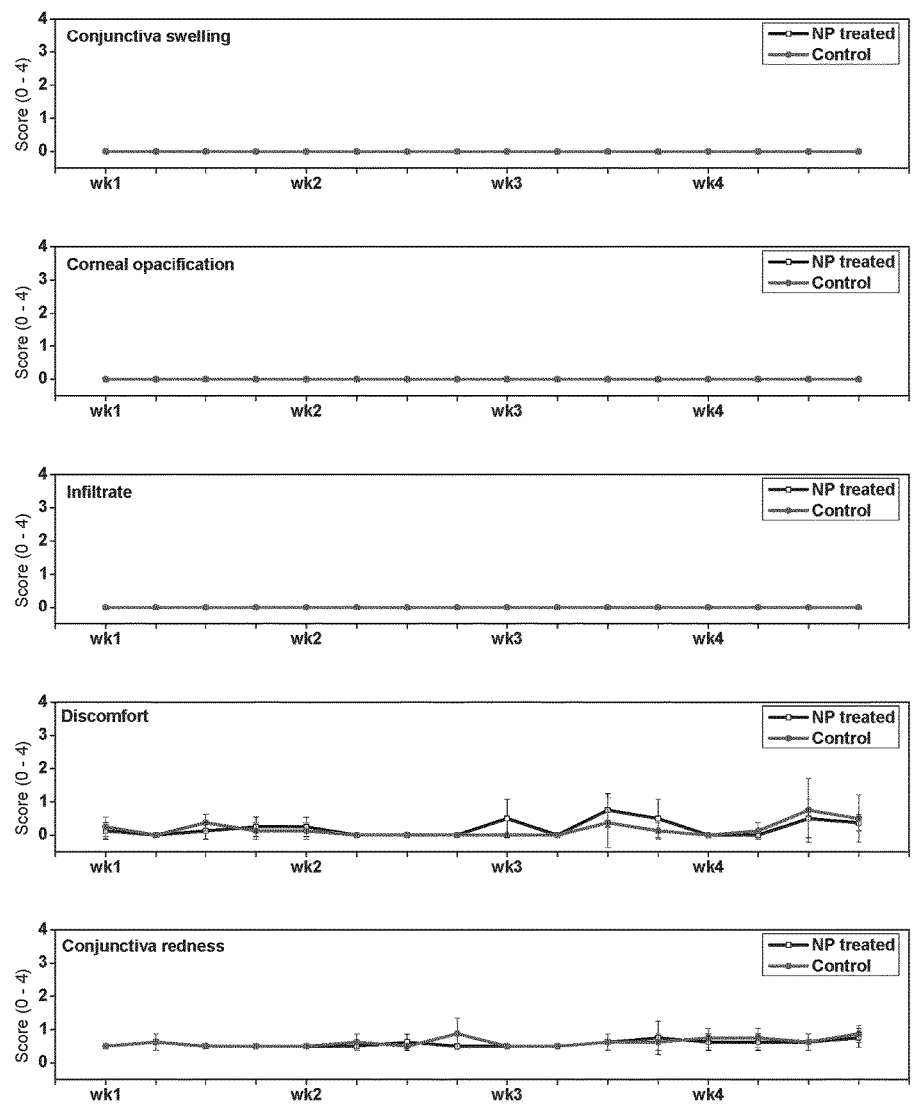
FIG. 26 compares the chronic response of the ocular surfaces between NP-drug treated and the control eyes (contralateral eyes) after weekly administration of formulation containing Cyclosporine A encapsulated NPs on rabbits. The grades of 7 different categories (discomfort, conjunctival redness and swelling, lid swelling, discharge, corneal opacification, and infiltrate) were obtained by daily slit-lamp examination for up to 4 weeks. The grades demonstrate that there is no significant difference in terms of severity of each category in the NP treated eye compared to the control eye throughout the duration of the study.
Figure 26:
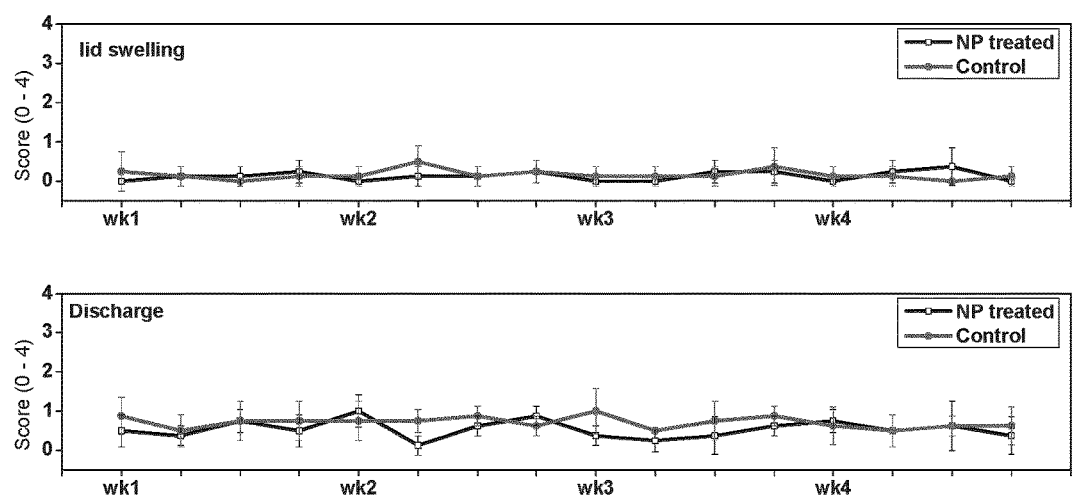

10.4 Chronic Response Study Using Dex-b-PLA_PBA NPs Encapsulated with Cyclosporine A Similarly, the long-term biocompatibility of the NP formulation with encapsulation of Cyclosporine A was also examined using slit-lamp. The formulation containing both the Dex-b-PLA_PBA NPs and Cyclosporine A were administered to rabbit eyes, while having contralateral eyes as control. The slit-lamp examination for up to 4 weeks has shown no significant difference between the NP treated and the control eyes in any of the 7 categories (FIG. 26).

Four female rabbits (New Zealand Albino) were used for this study. The rabbits were acclimated for one week prior to the experiment. The nanoparticles are prepared using the nanoprecipitation method described in Example 4 with Cyclosporine A. The nanoparticles were filtered using 200 nm syringe filter, and further sterilized using UV irradiation inside a BioSafety Cabinet (BSC) for 1 hour. One eye was administered with NPs (28 µl; 19 µg of Dex-b-PLA_PBA NPs and 8 µg of Cyclosporine A) once a week for 12 weeks, while the contra-lateral eye is used as control. Slit lamp examination at 0, 1, 24, 48 hr after administration each week was used to evaluate 7 different categories (Note that 0 hr means before administration). These 7 categories (discomfort, conjunctival redness and swelling, lid swelling, discharge, corneal opacification, and infiltrate) were graded from 0 (no sign) to 4 (severe). After 12 weeks, the rabbits were euthanized, and the ocular tissues were collected for further histopathology analysis.

Example 11. In Vitro Nanoparticle Partition Across Tear Fluid Lipid Layer

The ability of different types of NPs to partition across tear fluid lipid membrane was studied using in vitro model. The types of surface properties seem to have very little effect on the % of partition nanoparticle-drug complexes across the lipid membrane, with all of them achieve partition of approximately 70%. However, further studies are required to better simulate the structure and the turnover phenomenon of the lipid layer in the tear fluid.

Artificial tear fluid with lipid layer was prepared using previously reported method by preparing complex salt solution (CSS) and lipid stock solution (LSS) (Lorentz, 2009). Add LSS into 2000 fold volume of CSS and bath sonicate at 37° C. for 30 minutes. The mixture is allowed to settle overnight to form the lipid layer. Nanoparticles with Natamycin were prepared using the nanoprecipitation method described above. 1 ml of the NP-Natamycin formulation was added onto 2 ml of CSS/LSS mixture. The mixture was then incubated at 37° C. for 10 minutes. The bottom 1.5 ml of the mixture was extracted without disturbing the top layer, and dried overnight in vacuum desiccator. The precipitates were dissolved in DMSO again and UV-vis absorption was performed to calculate the concentration of Natamycin.

DISCUSSION

The present inventors synthesized a model linear block copolymer using PLA and Dextran (Dex-b-PLA), and demonstrated that NPs composed of Dex-b-PLA can self-assemble into core-shell structured NPs of small particle size, e.g. sizes less than 40 nm, without using any flow-focusing devices. They further showed that the size of Dex-b-PLA NPs can be precisely fine-tuned, e.g. between 15-70 nm by altering the molecular weight of the component blocks (Verma, 2012). Dextran, a natural polysaccharide composed of 1→6 linked α-D-glucopyranosyl units, was selected as a model hydrophilic block because of its high hydrophilicity and biocompatibility. Dextran has an abundance of functional hydroxyl groups on its back bone. The higher density of surface functional groups (as opposed to PEG, which has one functional group per chain) can improve the efficiency of surface functionalization, and thus, desirable surface properties are more easily achieved with Dextran based NPs. Dextran coated NPs showed excellent colloidal stability in physiological media in vitro and long retention in the systemic circulation in vivo (Verma, 2012; Albert, 1990).

There is a another fundamental difference in the structure of NPs composed of Dextran-PLA particles and PEG-PLA particles, which is due to the greater hydrophilicity of the Dextrans compared to that of PEG. The more hydrophilic Dextran is less likely randomly associated in the hydrophobic core of the NPs compared to PEG, which could also explain the increased drug encapsulated in the Dextran-PLA NPs compared to PLGA-PEG NPs (Verma, 2012).

NON-PATENT REFERENCES

1. Allen, T. M. and Hansen, C. Pharmacokinetics of stealth versus conventional liposomes—effect of dose. *Biochim. Biophys. Acta* 1991, 2, 133-141.
2. Allison Dev. Biol. Stand. 92:3-11, 1998.
3. A. J. Alpert. J. Chromatogr. 1990, 499, 177.
4. Bazile, D.; Prudhomme, C.; Bassoullet, M. T.; Marlard, M.; Spenlehauer, G.; Veillard, M. Stealth Me.PEG-PLA nanoparticles avoid uptake by the mononuclear phagocytes system. *J. Pharm. Sci.* 1995, 4, 493-498.
5. Bernkop-Schnurch, A., Improvement in the mucoadhesive properties of alginate by the covalent attachment of cysteine. *Journal of Controlled Release* 71 2001, 277-285.
6. Davidovich-Pinhas and Bianco-Peled. Novel mucoadhesive system based on sulfhydryl-acrylate interactions. *J. Mater Sci: Mater Med* 2010 21:2027-2034.
7. Chittasupho, C.; Xie, S.; Baoum, A.; Yakovleva, T.; Siahaan, T. J.; Berkland, C. J. ICAM-1 targeting of doxorubicin-loaded PLGA nanoparticles to lung epithelial cells. *Eur. J. Pharm. Sci.* 2009, 2, 141-150.
8. Cho, K.; Wang, X.; Nie, S.; Chen, Z.; Shin, D. M. Therapeutic nanoparticles for drug delivery in cancer. *Clin. Cancer. Res.* 2008, 5, 1310-1316.

9. Chouly, C.; Pouliquen, D.; Lucet, I.; Jeune, J. J.; Jallet, P. Development of superparamagnetic nanoparticles for MRI: Effect of particle size, charge and surface nature on biodistribution. *J. Microencapsul.* 1996, 3, 245-255.
10. Dhar, S.; Gu, F. X.; Langer, R.; Farokhzad, O. C.; Lippard, S. J. Targeted delivery of cisplatin to prostate cancer cells by aptamer functionalized Pt(IV) prodrug-PLGA-PEG nanoparticles. *Proc. Natl. Acad. Sci. U.S.A.* 2008, 45, 17356-17361.
11. Diebold, Y. and Calonge. Applications of nanoparticles in ophthalmology. *Progress in Retinal and Eye Research* 29 2010, 596-609.
12. Dobrovoiskaia, M. A.; Clogston, J. D.; Neun, B. W.; Hall, J. B.; Patri, A. K.; McNeil, S. E. Method for analysis of nanoparticle hemolytic properties in vitro. *Nano Lett.* 2008, 8, 2180-2187.
13. Dong, Y. and Feng, S. In vitro and in vivo evaluation of methoxy polyethylene glycol-polylactide (MPEG-PLA) nanoparticles for small-molecule drug chemotherapy. *Biomaterials* 2007, 28, 4154-4160.
14. Drummond, D. C.; Meyer, O.; Hong, K. L.; Kirpotin, D. B.; Papahadjopoulos, D. Optimizing liposomes for delivery of chemotherapeutic agents to solid tumors. *Pharmacol. Rev.* 1999, 4, 691-743.
15. L. C. du Toit, V. Pillay, Y. E. Choonara, T. Govender, T. Carmichael. Expert Opin. Drug Deliv. 2011, 8, 71.
16. Esmaeili, F.; Ghahremani, M. H.; Ostad, S. N.; Atyabi, F.; Seyedabadi, M.; Malekshahi, M. R.; Amini, M.; Dinarvand, R. Folate-receptor-targeted delivery of docetaxel nanoparticles prepared by PLGA-PEG-folate conjugate. *J. Drug Target.* 2008, 5, 415-423.
17. Fischer, D.; Li, Y. X.; Ahlemeyer, B.; Krieglstein, J.; Kissel, T. In vitro cytotoxicity testing of polycations: influence of polymer structure on cell viability and hemolysis. *Biomaterials* 2003, 7, 1121-1131.
18. Gaucher, G.; Asahina, K.; Wang, J.; Leroux, J. Effect of Poly(N-vinyl-pyrrolidone)-block-poly(D,L-lactide) as coating agent on the opsonization, phagocytosis, and pharmacokinetics of biodegradable nanoparticles. *Biomacromolecules* 2009, 2, 408-416.
19. Gaur, U.; Sahoo, S. K.; De, T. K.; Ghosh, P. C.; Maitra, A.; Ghosh, P. K. Biodistribution of fluoresceinated dextran using novel nanoparticles evading reticuloendothelial system. *Int. J. Pharm.* 2000, 1-2, 1-10.
20. Goodwin, A. P.; Tabakman, S. M.; Welsher, K.; Sherlock, S. P.; Prencipe, G.; Dai, H. Phospholipid-dextran with a single coupling point: a useful amphiphile for functionalization of nanomaterials. *J. Am. Chem. Soc.* 2009, 1, 289-296.
21. Gu, F.; Zhang, L.; Teply, B. A.; Mann, N.; Wang, A.; Radovic-Moreno, A. F.; Langer, R.; Farokhzad, O. C. Precise engineering of targeted nanoparticles by using self-assembled biointegrated block copolymers. *Proc. Natl. Acad. Sci. U.S.A.* 2008, 7, 2586-2591.
22. Guggi, et al., Matrix tablets based on thiolated poly (acrylic acid): pH-dependent variation in disintegration and mucoadhesion. *International Journal of Pharmaceutics* 274 2004 97-105.
23. He, C.; Hu, Y.; Yin, L.; Tang, C.; Yin, C. Effects of particle size and surface charge on cellular uptake and biodistribution of polymeric nanoparticles. *Biomaterials* 2010, 13, 3657-3666.
24. Kafedjiiski, et al., Improved synthesis and in vitro characterization of chitosan-thioethylamidine conjugate. *Biomaterials* 27, 2006, 127-135.
25. Karnik, R.; Gu, F.; Basto, P.; Cannizzaro, C.; Dean, L.; Kyei-Manu, W.; Langer, R.; Farokhzad, O. C. Microfluidic platform for controlled synthesis of polymeric nanoparticles. *Nano Lett.* 2008, 9, 2906-2912.
26. Khutoryanskiy, V. V Advances in Mucoadhesion and Mucoadhsive Polymers. *Macromol. Biosci.* 2011. 11, 748-764.
27. V. V. Khutoryanskiy. Macromolecular Bioscience 2011, 11, 748.
28. Kataoka, K.; Harada, A.; Nagasaki, Y. Block copolymer micelles for drug delivery: design, characterization and biological significance. *Adv. Drug Deliv. Rev.* 2001, 1, 113-131.
29. Kim, D.; El-Shall, H.; Dennis, D.; Morey, T. Interaction of PLGA nanoparticles with human blood constituents. *Colloids Surf. B Biointerfaces* 2005, 2, 83-91.
30. KusnierzGlaz, C. R.; Still, B. J.; Amano, M.; Zukor, J. D.; Negrin, R. S.; Blume, K. G.; Strober, S. Granulocyte colony-stimulating factor-induced comobilization of CD4 (−)CD8(−) T cells and hematopoietic progenitor cells (CD34(+)) in the blood of normal donors. *Blood* 1997, 7, 2586-2595.
31. Lee, H.; Fonge, H.; Hoang, B.; Reilly, R. M.; Allen, C. The effects of particle size and molecular targeting on the intratumoral and subcellular distribution of polymeric nanoparticles. *Mol. Pharm.* 2010, 4, 1195-1208.
32. Li, S. and Huang, L. Pharmacokinetics and biodistribution of nanoparticles. *Mol. Pharm.* 2008, 4, 496-504.
33. D. Lee, S. A. Shirley, R. F. Lockey, S. S. Mohapatra, Resp. Res. 2006, 7, 112.
34. N. Li, C. Zhuang, M. Wang, C. Sui, W. Pan. Drug Deliv. 2012, 19, 28.
35. S. Liu, L. Jones, F. X. Gu. *Macromolecular Bioscience* 2012, 12, 608.
36. Lorentz, et al. Contact lens physical properties and lipid deposition in a novel characterized artificial tear solution. *Molecular Vision* 2011: 17:3392-3405.
37. A. Ludwig. *Adv. Drug Deliv. Rev.* 2005, 57, 1595.
38. A. Matsumoto, H. Cabral, N. Sato, K. Kataoka, Y. Miyahara. Angewandte Chemie-International Edition 2010, 49, 5494.
39. A. Matsumoto, N. Sato, K. Kataoka, Y. Miyahara. J. Am. Chem. Soc. 2009, 131, 12022.
40. Missirlis, D.; Kawamura, R.; Tirelli, N.; Hubbell, J. A. Doxorubicin encapsulation and diffusional release from stable, polymeric, hydrogel nanoparticles. *Eur. J. Pharm. Sci.* 2006, 2, 120-129.
41. Magenheim, B.; Levy, M. Y.; Benita, S. A new in-vitro technique for the evaluation of drug-release profile from colloidal carriers—ultrafiltration technique at low-pressure. *Int. J. Pharm.* 1993, 1-3, 115-123.
42. Meerasa, A.; Huang, J. G.; Gu, F. X. CH(50): A revisited hemolytic complement consumption assay for evaluation of nanoparticles and blood plasma protein interaction. *Curr. Drug Deliv.* 2011, 3, 290-298.
43. Missirlis, D.; Kawamura, R.; Tirelli, N.; Hubbell, J. A. Doxorubicin encapsulation and diffusional release from stable, polymeric, hydrogel nanoparticles. *Eur. J. Pharm. Sci.* 2006, 2, 120-129.
44. Nagarwal, S. Kant, P. N. Singh, P. Maiti, J. K. Pandit. *J. Controlled Release* 2009, 136, 2.
45. Passirani, C.; Barratt, G.; Devissaguet, J. P.; Labarre, D. Long-circulating nanoparticles bearing heparin or dextran covalently bound to poly(methyl methacrylate). *Pharm. Res.* 1998, 7, 1046-1050.
46. Peracchia, M. T.; Fattal, E.; Desmaele, D.; Besnard, M.; Noel, J. P.; Gomis, J. M.; Appel, M.; d'Angelo, J.; Couvreur, P. Stealth® PEGylated polycyanoacrylate nanoparticles for intravenous administration and splenic targeting. *J. Control. Release* 1999, 1, 121-128.
47. Phillips et al. Vaccine 10:151-158, 1992.
48. Portet, D.; Denizot, B.; Rump, E.; Hindre, F.; Le Jeune, J. J.; Jallet, P. Comparative biodistribution of thin-coated iron oxide nanoparticles TCION: Effect of different bisphosphonate coatings. *Drug Dev. Res.* 2001, 4, 173-181.
49. Rehor, A.; Schmoekel, H.; Tirelli, N.; Hubbell, J. A. Functionalization of polysulfide nanoparticles and their performance as circulating carriers. *Biomaterials* 2008, 12, 1958-1966.
50. Riley, T.; Govender, T.; Stolnik, S.; Xiong, C. D.; Garnett, M. C.; Illum, L.; Davis, S. S. Colloidal stability and drug incorporation aspects of micellar-like PLA-PEG nanoparticles. *Colloids Surf. B Biointerfaces* 1999, 1-4, 147-159.
51. Riley, T.; Stolnik, S.; Heald, C. R.; Xiong, C. D.; Garnett, M. C.; Illum, L.; Davis, S. S.; Purkiss, S. C.; Barlow, R. J.; Gellert, P. R. Physicochemical evaluation of nanoparticles assembled from poly(lactic acid)-poly(ethylene glycol) (PLA-PEG) block copolymers as drug delivery vehicles. *Langmuir* 2001, 11, 3168-3174.
52. Sacco, J. J.; Botten, J.; Macbeth, F.; Bagust, A.; Clark, P. The Average Body Surface Area of Adult Cancer Patients in the UK: A Multicentre Retrospective Study. *Plos One* 2010, 1, e8933-e8933.
53. Safra, T.; Muggia, F.; Jeffers, S.; Tsao-Wei, D. D.; Groshen, S.; Lyass, O.; Henderson, R.; Berry, G.; Gabizon, A. Pegylated liposomal doxorubicin (doxil): Reduced clinical cardiotoxicity in patients reaching or exceeding cumulative doses of 500 mg/m(2). *Ann. Oncol.* 2000, 8, 1029-1033.
54. R. Shaikh, T. R. Raj Singh, M. J. Garland, A. D. Woolfson, R. F. Donnelly. Journal of pharmacy & bioallied sciences 2011, 3, 89.
55. Shuai, X. T.; Ai, H.; Nasongkla, N.; Kim, S.; Gao, J. M. Micellar carriers based on block copolymers of poly(e-caprolactone) and poly(ethylene glycol) for doxorubicin delivery. *J. Control. Release* 2004, 3, 415-426.
56. Sakloetsakun, et al., In situ gelling properties of chitosan-thioglycolic acid conjugate in the presence of oxidizing agents. *Biomaterials* 30, 2009, 6151-6157.
57. Schmitz, et al., Synthesis and characterization of chitosan-N-acetyl cysteine conjugate. *International Journal of Pharmaceutics* 347 2008, 79-85.
58. Shuai, X. T.; Ai, H.; Nasongkla, N.; Kim, S.; Gao, J. M. Micellar carriers based on block copolymers of poly(e-caprolactone) and poly(ethylene glycol) for doxorubicin delivery. *J. Control. Release* 2004, 3, 415-426.
59. R. Shaikh, T. R. Raj Singh, M. J. Garland, A. D. Woolfson, R. F. Donnelly. Journal of pharmacy & bioallied sciences 2011, 3, 89.
60. I. A. Sogias, A. C. Williams, V. V. Khutoryanskiy. Biomacromolecules 2008, 9, 1837.
61. J. Shen, Y. Deng, X. Jin, Q. Ping, Z. Su, L. Li. Int. J. Pharm. 2010, 402, 248.
62. Takeuchi, et al., Novel mucoadhesion tests for polymers and polymer-coated particles to design optimal mucoadhesive drug delivery systems. *Advanced Drug Delivery Reviews* 57 2005, 1583-1594.
63. Unkeless et al. Annu. Rev. Immunol. 6:251-281, 1998.
64. M. S. Verma, S. Liu, Y. Y. Chen, A. Meerasa, F. X. Gu. Nano Research 2012, 5, 49.
65. M. S. Verma, S. Liu, Y. Y. Chen, A. Meerasa, F. X. Gu. Nano Research 2012.
66. X. Yuan, H. Li, Y. Yuan. Carbohydr. Polym. 2006, 65, 337.
67. Yang, Z.; Leon, J.; Martin, M.; Harder, J. W.; Zhang, R.; Liang, D.; Lu, W.; Tian, M.; Gelovani, J. G.; Qiao, A., et al. Pharmacokinetics and biodistribution of near-infrared fluorescence polymeric nanoparticles. *Nanotechnology* 2009, 16, 165101-165101.
68. Zahr, A. S.; Davis, C. A.; Pishko, M. V. Macrophage uptake of core-shell nanoparticles surface modified with poly(ethylene glycol). *Langmuir* 2006, 19, 8178-8185.
69. A. Zimmer, J. Kreuter, Adv. Drug Deliv. Rev. 1995, 16, 61.

All references cited in this document are incorporated herein by reference in their entirety.

The above-described embodiments are intended to be examples only. Alterations, modifications and variations can be effected to the particular embodiments by those of skill in the art without departing from the scope of the disclosure, which is defined solely by the claims appended hereto.

What is claimed is:

1. A nanoparticle composition useful for delivery of a payload to a mucosal site, the nanoparticle composition comprising a plurality of linear amphiphilic diblock copolymers that assemble to form nanoparticles of the core-shell type, wherein the nanoparticles have a hydrophobic core and a hydrophilic shell, the copolymers consisting essentially of:
 a hydrophobic block comprising polylactide (PLA); and
 a hydrophilic block comprising dextran, the dextran comprising multiple functional moieties,
 wherein at least a portion of the functional moieties are conjugated to a phenylboronic acid (PBA) mucosal targeting moiety; and
 wherein the average particle size of the nanoparticles is less than 500 nm.

2. The composition of claim 1, wherein the nanoparticle is formed by conjugating the polylactide to the dextran to form a nanoparticle and subsequently surface-functionalizing the nanoparticle by conjugating at least a portion of the functional moieties of the dextran to the PBA to achieve a desired surface density of the PBA.

3. The composition of claim 2, wherein substantially all of the mucosal targeting moieties are on the surface of the nanoparticle.

4. The composition of claim 1, wherein the nanoparticle has a surface density of the mucosal targeting moiety, the surface density being tunable for adjustable targeting of the nanoparticle to the mucosal site.

5. The composition of claim 1, further comprising a payload.

6. The composition of claim 5, wherein the payload is a therapeutic agent.

7. The composition of claim 5, wherein the payload is an ophthalmic agent.

8. The composition of claim 7, wherein the ophthalmic agent is timolol, betaxolol, metipranolol, dorzolamide, cyclosporine, brinzolamide, neptazane, acetazolamide, alphagan, xalatan, bimatoprost, travaprost, olopatadine, ketotifen, acyclovir, gancyclovir, or valcyclovir.

9. The composition of claim 1, wherein the nanoparticles are dispersed in aqueous medium.

10. A pharmaceutical composition comprising a nanoparticle composition as defined in claim 6, and a pharmaceutically acceptable carrier.

11. The composition of claim 1, wherein the molecular weight of the hydrophobic portion is from about 0.1 kDa to about 2000 kDa.

12. The composition of claim 1, wherein the molecular weight of the hydrophobic portion is from about 0.5 kDa to about 200 kDa.

13. The composition of claim 1, wherein the molecular weight of the hydrophilic portion is from about 0.1 kDa to about 1000 kDa.

14. The composition of claim 1, wherein the molecular weight of the hydrophilic portion is from about 0.5 kDa to 100 kDa.

15. The composition of claim 1, wherein the molecular weight of the hydrophobic portion is from about 0.1 kDa to about 2000 kDa and wherein the molecular weight of the hydrophilic portion is from about 0.1 kDa to about 1000 kDa.

16. The composition of claim 1, wherein the average particle size of the nanoparticles is less than about 100 nm.

17. The nanoparticle of claim 1, wherein the copolymer is Dextran-NH-Et-NH-PLA.

* * * * *